US012630625B2

(12) United States Patent
Nagpal et al.

(10) Patent No.: US 12,630,625 B2
(45) Date of Patent: May 19, 2026

(54) IL-18/IL-23 MULTISPECIFIC ANTIGEN BINDING PROTEINS

(71) Applicant: GlaxoSmithKline Intellectual Property Development Limited, Stevenage (GB)

(72) Inventors: Sunil Nagpal, Collegeville, PA (US); Helen Payne, Stevenage (GB); Yanxia Guo, Collegeville, PA (US); Joel Tocker, Collegeville, PA (US)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 0 days.

(21) Appl. No.: 19/243,022

(22) Filed: Jun. 19, 2025

(65) Prior Publication Data

US 2026/0008843 A1     Jan. 8, 2026

Related U.S. Application Data

(60) Provisional application No. 63/662,557, filed on Jun. 21, 2024.

(51) Int. Cl.
*C07K 16/24* (2006.01)
*A61P 29/00* (2006.01)

(52) U.S. Cl.
CPC ............ *C07K 16/244* (2013.01); *A61P 29/00* (2018.01); *C07K 2317/31* (2013.01); *C07K 2317/52* (2013.01); *C07K 2317/565* (2013.01); *C07K 2317/71* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 8,637,018 B2 | 1/2014 | Ellis | |
| 9,499,617 B2 | 11/2016 | Ellis | |
| 11,078,265 B2 * | 8/2021 | Nabozny | A61P 19/02 |
| 2010/0189718 A1 * | 7/2010 | Dall'Acqua | C07K 16/283 |
| | | | 435/5 |

FOREIGN PATENT DOCUMENTS

| | | | |
|---|---|---|---|
| EP | 2500353 A2 | 9/2012 | |
| WO | WO-2010020593 A1 | 2/2010 | |
| WO | WO-2020254826 A1 | 12/2020 | |
| WO | WO-2022186772 A1 | 9/2022 | |
| WO | WO2023/209568 | 11/2023 | |

OTHER PUBLICATIONS

Caron et al (Bispecific antibodies for the treatment in inflammatory bowel disease: an avenue worth exploring? Expert Opin Biol Ther. Aug. 2022;22(8):951-953). (Year: 2022).*

Chen et al. (The Effects of Adoptively Transferred IL-23/IL-18-Polarized Neutrophils on Tumor and Collagen-Induced Arthritis in Mice. J Inflamm Res. 2021; 14:4669-4686. Published Sep. 16, 2021 (Year: 2021).*

Hale (Living in LALA land? Forty years of attenuating Fc effector functions. Immunol Rev. Nov. 2024;328(1):422-437) (Year: 2024).*

Guha et al., Very Early-Onset IBD-Associated IL 18opathy Treated with an Anti-IL18 Antibody, J. Clin. Med. 2024, 13, 6058 (8 pages).

International Search Report and Written Opinion for International Application No. PCT/EP2025/067261, mailed Sep. 26, 2025, 14 Pages.

Clinicaltrial.gov [online] "NCT03681067: A Clinical Trial of Antibody GSK1070806 in the Treatment of Patients With Moderate to Severe Crohn's Disease (CDAID)," Retrieved on Jan. 10, 2026, Retrieved from URL: https://clinicaltrials.gov/study/NCT03681067, 12 pages.

Clinicaltrial.gov [online] "NCT04752371: A Study to Evaluate Camoteskimab in Participants With Still's Disease," Retrieved on Jan. 10, 2026, Retrieved from URL: https://clinicaltrials.gov/study/NCT04752371, 13 pages.

Gabay C., et al., Open-label, Multicentre, Dose-escalating Phase II Clinical Trial on the Safety and Efficacy of Tadekinig Alfa (IL-18BP) In Adult-onset Still's Disease, Clinical and Epidemiological Research, Jun. 2018, vol. 77(6), pp. 840-847, Retrieved from [doi:10.1136/annrheumdis-2017-212608].

* cited by examiner

*Primary Examiner* — Zachariah Lucas
*Assistant Examiner* — Sarah A Alsomairy
(74) *Attorney, Agent, or Firm* — Donald Huddler; Nicole Ginanni

(57) ABSTRACT

The present disclosure provides multispecific antigen binding proteins that bind to one or more cytokines, more particularly to pro-inflammatory cytokines. In particular, the present disclosure relates to multispecific antigen binding proteins that comprise an interleukin 18 (IL-18) binding domain and an interleukin 23 (IL-23) binding domain, and the use of said multispecific antigen binding proteins in medicine.

9 Claims, 6 Drawing Sheets

Figure 1:
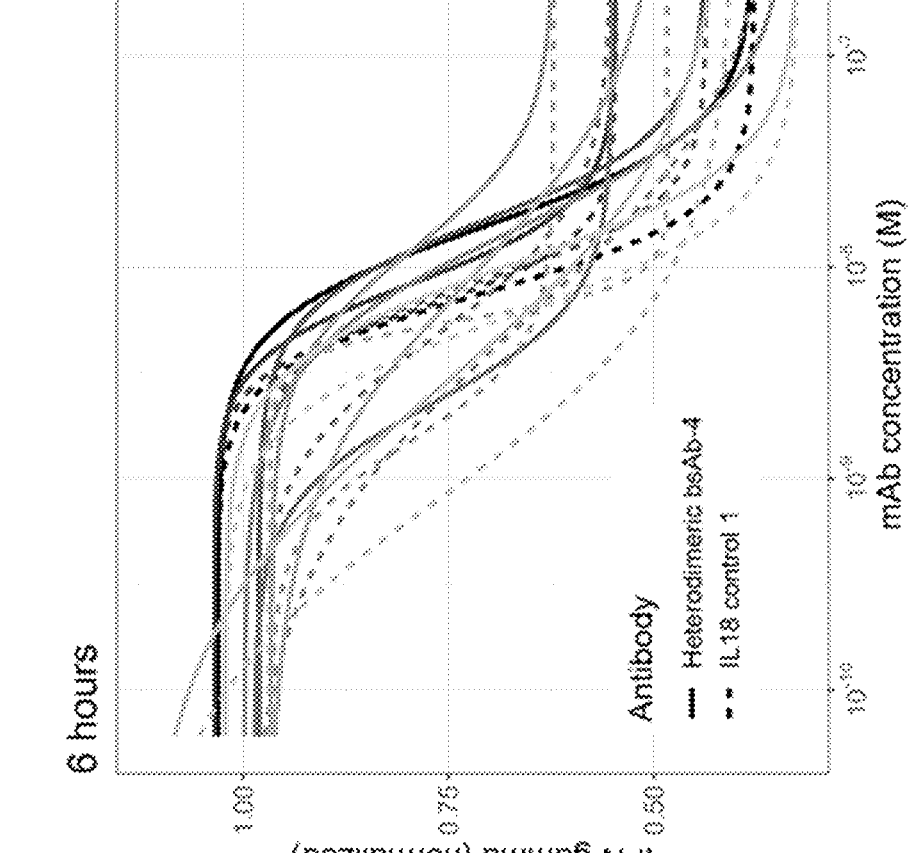

Specification includes a Sequence Listing.

1

IL-18/IL-23 MULTISPECIFIC ANTIGEN BINDING PROTEINS

CROSS-REFERENCE TO RELATED APPLICATIONS

This application is a non-provisional application which claims the benefit under 35 USC 119(e) of U.S. Provisional Patent Application No. 63/662,557, filed Jun. 21, 2024. This application is incorporated by reference herein.

SEQUENCE LISTING SUBMITTED ELECTRONICALLY

This application contains a sequence listing, which is provided in XML format with a file name "70506FF.xml". The XML file has a size of about 80,030 bytes and was created on or about Jun. 4, 2025. The sequence listing submitted electronically is part of the specification and is incorporated herein by reference in its entirety.

FIELD OF THE INVENTION

The invention is directed to multispecific antigen binding proteins. More specifically, it is directed to multispecific antigen binding proteins that comprise an interleukin 18 (IL-18) binding domain and an interleukin 23 (IL-23) binding domain.

BACKGROUND TO THE INVENTION

Inflammatory bowel disease (IBD) is a multi-factorial chronic relapsing immune-mediated disease characterised by inflammation of the gastrointestinal (GI) tract. The two main subtypes of IBD are Crohn's Disease (CD) and Ulcerative Colitis (UC). Although the pathogenesis of IBD is not fully understood, it is thought to be driven by dysregulated innate and adaptive immune responses against intestinal microorganisms in genetically susceptible people. Disease burden for many patients remains onerous and although some patients can achieve remission through corticosteroids or aminosalicylates, effective maintenance therapy is key to successful outcomes and reduction in life-long complications.

To this end, biological therapies have changed the treatment paradigm for those suffering with IBD. The first monoclonal antibody against tumor necrosis factor alpha (anti-TNF-α) was approved for use in IBD in 1998, however more recently, biologics with different mechanisms of action, have shown clinical efficacy (Juillerat et al, Curr Res Pharmacol Drug Discov. (2022); 3: 100104). For example, monoclonal antibodies that specifically bind to the homing receptor α4β7 integrin complex (e.g., vedolizumab), to the interleukin (IL) p40 subunit common to IL12/23 (ustekinumab), to the B7 subunit of integrins α4β7 and αEβ7 (e.g., etrolizumab), as well as to p19 subunit of interleukin 23 (e.g., guselkumab, mirikizumab and risankizumab) are emerging in the market.

Although biologic agents are commonly used as monotherapies for IBD, it is reported that only 40% of patients achieve remission within one year of therapy (Hirten et al. *Clin Gastroenterol Hepatol.* 2018; 16:1374-1384). Furthermore, a large proportion of IBD patients will not achieve remission that is long lasting (Gisbert et al (2020) J Crohn's and Colitis). Global prevalence of IBD (both UC and CD) is also rising which will pose a substantial and economic burden on governments and health systems (Alatab et al, Lancet Gastroenterol Hepatol 2020; 5: 17-30).

There remains a need for additional effective therapies for IBD and other immunoinflammatory diseases, in particular therapies that are more efficacious, with higher rates of (and more sustained) remission of disease.

SUMMARY OF THE INVENTION

The present invention provides multispecific antigen binding proteins that bind to both interleukin (IL-18) and interleukin 23 (IL-23) with high affinity.

Activation of immune cells, with subsequent production of cytokines and mediators, contributes to both IBD disease symptoms (e.g., chronic diarrhoea, abdominal pain, rectal bleeding) as well as complications of IBD (e.g., cancer, stenosis, ulcer formation, fistulas and epithelial-mesenchymal transition). In particular, innate lymphoid cells (ILCs), T-cells, macrophages, neutrophils and dendritic cells (DCs) may mediate tissue damage. Furthermore, effector memory T cells (TEM cells) and innate-like T cells, including mucosal-associated invariant T (MAIT) cells, for example, can migrate into the gut and can contribute to intestinal inflammation and tissue destruction as well as extra-intestinal manifestations (Neurath, M. F. *Nat Immunol* 20, 970-979 (2019) and Toubal, A et al. *Nat Rev Immunol* 19, 643-657 (2019)). Without wishing to be bound by theory, targeting a concomitant block of both IL-18 and IL-23 is predicted to reduce activation and/or migration of gut-homing inflammatory cells and reduce cytokine release (e.g., from MAIT cells and Th1/Th17 cells).

Notably, the inventors surprisingly discovered that dual blockade of IL-18 and IL-23 using multispecific antigen binding proteins have enhanced activity in downregulating C-X-C Motif Chemokine Ligand 13 (CXCL13) expression, compared to anti-IL-18 and anti-IL-23 controls alone. In view of the critical role that CXCL13 plays in the pathogenesis of IBD, the multispecific antigen binding proteins disclosed herein have promise in terms of their ability to provide additional effective therapies for IBD and other immunoinflammatory diseases (Liu T et al 2022, Front. Immunol. 13:997862. doi: 10.3389/fimmu. 2022.997862).

Therefore, in a first aspect there is provided a multispecific antigen binding protein comprising an interleukin 18 (IL-18) binding domain and an interleukin 23 (IL-23) binding domain.

In a further aspect there is provided an anti-IL-18 and anti-IL-23 bispecific antibody comprising anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7 and anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15.

In a further aspect there is provided a nucleic acid sequence encoding the multispecific antigen binding protein or the bispecific antibody of the disclosure. Further provided is a nucleic acid sequence encoding any one, two, three or all four of the following amino acid sequences: a heavy chain of SEQ ID NO: 54, a light chain of SEQ ID NO: 56, a heavy chain of SEQ ID NO: 55, and a light chain of SEQ ID NO:57.

In a further aspect there is provided an expression vector comprising the nucleic acid sequence(s) of the disclosure.

In a further aspect there is provided a recombinant host cell comprising the nucleic acid sequence(s) or the expression vector(s) of the disclosure. Further provided is a method for the production of a multispecific antigen binding protein, said method comprising culturing the recombinant host cells of the disclosure under conditions suitable for expression of said nucleic acid sequence(s) or vector(s), whereby said multispecific antigen binding protein is produced. Multispecific antigen binding proteins produced by said method are further provided.

In a further aspect there is provided a cell line engineered to express the multispecific antigen binding protein or the bispecific antibody according to the disclosure.

In a further aspect there is provided a pharmaceutical composition comprising the multispecific antigen binding protein or the bispecific antibody according to the disclosure and a pharmaceutically acceptable excipient.

In a further aspect there is provided a method for the treatment of disease in a subject in need thereof comprising administering to said subject a therapeutically effective amount of the multispecific antigen binding protein, the bispecific antibody or the pharmaceutical composition according to the disclosure. In an embodiment the disease is an immunoinflammatory disease. In an embodiment the immunoinflammatory disease is IBD.

In a further aspect there is provided the multispecific antigen binding protein, the bispecific antibody or the pharmaceutical composition according to the disclosure for use in the treatment of disease. In an embodiment the disease is an immunoinflammatory disease. In an embodiment the immunoinflammatory disease is IBD.

In a further aspect there is provided the use of a multispecific antigen binding protein, a bispecific antibody or a pharmaceutical composition according to the disclosure in the manufacture of a medicament for use in the treatment of an immunoinflammatory disease. In an embodiment the immunoinflammatory disease is IBD.

DESCRIPTION OF DRAWINGS/FIGURES

FIG. 1.: Heterodimeric bsAb-4 inhibition of LPS+IL12-induced IFNγ in human whole blood. Healthy donor whole blood was treated with LPS and IL-12 in the presence of increasing concentrations of IL-18 control 1 (dashed lines) or Heterodimeric bsAb-4 (solid lines) (n=9) for 6 hr. Negative control 3 was used as an isotype control.

Figure 2:
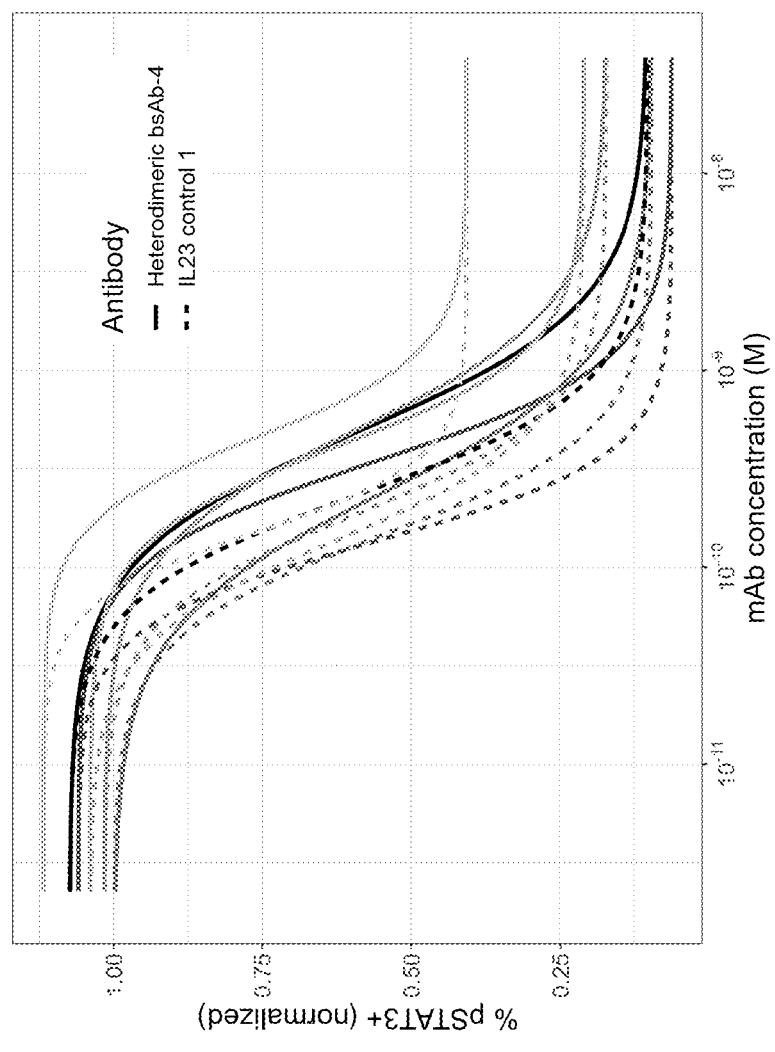

FIG. 2.: Heterodimeric bsAb-4 neutralization of IL-23-induced pSTAT3 in human whole blood. Healthy donor whole blood was treated with recombinant IL-23 in the presence of increasing concentrations of IL-23 control 1 (dashed lines) or Heterodimeric bsAb-4 (solid lines) (n=6). Dose-response (four-parameter logistic) curves for each antibody and donor were fit with a shared min and max between antibodies for every donor.

Figure 3:
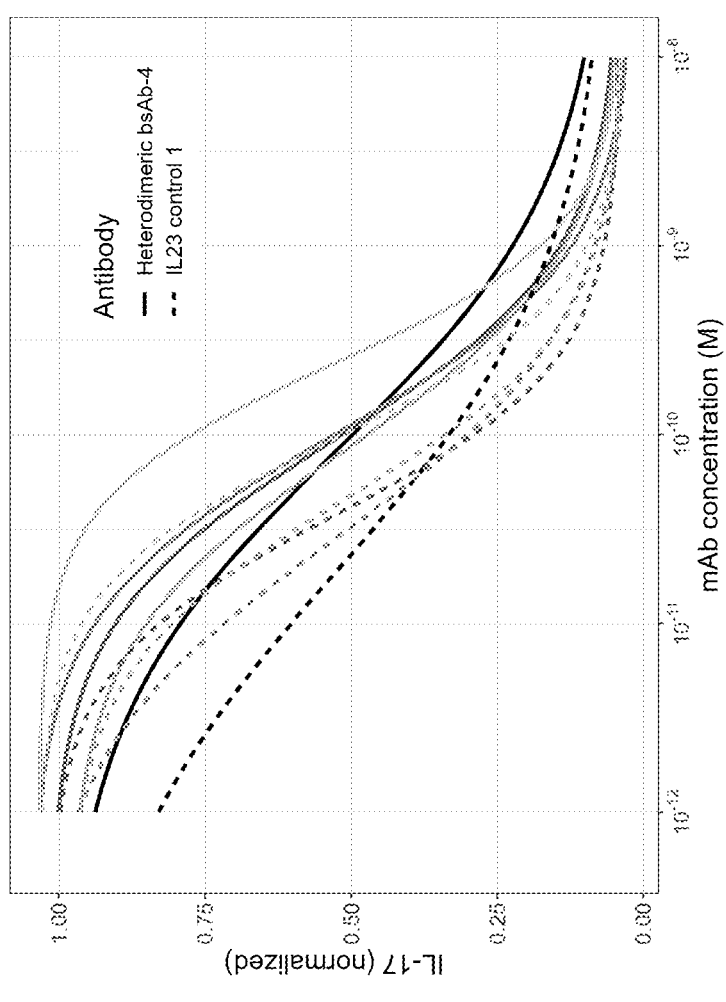

FIG. 3.: Heterodimeric bsAb-4 neutralization of human IL-23-induced IL-17A in mouse splenocytes. Freshly isolated mouse splenocytes were treated with recombinant IL-23 in the presence of increasing concentrations of IL-23 control 1 (dashed lines) or Heterodimeric bsAb-4 (solid lines) (n=5). After 72 hrs, IL-17A secretion into the supernatant was assessed using MSD assay. The data were normalized to the mean "no antibody" control response (representing 100%, or 1.0) on each assay plate. The normalized data were pooled across experiments and dose-response (four-parameter logistic) curves for each antibody were fit with a shared min and max between antibodies for every experiment.

Figure 4:
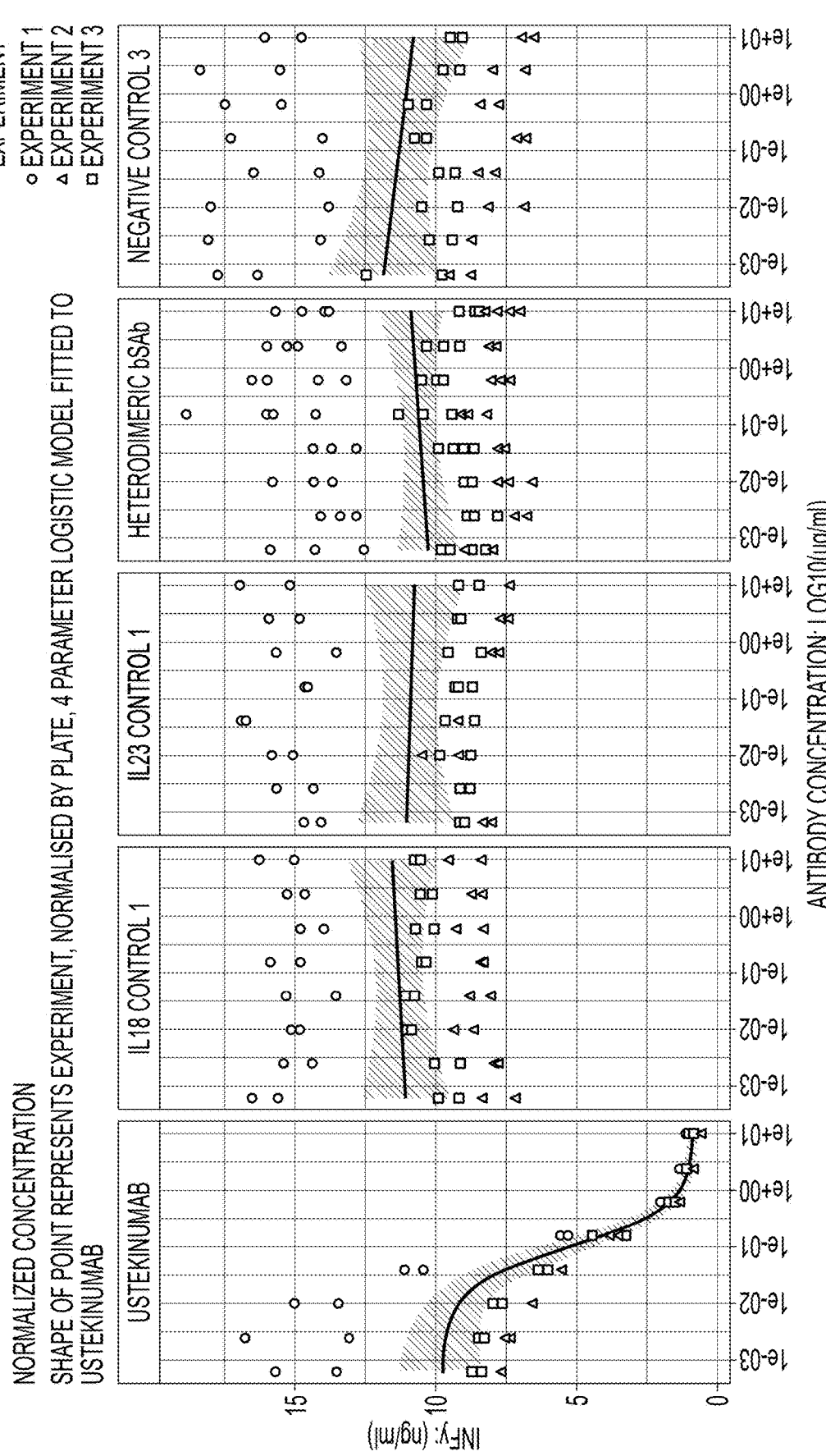

FIG. 4.: Selectivity of Heterodimeric bsAb-4 for IL-23p19 demonstrated using an IL-12 induced IFNγ secretion assay. NK92 cells were treated with recombinant IL-12 in the presence of increasing concentrations of Ustekinumab, negative control 3, IL-23 control 1, IL-18 control 1 or Heterodimeric bsAb-4 (n=3 experiments). After 24 hrs, IFNγ secretion into the supernatant was assessed using MSD assay (n=3). Data were normalized to no-stimulus (no IL-12) controls per plate with a dose-response (four-parameter logistic) curve fitted to the Ustekinumab data. An IC50 mean estimate of 0.13 ug/mL (875 pM) was calculated for Ustekinumab from the dose response curve generated with logarithmic transformation.

Figure 5:
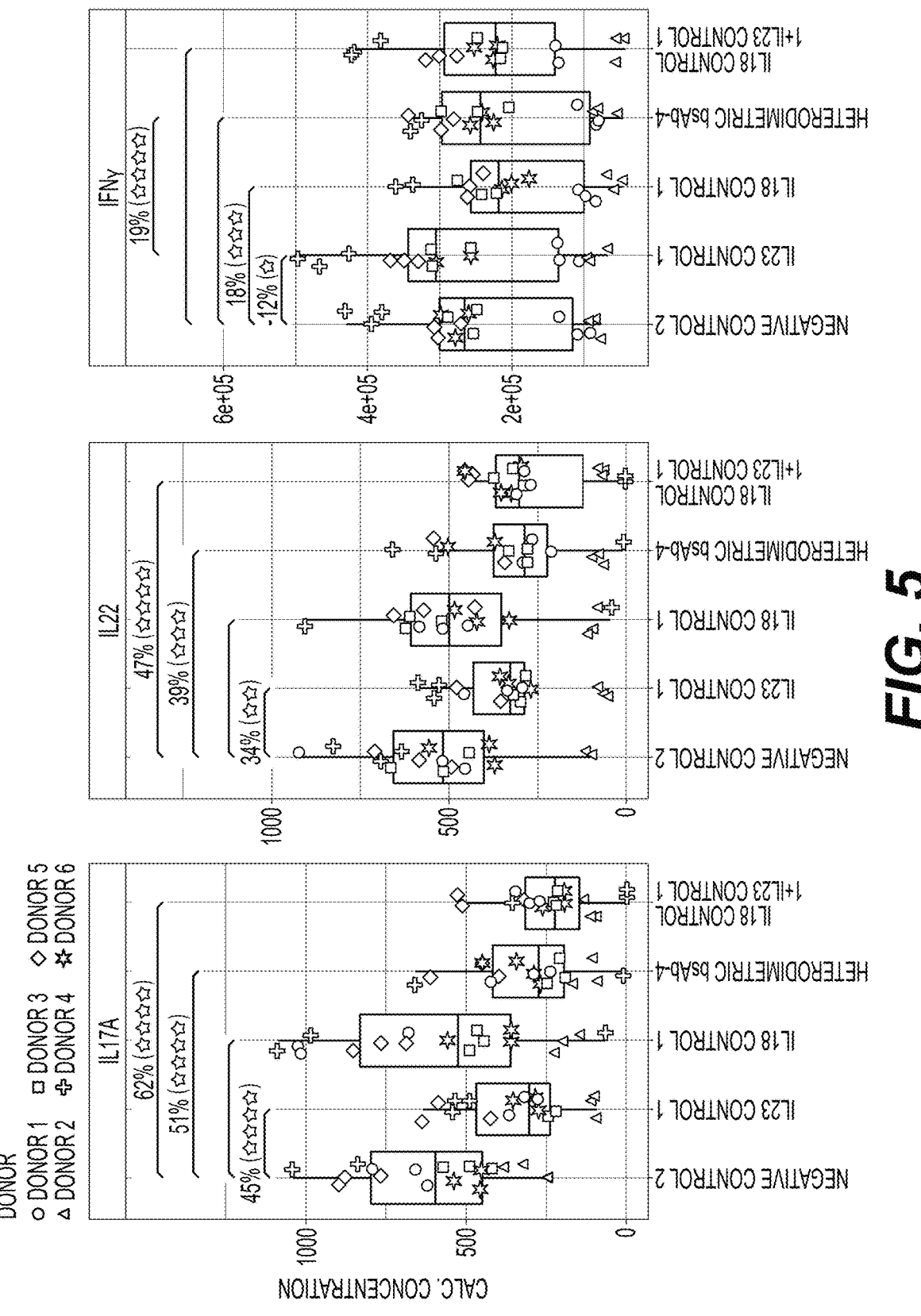

FIG. 5.: Heterodimeric bsAb inhibition of IL-17A, IL-22 and IFNγ secretion in myeloid+ T cell co-culture system measured by MSD. Differentiated myeloid cells were co-cultured with CD3$^+$ T cells from different donors. IL-23 control, and IL-18 control 1 were used at 5 μg/ml. Heterodimeric bsAb was used as 10 μg/ml. IFNγ secretion was measured by MSD on day 2. IL17A and IL22 were measured by MSD on day 2 and 6 but only day 6 data is shown in graph. All pairwise comparisons were evaluated, accounting for donor-to-donor variability and using a Tukey adjustment for multiple comparisons. Displayed above are only the comparisons to Negative Control 2 for IL17A and IL22. Also shown for IFNγ is the comparison between IL-23 Control 1 and Heterodimeric bsAb-4. Percentages show the percent decrease from Negative Control 2 (or IL-23 Control 1) for each significant difference (p-value<0.05). *: p-value<0.05; : p-value<0.01; *: p-value<0.001; ****: p-value<0.0001.

Figure 6:
Figure 6:
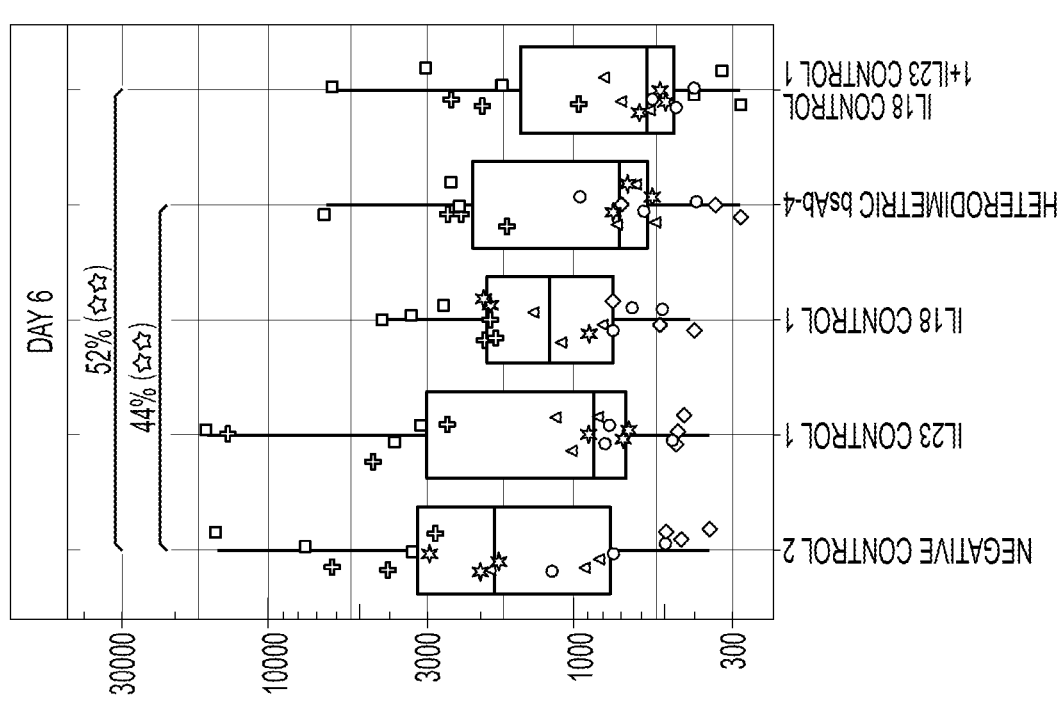

FIG. 6.: Heterodimeric bsAb-4 regulation of CXCL13 in myeloid+ T cell co-culture system measured by Nomic analysis. Differentiated myeloid cells were co-cultured with CD3$^+$ T cells from different donors. IL-23 control 1 and IL-18 control 1 were used at 5 μg/ml. Heterodimeric bsAb-4 was used as 10 μg/ml. CXCL13 was measured by Nomic on day 2 and 6. A separate model was built for each day, incorporating donor-to-donor variability. Comparisons to negative control 2 and Heterodimeric bAb-4 were calculated, with only statistically significant comparisons shown. Statistically significant comparisons to negative control 2 include the estimated percent inhibition from control. *: p-value<0.05: : p-value<0.01; *: p-value<0.001.

DETAILED DESCRIPTION OF THE INVENTION

Unless defined otherwise, all technical and scientific terms used herein have the same meaning as commonly understood by one of ordinary skill in the art to which this disclosure belongs.

"Affinity", also referred to as "binding affinity", as used herein is the strength of binding at a single interaction site, i.e., of one molecule, e.g., a binding domain (such as an IL-18 or IL-23 binding domain), to another molecule, e.g., its target antigen, at a single binding site. The binding affinity of an IL-18 binding domain or an IL-23 binding domain to IL-18 or IL-23, respectively, may be determined by equilibrium methods (e.g., enzyme-linked immunoabsorbent assay (ELISA) or radioimmunoassay (RIA)), or kinetics (e.g., surface plasmon resonance analysis using a BIACORE instrument or equivalent). For example, the BIACORE method described in Examples 2 & 3 may be used to measure binding affinity and to measure binding kinetics.

As used herein the term "antagonist" means a molecule that blocks, attenuates or otherwise interferes with the biological activity of another molecule to which it is capable of binding or interacting with.

An "antibody" as used herein refers to a molecule with an immunoglobulin-like domain (for example IgG, IgM, IgA, IgD or IgE) and includes a monoclonal, recombinant, poly- clonal, chimeric, human, humanized, multispecific, includ- ing bispecific, and heteroconjugate antibody. The term, "full", "whole" or "intact" antibody, used interchangeably herein, refers to a heterotetrameric glycoprotein. An intact monospecific bivalent IgG antibody, for example as found in nature in humans, is composed of two identical heavy chains (HCs) and two identical light chains (LCs) linked by cova- lent disulphide bonds. This H2L2 structure folds to form three functional domains comprising two antigen-binding fragments, known as 'Fab' fragments, and a 'Fc' crystallis- able fragment. The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences, which are called μ, α, γ, ε and δ respectively, each heavy chain can pair with either a κ or λ light chain. The majority of antibodies in human serum belong to the IgG class, there are four isotypes of human IgG (IgG1, IgG2, IgG3 and IgG4), the sequences of which differ mainly in their hinge region.

The term "antigen binding protein" refers to antibodies and other protein constructs, such as domains, that are capable of binding to said antigen(s). This does not include the natural cognate ligand or receptor. The term "multispe- cific antigen binding protein" refers to antibodies and other protein constructs that bind two or more different epitopes (for example, two, three, four or more different epitopes). As used herein, the term multispecific antigen binding protein refers to antibodies and other protein constructs that are capable of binding to and neutralizing at least two antigens: IL-18 and IL-23. Accordingly, "IL-18 and IL-23 binding protein" and "multispecific antigen binding protein" may be used interchangeably herein. An example of a multispecific antibody is a "bispecific antibody" which binds two different epitopes. Multispecific antigen binding proteins include antibodies and antibody-derived molecules, as well as alter- native antibody formats in which one or more CDRs are arranged on a suitable non-immunoglobulin protein scaffold or skeleton. Examples of antigen binding proteins include a single variable domain (e.g., a domain antibody (DAB)), antigen binding antibody fragments, Fab, F(ab')2, Fv, dis- ulphide linked Fv, single chain Fv, disulphide-linked scFv, diabodies, TANDABS, an affibody, a SpA scaffold, an LDL receptor class A domain, an avimer (see, e.g., U.S. Patent Application Publication Nos. 2005/0053973, 2005/0089932, 2005/0164301) or an EGF domain etc. and modified ver- sions of any of the foregoing (for a summary of alternative "antibody" formats see Holliger and Hudson, Nature Bio- technology, 2005, Vol 23, No. 9, 1126-1136).

As used herein, a "bispecific antibody" is an antibody capable of binding to, and neutralizing, two antigens: IL-18 and IL-23. Accordingly, "anti-IL-18 and anti-IL-23 bispe- cific antibody" and "bispecific antibody" are used inter- changeably herein.

"CDRs" are defined as the complementarity determining region amino acid sequences of an antigen binding protein.

These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs. Throughout this specification, amino acid residues in vari- able domain sequences and variable domain regions within full-length antigen binding sequences, e.g., within an anti- body heavy chain sequence or antibody light chain sequence, are numbered according to the Kabat numbering convention. Similarly, the terms "CDR", "CDRL1", "CDRL2", "CDRL3", "CDRH1", "CDRH2", "CDRH3" used in the Examples follow the Kabat numbering conven- tion. For further information, see Kabat et al., Sequences of Proteins of Immunological Interest, 4th Ed., U.S. Depart- ment of Health and Human Services, National Institutes of Health (1987). It will be apparent to those skilled in the art that there are alternative numbering conventions for amino acid residues in variable domain sequences and full-length antibody sequences. There are also alternative numbering conventions for CDR sequences, for example those set out in Chothia et al. (1989) Nature 342: 877-883. Other num- bering conventions for CDR sequences available to a skilled person include "AbM" (University of Bath) and "contact" (University College London) methods. The table below represents one definition using each numbering convention for each CDR or binding unit. The Kabat numbering scheme is used in Table 1 to number the variable domain amino acid sequence. It should be noted that some of the CDR defini- tions may vary depending on the individual publication used.

| | Kabat CDR | Chothia CDR | AbM CDR | Contact CDR |
|---|---|---|---|---|
| H1 | 31-35/35A/35B | 26-32/33/34 | 26-35/35A/35B | 30-35/35A/35B |
| H2 | 50-65 | 52-56 | 50-58 | 47-58 |
| H3 | 95-102 | 95-102 | 95-102 | 93-101 |
| L1 | 24-34 | 24-34 | 24-34 | 30-36 |
| L2 | 50-56 | 50-56 | 50-56 | 46-55 |
| L3 | 89-97 | 89-97 | 89-97 | 89-96 |

CDRs may be modified by at least one amino acid substitution, deletion or addition, wherein the variant anti- gen binding protein substantially retains the biological char- acteristics of the unmodified protein, such as binding to IL-18 or IL-23. It will be appreciated that each of CDR H1, H2, H3, L1, L2, L3 may be modified alone or in combination with any other CDR, in any permutation or combination. In one embodiment, a CDR is modified by the substitution, deletion or addition of up to 3 amino acids, for example 1 or 2 amino acids, for example 1 amino acid. Typically, the modification is a substitution, particularly a conservative substitution, for example as shown in the Table below. For example, in a variant CDR, the flanking residues that comprise the CDR as part of alternative definition(s) e.g. Kabat or Chothia, may be substituted with a conservative amino acid residue. Such antigen binding proteins compris- ing variant CDRs as described above may be referred to herein as "functional CDR variants".

| Side chain | Members |
|---|---|
| Hydrophobic | Met, Ala, Val, Leu, Ile |
| Neutral hydrophilic | Cys, Ser, Thr |
| Acidic | Asp, Glu |

7

-continued

| Side chain | Members |
|---|---|
| Basic | Asn, Gln, His, Lys, Arg |
| Residues that influence chain orientation | Gly, Pro |
| Aromatic | Trp, Tyr, Phe |

"Co-administering" refers to the process of administering two or more different compositions at substantially the same time during a biomedical procedure, although, it will be understood that said administrations do not have to be perfectly concurrent i.e., one of said compositions can be administered before or after the other(s) during the same biomedical procedure. In an embodiment, the two or more different compositions are administered simultaneously, separately or sequentially. In an embodiment, the period of time elapsing between the administrations is limited e.g., less than 2-hours apart.

The term "derived" is intended to define not only the source in the sense of it being the physical origin for the material but also to define material, which is structurally identical to the material, but which does not originate from the reference source.

The term "domain" refers to a folded polypeptide structure which retains its tertiary structure independent of the rest of the polypeptide. Generally, domains are responsible for discrete functional properties of polypeptides and in many cases may be added, removed, or transferred to other polypeptides without loss of function of the remainder of the protein and/or of the domain.

The term "Effector Function" as used herein refers to one or more of antibody-mediated effects including antibody-dependent cell-mediated cytotoxicity (ADCC), antibody-mediated complement activation including complement-dependent cytotoxicity (CDC), complement-dependent cell-mediated phagocytosis (CDCP), antibody dependent complement-mediated cell lysis (ADCML), and Fc-mediated phagocytosis or antibody-dependent cellular phagocytosis (ADCP).

"Half-life" or "t½" refers to the time required for the serum concentration of an antigen binding protein to reach half of its original value. The serum half-life of proteins can be measured by pharmacokinetic studies according to the method described by Kim et al., 1994, Eur. J. of Immuno. 24: 542-548. According to this method, radio-labelled protein is injected intravenously into mice and its plasma concentration is periodically measured as a function of time, for example, at about 3 minutes to about 72 hours after the injection. Other methods for pharmacokinetic analysis and determination of the half-life of a molecule will be familiar to those skilled in the art.

A "HET mAb" is an IgG-like molecule that targets two different epitopes, either on the same or different targets. A "HET mAb" is an example of a bispecific antibody. As used herein, a "HET mAb" binds to two different targets: IL-18 and IL-23. A HET mAb has four distinct chains: two non-identical heavy chains and two non-identical light chains. These chains contain a set of mutations in the Fc portion of the molecule that drive heavy chain dimerization and a set of mutations on the Fab portion that drive correct heavy/light chain pairing, e.g., kappa/kappa or lambda/kappa subtype bispecific mAbs. Suitable mutations for driving heavy chain dimerization are disclosed in WO2012/058768 and WO2013/063702. Suitable mutations for driving HC/LC pairing are disclosed in WO2014/082179, WO2015/181805, and WO2017/059551.

As used herein the term "immunoinflammatory disease" or "immunoinflammatory disorder" encompasses a variety of conditions, including autoimmune diseases. Immunoinflammatory diseases are characterized by dysregulation of the immune system more particularly by inappropriate activation of the immune response which damages the body's own tissues.

"Interleukin 18 (IL-18)" also known as "interferon-gamma inducing factor" is a proinflammatory cytokine involved in epithelial barrier repair, polarized T-helper 1 (Th1) cell and natural killer (NK) cell immune responses. The sequence of human IL-18 is set out in SEQ ID NO:1 (see also UniProt #Q14116). Many cell types, both hematopoietic cells and non-hematopoietic cells, have the potential to produce IL-18. IL-18 is constitutively expressed in non-hematopoietic cells, such as intestinal epithelial cells, keratinocytes, and endothelial cells. IL-18 can modulate both innate and adaptive immunity.

"IL-18 binding domain" or "domain that binds to IL-18" as used herein refers to a domain capable of binding to and neutralising IL-18.

"Interleukin-23 (IL-23)" is a heterodimeric pro-inflammatory cytokine. IL-23 is mainly secreted by activated macrophages and dendritic cells located in peripheral tissues (skin, intestinal mucosa and lung) as a disulphide-linked complex (McKenzie et al, Trends Immunol. 2006; 27:17-23). Human IL-23 is composed of a common subunit (p40) with IL12 (see SEQ ID NO: 75 herein and UniProt #P29460) and a unique p19 subunit (see SEQ ID NO: 74 herein and UniProt #Q9NPF7) although the biological activity of IL-23 is only detected when the two subunits are partnered. IL-23 supports the development and maintenance of a recently defined set of CD4 T helper cells termed Th17 cells due to their ability to produce IL-17 and related cytokines.

"IL-23 binding domain" "or domain that binds IL-23" as used herein refers to a domain capable of binding to and neutralising IL-23. An IL-23 binding domain may be any of the IL-23 binding domains disclosed herein. Alternatively, the IL-23 binding domain may be any of the IL-23 binding proteins as disclosed in WO2009/043933 or WO2010/115786.

The term "neutralises" as used herein means that the biological activity of a particular target is reduced in the presence of a binding molecule that binds to said target. In terms of the present disclosure therefore, neutralises may mean that the biological activity of IL-23 is reduced in the presence of a IL-23 binding domain as described herein in comparison to the activity of IL-23 in the absence of the IL-23 binding domain, in vitro or in vivo; or that the biological activity of IL-18 is reduced in the presence of an IL-18 binding domain as described herein in comparison to the activity of IL-18 in the absence of the IL-18 binding domain, in vitro or in vivo, as appropriate. In both cases, neutralization may be due to one or more of blocking the target (e.g., IL-18 and/or IL-23) binding to its receptor, preventing the target (e.g., IL-18 and/or IL-23) from activating its receptor, down regulating the target (e.g., IL-18 and/or IL-23) or its receptor, or affecting effector functionality. The reduction or inhibition in biological activity may be partial or total.

"Percent identity" or "% identity" between a query amino acid sequence and a subject amino acid sequence is the "Identities" value, expressed as a percentage, that is calculated using a suitable algorithm or software, such as BLASTP, FASTA, DNASTAR Lasergene, GeneDoc, Bioedit, EMBOSS needle or EMBOSS infoalign, over the entire length of the query sequence after a pair-wise global sequence alignment has been performed using a suitable algorithm/software such as BLASTP, FASTA, ClustalW, MUSCLE, MAFFT, EMBOSS Needle, T-Coffee, and DNASTAR Lasergene. Importantly, a query amino acid sequence may be described by a amino acid sequence disclosed herein, e.g., an amino acid sequence identified in one or more of the claims. "Percent identity" or "% identity" between a query nucleic acid sequence and a subject nucleic acid sequence is the "Identities" value, expressed as a percentage, that is calculated using a suitable algorithm (e.g. BLASTN, FASTA, Needleman-Wunsch, Smith-Waterman, LALIGN, or GenePAST/KERR) or software (e.g. DNAS-TAR Lasergene, GenomeQuest, EMBOSS needle or EMBOSS infoalign), over the entire length of the query sequence after a pair-wise global sequence alignment has been performed using a suitable algorithm (e.g. Needleman-Wunsch or GenePAST/KERR) or software (e.g. DNASTAR Lasergene or GenePAST/KERR). Importantly, a query nucleic acid sequence may be described by a nucleic acid sequence disclosed herein, in particular in one or more of the claims.

The query sequence may be 100% identical to the subject sequence, or it may include up to a certain integer number of amino acid or nucleotide alterations as compared to the subject sequence such that the % identity is less than 100%. For example, the query sequence is at least 50, 60, 70, 75, 80, 85, 90, 95, 96, 97, 98, or 99% identical to the subject sequence. Such alterations include at least one amino acid deletion, substitution (including conservative and non-conservative substitution), or insertion, and wherein said alterations may occur at the amino- or carboxy-terminal positions of the query sequence or anywhere between those terminal positions, interspersed either individually among the amino acids or nucleotides in the query sequence or in one or more contiguous groups within the query sequence. The % identity may be determined across the entire length of the query sequence, including the CDRs. Alternatively, the % identity may exclude one or more or all of the CDRs, for example all of the CDRs are 100% identical to the subject sequence and the % identity variation is in the remaining portion of the query sequence, e.g., the framework sequence, so that the CDR sequences are fixed and intact.

"Protein Scaffold" as used herein includes, but is not limited to, an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. The protein scaffold may be an Ig scaffold, for example an IgG, or IgA scaffold. The IgG scaffold may comprise some or all the domains of an antibody (i.e., CH1, CH2, CH3, VH, VL). The protein scaffold may be a derivative of a scaffold selected from the group consisting of CTLA-4, lipocalin, Protein A derived molecules such as Z-domain of Protein A (Affibody, SpA), A-domain (Avimer/Maxibody); heat shock proteins such as GroEl and GroES; transferrin (trans-body); ankyrin repeat protein (DARPin); peptide aptamer; C-type lectin domain (Tetranectin); human γ-crystallin and human ubiquitin (affilins); PDZ domains; scorpion toxin kunitz type domains of human protease inhibitors; and fibronectin/adnectin; which has been subjected to protein engineering in order to obtain binding to an antigen other than the natural ligand.

The term "single variable domain" refers to a folded polypeptide domain comprising sequences characteristic of antibody variable domains. It therefore includes complete antibody variable domains such as VH, VHH and VL and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain can bind an antigen or epitope independently of a different variable region or domain. A "domain antibody" or "DAB" may be considered the same as a "single variable domain". A single variable domain may be a human single variable domain, but also includes single variable domains from other species such as rodent (for example, as disclosed in WO 00/29004 A1), nurse shark and Camelid VHH DABs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanized according to standard techniques available in the art, and such domains are considered to be "single variable domains". As used herein, VH includes camelid VHH domains.

The term "therapeutically effective amount" refers to the quantity of a multispecific antigen binding protein or bispecific antibody disclosed herein that will elicit the desired biological response in a subject. It may vary depending on the disease and its severity and the age and weight of the subject to be treated, as well as the multispecific antigen binding protein or bispecific antibody used.

The term "therapy" encompasses alleviation, reduction, or prevention of at least one aspect or symptom of a disease. Compositions:

The present disclosure provides compositions comprising an IL-18 antagonist for example an IL-18 binding protein (e.g., anti-IL-18 antibody or a recombinant human IL-18 binding protein, such as Tadekinig alfa).

In an embodiment said IL-18 antagonist is an IL-18 binding protein (e.g., anti-IL-18 antibody) comprising the following CDRs: a) CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7; b) CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71; or c) CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81.

Further provided herein are compositions comprising an IL-23 antagonist, for example an IL-23 binding protein (e.g., anti-IL-23 antibody). In an embodiment said IL-23 antagonist is an IL-23 binding protein (e.g., anti-IL-23 antibody) comprising the following CDRs: a) CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15; b) CDRH1 of SEQ ID NO: 18, CDRH2 of SEQ ID NO: 19, CDRH3 of SEQ ID NO: 20, CDRL1 of SEQ ID NO: 21, CDRL2 of SEQ ID NO: 22 and CDRL3 of SEQ ID NO: 23; c) CDRH1 of SEQ ID NO: 26, CDRH2 of SEQ ID NO: 27, CDRH3 of SEQ ID NO: 28, CDRL1 of SEQ ID NO: 29, CDRL2 of SEQ ID NO: 30 and CDRL3 of SEQ ID NO: 31; d) CDRH1 of SEQ ID NO: 34, CDRH2 of SEQ ID NO: 35, CDRH3 of SEQ ID NO: 36, CDRL1 of SEQ ID NO: 37, CDRL2 of SEQ ID NO: 38 and CDRL3 of SEQ ID NO: 39; or e) CDRH1 of SEQ ID NO: 58, CDRH2 of SEQ ID NO: 59, CDRH3 of SEQ ID NO: 60, CDRL1 of SEQ ID NO: 61, CDRL2 of SEQ ID NO: 62 and CDRL3 of SEQ ID NO: 63.

Said composition comprising an IL-18 antagonist and said composition comprising an IL-23 antagonist may be particularly useful in medicine when co-administered to a subject. Thus, in an embodiment there is provided a method of treating an immunoinflammatory disease (e.g., IBD) in a subject in need thereof comprising co-administering to said subject a therapeutically effective amount of said composition comprising an IL-18 binding protein and a therapeutically effective amount of said composition comprising an IL-23 binding protein.

The present disclosure also provides compositions comprising an IL-18 antagonist and an IL-23 antagonist, for example a composition comprising an IL-18 binding protein (e.g., anti-IL-18 antibody or a recombinant human IL-18 binding protein, such as Tadekinig alfa) and an IL-23 binding protein (e.g., anti-IL-23 antibody). For example, the present disclosure provides a composition comprising:

i) an IL-18 binding protein (e.g., anti-IL-18 antibody) comprising the following CDRs: a) CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7; b) CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71; or c) CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81; and ii) an IL-23 binding protein (e.g., anti-IL-23 antibody) comprising the following CDRs: a) CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15; b) CDRH1 of SEQ ID NO: 18, CDRH2 of SEQ ID NO: 19, CDRH3 of SEQ ID NO: 20, CDRL1 of SEQ ID NO: 21, CDRL2 of SEQ ID NO: 22 and CDRL3 of SEQ ID NO: 23; c) CDRH1 of SEQ ID NO: 26, CDRH2 of SEQ ID NO: 27, CDRH3 of SEQ ID NO: 28, CDRL1 of SEQ ID NO: 29, CDRL2 of SEQ ID NO: 30 and CDRL3 of SEQ ID NO: 31; d) CDRH1 of SEQ ID NO: 34, CDRH2 of SEQ ID NO: 35, CDRH3 of SEQ ID NO: 36, CDRL1 of SEQ ID NO: 37, CDRL2 of SEQ ID NO: 38 and CDRL3 of SEQ ID NO: 39; or e) CDRH1 of SEQ ID NO: 58, CDRH2 of SEQ ID NO: 59, CDRH3 of SEQ ID NO: 60, CDRL1 of SEQ ID NO: 61, CDRL2 of SEQ ID NO: 62 and CDRL3 of SEQ ID NO: 63.

Any combination of the anti-IL-18 and anti-IL-23 antibodies described above is foreseen by the present disclosure. For example, the anti-IL-18 antibody may be an antibody comprising the CDRs as described in i)/a) above (i.e. CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7) and the anti-IL-23 antibody may be an antibody comprising the CDRs as described in any of ii)/a), b), c), d) or e) above. Likewise, the anti-IL-18 antibody may be an antibody comprising the CDRs as described in i)/b) above (i.e. CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71) and the anti-IL-23 antibody may be an antibody comprising the CDRs as described in any of ii)/a), b), c), d) or e) above. Likewise, the anti-IL-18 antibody may be an antibody comprising the CDRs as described in i)/c) above (i.e. CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81) and the anti-IL-23 antibody may be an antibody comprising the CDRs as described in any of ii)/a), b), c), d) or e) above.

In an embodiment there is provided a composition comprising:

i) an IL-18 binding protein (e.g., anti-IL-18 antibody) comprising a) a VH domain of SEQ ID NO: 8 and/or a VL domain of SEQ ID NO: 9; b) a VH domain of SEQ ID NO: 72 and/or a VL domain of SEQ ID NO: 73 or c) a VH domain of SEQ ID NO: 82 and/or a VL domain of SEQ ID NO: 83; and ii) an IL-23 binding protein (e.g., anti-IL-23 antibody) comprising a) a VH domain of SEQ ID NO: 16 and/or a VL domain of SEQ ID NO: 17; b) a VH domain of SEQ ID NO: 24 and/or a VL domain of SEQ ID NO: 25; c) a VH domain of SEQ ID NO: 32 and/or a VL domain of SEQ ID NO: 33; d) a VH domain of SEQ ID NO: 40 and/or a VL domain of SEQ ID NO: 41; or e) a VH domain of SEQ ID NO: 64 and/or a VL domain of SEQ ID NO: 65.

Again, any combination of the anti-IL-18 and anti-IL-23 antibodies described above is foreseen by the present disclosure. For example, the anti-IL-18 antibody may be an antibody comprising the VH/VL domains as described in i)/a) above (i.e. comprising a VH domain of SEQ ID NO: 8 and/or a VL domain of SEQ ID NO: 9) and the anti-IL-23 antibody may be an antibody comprising the VH/VL domains as described in any of ii)/a), b), c), d) or e) above. Likewise, the anti-IL-18 antibody may be an antibody comprising the VH/VL domains as described in i)/b) above (i.e., a VH domain of SEQ ID NO: 72 and/or a VL domain of SEQ ID No: 73) and the anti-IL-23 antibody may be an antibody comprising the VH/VL domains as described in any of ii)/a), b), c), d) or e) above. Likewise, the anti-IL-18 antibody may be an antibody comprising the VH/VL domains as described in i)/c) above (i.e., a VH domain of SEQ ID NO: 82 and/or a VL domain of SEQ ID NO: 83) and the anti-IL-23 antibody may be an antibody comprising the VH/VL domains as described in any of ii)/a), b), c), d) or e) above.

The compositions comprising an IL-18 antagonist and an IL-23 antagonist (e.g., an anti-IL-18 antibody and an anti-IL-23 antibody) described above may be useful in medicine. There is therefore provided a method of treating an immunoinflammatory disease (e.g., IBD) in a subject in need thereof comprising administering to said subject a therapeutically effective amount of said compositions. Further provided are said compositions for use in the treatment of immunoinflammatory disease (e.g., IBD).

Multispecific Antigen Binding Proteins:

The present disclosure provides multispecific antigen binding proteins, in particular bispecific antibodies, that bind to (or are capable of binding to) IL-18 and IL-23.

Thus, in a first aspect, there is provided a multispecific antigen binding protein comprising an interleukin 18 (IL-18) binding domain and an interleukin 23 (IL-23) binding domain.

In an embodiment said multispecific antigen binding protein comprises an IL-18 binding domain and an IL-23 binding domain wherein said IL-18 binding domain binds to human IL-18 and said IL-23 binding domain binds to human IL-23. In an embodiment said IL-23 binding domain binds to human IL-23-p19.

In an embodiment said multispecific antigen binding protein comprises an IL-18 binding domain and an IL-23 binding domain wherein said IL-18 binding domain comprises the following CDRs:

a. CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7;

b. CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71; or c. CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81.

In particular said multispecific antigen binding protein comprises an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7.

In an embodiment said multispecific antigen binding protein comprises an IL-18 binding domain and an IL-23 binding domain wherein said IL-23 binding domain comprises the following CDRs:

a. CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15;

b. CDRH1 of SEQ ID NO: 18, CDRH2 of SEQ ID NO: 19, CDRH3 of SEQ ID NO: 20, CDRL1 of SEQ ID NO: 21, CDRL2 of SEQ ID NO: 22 and CDRL3 of SEQ ID NO: 23;

c. CDRH1 of SEQ ID NO: 26, CDRH2 of SEQ ID NO: 27, CDRH3 of SEQ ID NO: 28, CDRL1 of SEQ ID NO: 29, CDRL2 of SEQ ID NO: 30 and CDRL3 of SEQ ID NO: 31;

d. CDRH1 of SEQ ID NO: 34, CDRH2 of SEQ ID NO: 35, CDRH3 of SEQ ID NO: 36, CDRL1 of SEQ ID NO: 37, CDRL2 of SEQ ID NO: 38 and CDRL3 of SEQ ID NO: 39; or e. CDRH1 of SEQ ID NO: 58, CDRH2 of SEQ ID NO: 59, CDRH3 of SEQ ID NO: 60, CDRL1 of SEQ ID NO: 61, CDRL2 of SEQ ID NO: 62 and CDRL3 of SEQ ID NO: 63.

In particular said multispecific antigen binding protein comprises an IL-18 binding domain and an IL-23 binding domain wherein said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15.

Provided herein are multispecific antigen binding proteins comprising any combination of the above-mentioned IL-18 binding domains and IL-23 binding domains (each combination being provided below as follows):

In an embodiment, said multispecific antigen binding protein comprises an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15.

In an embodiment, said multispecific antigen binding protein comprises an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 18, CDRH2 of SEQ ID NO: 19, CDRH3 of SEQ ID NO: 20, CDRL1 of SEQ ID NO: 21, CDRL2 of SEQ ID NO: 22 and CDRL3 of SEQ ID NO: 23.

In an embodiment, said multispecific antigen binding protein comprises an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 26, CDRH2 of SEQ ID NO: 27, CDRH3 of SEQ ID NO: 28, CDRL1 of SEQ ID NO: 29, CDRL2 of SEQ ID NO: 30 and CDRL3 of SEQ ID NO: 31.

In an embodiment, said multispecific antigen binding protein comprises an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 34, CDRH2 of SEQ ID NO: 35, CDRH3 of SEQ ID NO: 36, CDRL1 of SEQ ID NO: 37, CDRL2 of SEQ ID NO: 38 and CDRL3 of SEQ ID NO: 39.

In an embodiment, said multispecific antigen binding protein comprises an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 58, CDRH2 of SEQ ID NO: 59, CDRH3 of SEQ ID NO: 60, CDRL1 of SEQ ID NO: 61, CDRL2 of SEQ ID NO: 62 and CDRL3 of SEQ ID NO: 63.

In an embodiment, said multispecific antigen binding protein comprises an IL-18 binding domain and an IL-23 binding domain wherein said IL-18 binding domain comprises the following CDRs: CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71 and said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15.

In an embodiment, said multispecific antigen binding protein comprises an IL-18 binding domain and an IL-23 binding domain wherein said IL-18 binding domain comprises the following CDRs: CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71 and said IL-23 binding domain comprises the following CDRs: CDRH1 of SEQ ID NO: 18, CDRH2 of SEQ ID NO: 19, CDRH3 of SEQ ID NO: 20, CDRL1 of SEQ ID NO: 21, CDRL2 of SEQ ID NO: 22 and CDRL3 of SEQ ID NO: 23.

In an embodiment, said multispecific antigen binding protein comprises an IL-18 binding domain and an IL-23 binding domain wherein said IL-18 binding domain comprises the following CDRs: CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71 and said IL-23 binding domain comprises the following CDRs: CDRH1 of SEQ ID NO: 26, CDRH2 of SEQ ID NO: 27, CDRH3 of SEQ ID NO: 28, CDRL1 of SEQ ID NO: 29, CDRL2 of SEQ ID NO: 30 and CDRL3 of SEQ ID NO: 31.

In an embodiment, said multispecific antigen binding protein comprises an IL-18 binding domain and an IL-23 binding domain wherein said IL-18 binding domain comprises the following CDRs: CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71 and said IL-23 binding domain comprises the following CDRs: CDRH1 of SEQ ID NO: 34, CDRH2 of SEQ ID NO: 35, CDRH3 of SEQ ID NO: 36, CDRL1 of SEQ ID NO: 37, CDRL2 of SEQ ID NO: 38 and CDRL3 of SEQ ID NO: 39.

In an embodiment, said multispecific antigen binding protein comprises an IL-18 binding domain and an IL-23 binding domain wherein said IL-18 binding domain comprises the following CDRs: CDRH1 of SEQ ID NO: 66, CDRH2 of SEQ ID NO: 67, CDRH3 of SEQ ID NO: 68, CDRL1 of SEQ ID NO: 69, CDRL2 of SEQ ID NO: 70 and CDRL3 of SEQ ID NO: 71 and said IL-23 binding domain comprises the following CDRs: CDRH1 of SEQ ID NO: 58, CDRH2 of SEQ ID NO: 59, CDRH3 of SEQ ID NO: 60, CDRL1 of SEQ ID NO: 61, CDRL2 of SEQ ID NO: 62 and CDRL3 of SEQ ID NO: 63.

In an embodiment, said multispecific antigen binding protein comprises an IL-18 binding domain and an IL-23 binding domain wherein said IL-18 binding domain comprises the following CDRs: CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81 and said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15.

In an embodiment, said multispecific antigen binding protein comprises an IL-18 binding domain and an IL-23 binding domain wherein said IL-18 binding domain comprises the following CDRs: CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO:

81 and said IL-23 binding domain comprises the following CDRs: CDRH1 of SEQ ID NO: 18, CDRH2 of SEQ ID NO: 19, CDRH3 of SEQ ID NO: 20, CDRL1 of SEQ ID NO: 21, CDRL2 of SEQ ID NO: 22 and CDRL3 of SEQ ID NO: 23.

In an embodiment, said multispecific antigen binding protein comprises an IL-18 binding domain and an IL-23 binding domain wherein said IL-18 binding domain comprises the following CDRs: CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81 and said IL-23 binding domain comprises the following CDRs: CDRH1 of SEQ ID NO: 26, CDRH2 of SEQ ID NO: 27, CDRH3 of SEQ ID NO: 28, CDRL1 of SEQ ID NO: 29, CDRL2 of SEQ ID NO: 30 and CDRL3 of SEQ ID NO: 31.

In an embodiment, said multispecific antigen binding protein comprises an IL-18 binding domain and an IL-23 binding domain wherein said IL-18 binding domain comprises the following CDRs: CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81 and said IL-23 binding domain comprises the following CDRs: CDRH1 of SEQ ID NO: 34, CDRH2 of SEQ ID NO: 35, CDRH3 of SEQ ID NO: 36, CDRL1 of SEQ ID NO: 37, CDRL2 of SEQ ID NO: 38 and CDRL3 of SEQ ID NO: 39.

In an embodiment, said multispecific antigen binding protein comprises an IL-18 binding domain and an IL-23 binding domain wherein said IL-18 binding domain comprises the following CDRs: CDRH1 of SEQ ID NO: 76, CDRH2 of SEQ ID NO: 77, CDRH3 of SEQ ID NO: 78, CDRL1 of SEQ ID NO: 79, CDRL2 of SEQ ID NO: 80 and CDRL3 of SEQ ID NO: 81 and said IL-23 binding domain comprises the following CDRs: CDRH1 of SEQ ID NO: 58, CDRH2 of SEQ ID NO: 59, CDRH3 of SEQ ID NO: 60, CDRL1 of SEQ ID NO: 61, CDRL2 of SEQ ID NO: 62 and CDRL3 of SEQ ID NO: 63.

However, in a particular embodiment said multispecific antigen binding protein comprises an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15. In a particular embodiment said multispecific antigen binding protein is a bispecific antibody, thus there is provided a bispecific antibody comprising an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15. In an embodiment there is provided an anti-IL-18 and anti-IL-23 bispecific antibody comprising anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7 and anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15.

In an embodiment, there is provided a multispecific antigen binding protein comprising an IL-18 binding domain and an IL-23 binding domain wherein said IL-18 binding domain comprises:

a. a VH domain comprising a sequence at least 90%, 91%, 92%, 93%, 94%, 95%, 96%, 97%, 98%, 99% or 100% identical to SEQ ID NO: 8 and/or a VL domain comprising a sequence at least 90%, 91%, 92%, 93%, 94%, 95%, 96%, 97%, 98%, 99% or 100% identical to SEQ ID NO: 9;

b. a VH domain comprising a sequence at least 90%, 91%, 92%, 93%, 94%, 95%, 96%, 97%, 98%, 99% or 100% identical to SEQ ID NO: 72 and/or a VL domain comprising a sequence at least 90%, 91%, 92%, 93%, 94%, 95%, 96%, 97%, 98%, 99% or 100% identical to SEQ ID NO: 73; or c. a VH domain comprising a sequence at least 90%, 91%, 92%, 93%, 94%, 95%, 96%, 97%, 98%, 99% or 100% identical to SEQ ID NO: 82 and/or a VL domain comprising a sequence at least 90%, 91%, 92%, 93%, 94%, 95%, 96%, 97%, 98%, 99% or 100% identical to SEQ ID NO: 83.

In an embodiment said multispecific antigen binding protein comprises an IL-18 binding domain and an IL-23 binding domain wherein said IL-23 binding domain comprises:

a. a VH domain comprising a sequence at least 90%, 91%, 92%, 93%, 94%, 95%, 96%, 97%, 98%, 99% or 100% identical to SEQ ID NO: 16 and/or a VL domain comprising a sequence at least 90%, 91%, 92%, 93%, 94%, 95%, 96%, 97%, 98%, 99% or 100% identical to SEQ ID NO: 17;

b. a VH domain comprising a sequence at least 90%, 91%, 92%, 93%, 94%, 95%, 96%, 97%, 98%, 99% or 100% identical to SEQ ID NO: 24 and/or a VL domain comprising a sequence at least 90%, 91%, 92%, 93%, 94%, 95%, 96%, 97%, 98%, 99% or 100% identical to SEQ ID NO: 25;

c. a VH domain comprising a sequence at least 90%, 91%, 92%, 93%, 94%, 95%, 96%, 97%, 98%, 99% or 100% identical to SEQ ID NO: 32 and/or a VL domain comprising a sequence at least 90%, 91%, 92%, 93%, 94%, 95%, 96%, 97%, 98%, 99% or 100% identical to SEQ ID NO: 33;

d. a VH domain comprising a sequence at least 90%, 91%, 92%, 93%, 94%, 95%, 96%, 97%, 98%, 99% or 100% identical to SEQ ID NO: 40 and/or a VL domain comprising a sequence at least 90%, 91%, 92%, 93%, 94%, 95%, 96%, 97%, 98%, 99% or 100% identical to SEQ ID NO: 41; or e. a VH domain comprising a sequence at least 90%, 91%, 92%, 93%, 94%, 95%, 96%, 97%, 98%, 99% or 100% identical to SEQ ID NO: 64 and/or a VL domain comprising a sequence at least 90%, 91%, 92%, 93%, 94%, 95%, 96%, 97%, 98%, 99% or 100% identical to SEQ ID NO: 65.

Provided herein are multispecific antigen binding proteins comprising any combination of the above-mentioned IL-18 binding domains and IL-23 binding domains (as defined by their VH/VL sequences), however in a particular embodiment there is provided a multispecific antigen binding protein comprising an IL-18 binding domain and an IL-23 binding domain, wherein said IL-18 binding domain comprises a VH domain comprising a sequence at least 90%, 91%, 92%, 93%, 94%, 95%, 96%, 97%, 98%, 99% or 100% identical to SEQ ID NO: 8 and a VL domain comprising a sequence at least 90%, 91%, 92%, 93%, 94%, 95%, 96%, 97%, 98%, 99% or 100% identical to SEQ ID NO: 9 and wherein said IL-23 binding domain comprises a VH domain comprising a sequence at least 90%, 91%, 92%, 93%, 94%, 95%, 96%, 97%, 98%, 99% or 100% identical to SEQ ID NO: 16 and a VL domain comprising a sequence at least 90%, 91%, 92%, 93%, 94%, 95%, 96%, 97%, 98%, 99% or 100% identical to SEQ ID NO: 17. In an embodiment there is provided a multispecific antigen binding protein comprising an IL-18 binding domain and an IL-23 binding domain wherein said IL-18 binding domain comprises a VH domain comprising a sequence at least 90% identical or at least 95% identical to SEQ ID NO: 8 and a VL domain comprising a sequence at least 90% identical or at least 95% identical to SEQ ID NO: 9; and wherein said IL-23 binding domain comprises a VH domain comprising a sequence at least 90% identical or at least 95% identical to SEQ ID NO: 16 and a VL domain comprising a sequence at least 90% identical or at least 95% identical to SEQ ID NO: 17.

As well as providing VH and/or VL domain sequences with varying degrees of sequence identity to defined SEQ ID Nos, the VH or VL (or HC or LC) domain sequences disclosed herein may be a variant VH/VL sequence with up to 10 amino acid substitutions, additions, or deletions. For example, the variant sequence may have up to 10, 9, 8, 7, 6, 5, 4, 3, 2 or 1 amino acid substitution(s), addition(s), or deletion(s). The sequence variation (both in terms of percentage identity or in terms of amino acid substitutions, addition or deletion variant) may exclude one or more or all of the CDRs, for example the CDRs are the same as the VH or VL (or HC or LC) sequence and the variation is in the remaining portion of the VH or VL (or HC or LC) sequence, so that the CDR sequences are fixed and intact. In the case of multispecific antigen binding proteins that comprise a constant region, the sequence variation may also exclude sequences that increase binding to FcRn and thus increase half-life of the antigen binding protein, e.g., YTE (M252Y/ S254T/T256E). The sequence variation may also exclude sequences that decrease effector function of the antigen binding protein, e.g., LAGA (L235A and G237A). Typically, the modification is a substitution, particularly a conservative substitution.

In an embodiment said multispecific antigen binding protein comprises an IL-18 binding domain and an IL-23 binding domain wherein said IL-18 binding domain comprises:

a. a VH domain that is a variant of the amino acid sequence set forth in SEQ ID NO: 8 containing 10, 9, 8, 7, 6, 5, 4, 3, 2 or 1 amino acid substitutions, insertions, or deletions and/or a VL domain that is a variant of the amino acid sequence set forth in SEQ ID NO: 9 containing 10, 9, 8, 7, 6, 5, 4, 3, 2 or 1 amino acid substitutions, insertions, or deletions;

b. a VH domain that is a variant of the amino acid sequence set forth in SEQ ID NO: 72 containing 10, 9, 8, 7, 6, 5, 4, 3, 2 or 1 amino acid substitutions, insertions, or deletions and/or a VL domain that is a variant of the amino acid sequence set forth in SEQ ID NO: 73 containing 10, 9, 8, 7, 6, 5, 4, 3, 2 or 1 amino acid substitutions, insertions, or deletions; or c. a VH domain that is a variant of the amino acid sequence set forth in SEQ ID NO: 82 containing 10, 9, 8, 7, 6, 5, 4, 3, 2 or 1 amino acid substitutions, insertions, or deletions and/or a VL domain that is a variant of the amino acid sequence set forth in SEQ ID NO: 83 containing 10, 9, 8, 7, 6, 5, 4, 3, 2 or 1 amino acid substitutions, insertions, or deletions.

In an embodiment said multispecific antigen binding protein comprises an IL-18 binding domain and an IL-23 binding domain wherein said IL-23 binding domain comprises:

a. a VH domain that is a variant of the amino acid sequence set forth in SEQ ID NO: 16 containing 10, 9, 8, 7, 6, 5, 4, 3, 2 or 1 amino acid substitutions, insertions, or deletions and/or a VL domain that is a variant of the amino acid sequence set forth in SEQ ID NO: 17 containing 10, 9, 8, 7, 6, 5, 4, 3, 2 or 1 amino acid substitutions, insertions, or deletions;

b. a VH domain that is a variant of the amino acid sequence set forth in SEQ ID NO: 24 containing 10, 9, 8, 7, 6, 5, 4, 3, 2 or 1 amino acid substitutions, insertions, or deletions and/or a VL domain that is a variant of the amino acid sequence set forth in SEQ ID NO: 25 containing 10, 9, 8, 7, 6, 5, 4, 3, 2 or 1 amino acid substitutions, insertions, or deletions;

c. a VH domain that is a variant of the amino acid sequence set forth in SEQ ID NO: 32 containing 10, 9, 8, 7, 6, 5, 4, 3, 2 or 1 amino acid substitutions, insertions, or deletions and/or a VL domain that is a variant of the amino acid sequence set forth in SEQ ID NO: 33 containing 10, 9, 8, 7, 6, 5, 4, 3, 2 or 1 amino acid substitutions, insertions, or deletions;

d. a VH domain that is a variant of the amino acid sequence set forth in SEQ ID NO: 40 containing 10, 9, 8, 7, 6, 5, 4, 3, 2 or 1 amino acid substitutions, insertions, or deletions and/or a VL domain that is a variant of the amino acid sequence set forth in SEQ ID NO: 41 containing 10, 9, 8, 7, 6, 5, 4, 3, 2 or 1 amino acid substitutions, insertions, or deletions; or e. a VH domain that is a variant of the amino acid sequence set forth in SEQ ID NO: 64 containing 10, 9, 8, 7, 6, 5, 4, 3, 2 or 1 amino acid substitutions, insertions, or deletions and/or a VL domain that is a variant of the amino acid sequence set forth in SEQ ID NO: 65 containing 10, 9, 8, 7, 6, 5, 4, 3, 2 or 1 amino acid substitutions, insertions, or deletions.

However, in a particular embodiment said multispecific antigen binding protein comprises an IL-18 binding domain and an IL-23 binding domain wherein:

i. said IL-18 binding domain comprises a VH domain that is a variant of the amino acid sequence set forth in SEQ ID NO: 8 containing 10, 9, 8, 7, 6, 5, 4, 3, 2 or 1 amino acid substitutions, insertions, or deletions and a VL domain that is a variant of the amino acid sequence set forth in SEQ ID NO: 9 containing 10, 9, 8, 7, 6, 5, 4, 3, 2 or 1 amino acid substitutions, insertions, or deletions; and wherein ii. said IL-23 binding domain comprises a VH domain that is a variant of the amino acid sequence set forth in SEQ ID NO: 16 containing 10, 9, 8, 7, 6, 5, 4, 3, 2 or 1 amino acid substitutions, insertions, or deletions and/or a VL domain that is a variant of the amino acid sequence set forth in SEQ ID NO: 17 containing 10, 9, 8, 7, 6, 5, 4, 3, 2 or 1 amino acid substitutions, insertions, or deletions.

In an embodiment said multispecific antigen binding protein comprises an IL-18 binding domain and an IL-23 binding domain wherein said IL-18 binding domain comprises:

a. a VH domain of SEQ ID NO: 8 and a VL domain of SEQ ID NO: 9;

b. a VH domain of SEQ ID NO: 72 and a VL domain of SEQ ID NO: 73; or c. a VH domain of SEQ ID NO: 82 and a VL domain of SEQ ID NO: 83.

In an embodiment said multispecific antigen binding protein comprises an IL-18 binding domain and an IL-23 binding domain wherein said IL-23 binding domain comprises:

a. a VH domain of SEQ ID NO: 16 and a VL domain of SEQ ID NO: 17;

b. a VH domain of SEQ ID NO: 24 and a VL domain of SEQ ID NO: 25;

c. a VH domain of SEQ ID NO: 32 and a VL domain of SEQ ID NO: 33;

d. a VH domain of SEQ ID NO: 40 and a VL domain of SEQ ID NO: 41; or e. a VH domain of SEQ ID NO: 64 and a VL domain of SEQ ID NO: 65.

Provided herein are multispecific antigen binding proteins comprising any combination of the above-mentioned IL-18 binding domains and IL-23 binding domains (as defined by their VH/VL sequences), each combination being provided below as follows:

In an embodiment, said multispecific antigen binding protein comprises an IL-18 binding domain and an IL-23 binding domain wherein said IL-18 binding domain comprises a VH domain of SEQ ID NO: 8 and a VL domain of SEQ ID NO: 9 and said IL-23 binding domain comprises a VH domain of SEQ ID NO: 16 and a VL domain of SEQ ID NO: 17.

In an embodiment, said multispecific antigen binding protein comprises an IL-18 binding domain and an IL-23 binding domain wherein said IL-18 binding domain comprises a VH domain of SEQ ID NO: 8 and a VL domain of SEQ ID NO: 9 and said IL-23 binding domain comprises a VH domain of SEQ ID NO: 24 and a VL domain of SEQ ID NO: 25.

In an embodiment, said multispecific antigen binding protein comprises an IL-18 binding domain and an IL-23 binding domain wherein said IL-18 binding domain comprises a VH domain of SEQ ID NO: 8 and a VL domain of SEQ ID NO: 9 and said IL-23 binding domain comprises a VH domain of SEQ ID NO: 32 and a VL domain of SEQ ID NO: 33.

In an embodiment, said multispecific antigen binding protein comprises an IL-18 binding domain and an IL-23 binding domain wherein said IL-18 binding domain comprises a VH domain of SEQ ID NO: 8 and a VL domain of SEQ ID NO: 9 and said IL-23 binding domain comprises a VH domain of SEQ ID NO: 40 and a VL domain of SEQ ID NO: 41.

In an embodiment, said multispecific antigen binding protein comprises an IL-18 binding domain and an IL-23 binding domain wherein said IL-18 binding domain comprises a VH domain of SEQ ID NO: 8 and a VL domain of SEQ ID NO: 9 and said IL-23 binding domain comprises a VH domain of SEQ ID NO: 64 and a VL domain of SEQ ID NO: 65.

In an embodiment, said multispecific antigen binding protein comprises an IL-18 binding domain and an IL-23 binding domain wherein said IL-18 binding domain comprises a VH domain of SEQ ID NO: 72 and a VL domain of SEQ ID NO: 73 and said IL-23 binding domain comprises a VH domain of SEQ ID NO: 16 and a VL domain of SEQ ID NO: 17.

In an embodiment, said multispecific antigen binding protein comprises an IL-18 binding domain and an IL-23 binding domain wherein said IL-18 binding domain comprises a VH domain of SEQ ID NO: 72 and a VL domain of SEQ ID NO: 73 and said IL-23 binding domain comprises a VH domain of SEQ ID NO: 24 and a VL domain of SEQ ID NO: 25.

In an embodiment, said multispecific antigen binding protein comprises an IL-18 binding domain and an IL-23 binding domain wherein said IL-18 binding domain comprises a VH domain of SEQ ID NO: 72 and a VL domain of SEQ ID NO: 73 and said IL-23 binding domain comprises a VH domain of SEQ ID NO: 32 and a VL domain of SEQ ID NO: 33.

In an embodiment, said multispecific antigen binding protein comprises an IL-18 binding domain and an IL-23 binding domain wherein said IL-18 binding domain comprises a VH domain of SEQ ID NO: 72 and a VL domain of SEQ ID NO: 73 and said IL-23 binding domain comprises a VH domain of SEQ ID NO: 40 and a VL domain of SEQ ID NO: 41.

In an embodiment, said multispecific antigen binding protein comprises an IL-18 binding domain and an IL-23 binding domain wherein said IL-18 binding domain comprises a VH domain of SEQ ID NO: 72 and a VL domain of SEQ ID NO: 73 and said IL-23 binding domain comprises a VH domain of SEQ ID NO: 64 and a VL domain of SEQ ID NO: 65.

In an embodiment, said multispecific antigen binding protein comprises an IL-18 binding domain and an IL-23 binding domain wherein said IL-18 binding domain comprises a VH domain of SEQ ID NO: 82 and a VL domain of SEQ ID NO: 83 and said IL-23 binding domain comprises a VH domain of SEQ ID NO: 16 and a VL domain of SEQ ID NO: 17.

In an embodiment, said multispecific antigen binding protein comprises an IL-18 binding domain and an IL-23 binding domain wherein said IL-18 binding domain comprises a VH domain of SEQ ID NO: 82 and a VL domain of SEQ ID NO: 83 and said IL-23 binding domain comprises a VH domain of SEQ ID NO: 24 and a VL domain of SEQ ID NO: 25.

In an embodiment, said multispecific antigen binding protein comprises an IL-18 binding domain and an IL-23 binding domain wherein said IL-18 binding domain comprises a VH domain of SEQ ID NO: 82 and a VL domain of SEQ ID NO: 83 and said IL-23 binding domain comprises a VH domain of SEQ ID NO: 32 and a VL domain of SEQ ID NO: 33.

In an embodiment, said multispecific antigen binding protein comprises an IL-18 binding domain and an IL-23 binding domain wherein said IL-18 binding domain comprises a VH domain of SEQ ID NO: 82 and a VL domain of SEQ ID NO: 83 and said IL-23 binding domain comprises a VH domain of SEQ ID NO: 40 and a VL domain of SEQ ID NO: 41.

In an embodiment, said multispecific antigen binding protein comprises an IL-18 binding domain and an IL-23 binding domain wherein said IL-18 binding domain comprises a VH domain of SEQ ID NO: 82 and a VL domain of SEQ ID NO: 83 and said IL-23 binding domain comprises a VH domain of SEQ ID NO: 64 and a VL domain of SEQ ID NO: 65.

However, in a particular embodiment said multispecific antigen binding protein comprises an IL-18 binding domain and an IL-23 binding domain wherein said IL-18 binding domain comprises a VH domain of SEQ ID NO: 8 and a VL domain of SEQ ID NO: 9; and said IL-23 binding domain comprises a VH domain of SEQ ID NO: 16 and a VL domain of SEQ ID NO: 17. In an embodiment said multispecific antigen binding protein is a bispecific antibody, thus there is provided a bispecific antibody comprising an IL-18 binding domain and an IL-23 binding domain wherein said IL-18 binding domain comprises a VH domain of SEQ ID NO: 8 and a VL domain of SEQ ID NO: 9; and said IL-23 binding domain comprises a VH domain of SEQ ID NO: 16 and a VL domain of SEQ ID NO: 17. In an embodiment, there is provided an anti-IL-18 and anti-IL-23 bispecific antibody wherein said anti-IL-18 comprises a VH domain of SEQ ID NO: 8 and a VL domain of SEQ ID NO: 9 and wherein said anti-IL-23 comprises a VH domain of SEQ ID NO: 16 and a VL domain of SEQ ID NO: 17.

In an embodiment, the multispecific antigen binding proteins disclosed herein are bispecific antigen binding proteins.

In an embodiment, the multispecific antigen binding proteins disclosed herein are bispecific antibodies. In an embodiment, the bispecific antibody is selected from the group consisting of: duobody, L-body, common light chain antibody, an antibody with a modified cysteine bridging between the heavy and light chains, a chimeric heavy/light chain antibody, cross-mab, mAb pair, and Het-mAb. However, in a particular embodiment, the multispecific antigen binding proteins disclosed herein are bispecific antibodies are Het-mAbs.

As previously described Het-mAbs are IgG-like molecules that target two different epitopes, in the present case, said epitopes being on two different targets: IL-18 and IL-23. A "Het-mAb" is an example of a bispecific antibody. Het-mAb's have four distinct chains: two non-identical heavy chains (in the present case one anti-IL-18 heavy chain and one anti-IL-23 heavy chain) and two non-identical light chains (in the present case one anti-IL-18 light chain and one anti-IL-23 light chain). These chains contain a set of mutations in the Fc portion of the molecule that drive heavy chain dimerization, optionally wherein a first heavy chain contains the mutations T350V, L351Y, F405A, Y407V and a second heavy chain contains the mutations T350V, T366L, K392L, T394W (EU Index Numbering). Other suitable mutations for driving heavy chain dimerization are disclosed in WO2012/058768 and WO2013/063702. These chains further contain a set of mutations on the Fab portion that drive correct heavy/light chain pairing, e.g., kappa/kappa or lambda/kappa subtype bispecific mAbs. Suitable mutations for driving heavy/light chain pairing are disclosed in WO2014/082179, WO2015/181805, and WO2017/059551.

Classification and formats of bispecific antibodies are comprehensively described in reviews by Labrijn et al 2019 and Brinkmann and Kontermann 2017. Bispecifics may be generally classified as having a symmetric or asymmetric architecture. Bispecifics may have an Fc or may be fragment-based (lacking an Fc). Fragment based bispecifics combine multiple antigen-binding antibody fragments in one molecule without an Fc region e.g., Fab-scFv, Fab-scFv2, orthoganol Fab-Fab, Fab-Fv, tandem scFc (e.g., BiTE and BiKE molecules), Diabody, DART, TandAb, scDiabody, tandem dAb etc.

Symmetric formats combine multiple binding specificities in a single polypeptide chain or single HC/LC pair including Fc-fusion proteins of fragment-based formats and formats whereby antibody fragments are fused to regular antibody molecules. Examples of symmetric formats may include DVD-Ig, TVD-Ig, CODV-Ig, $(scFv)_4$-Fc, IgG-$(scFv)_2$, Tetravalent DART-Fc, $F(ab)_4$CrossMab, IgG-HC-scFv, IgG-LC-scFv, mAb-dAb etc.

Asymmetric formats retain as closely as possible the native architecture of natural antibodies by forcing correct HL chain pairing and/or promoting H chain heterodimerization during the co-expression of three (if common heavy or light chains are used) or four polypeptide chains e.g., Triomab, asymmetric reengineering technology immunoglobulin (ART-Ig), CrossMab, Biclonics common light chain, ZW1 common light chain, DuoBody and knobs into holes (KiH), DuetMab, κλ body, Xmab, YBODY, Het-mAb, HET-Fab, DART-Fc, SEEDbody, mouse/rat chimeric IgG.

The multispecific antigen binding proteins of the disclosure may comprise an alternative antibody format. Alternative antibody formats include alternative scaffolds in which one or more CDRs are arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain.

Bispecific formats also include an antibody fused to a non-Ig scaffold such as Affimabs, Fynomabs, Zybodies, and Anticalin-IgG fusions, ImmTAC.

Multispecific antigen binding proteins (e.g., bispecific antigen binding proteins) and bispecific antibodies of the disclosure may be derived from rat, mouse, primate (e.g., cynomolgus, Old World monkey or Great Ape) or human. In an embodiment, the multispecific antigen binding proteins (e.g., bispecific antigen binding proteins) or bispecific antibody of the disclosure is derived from a human, humanized or chimeric antibody. The multispecific antigen binding protein (e.g., bispecific antigen binding protein) may comprise a constant region, which may be of any isotype or subclass. The constant region of the multispecific antigen binding protein (e.g., bispecific antigen binding protein) or bispecific antibody may be of the IgG isotype, for example IgG1, IgG2, IgG3, IgG4 or variants thereof. In an embodiment, the multispecific antigen binding protein (e.g., bispecific antigen binding protein) or bispecific antibody comprises an IgG1 constant region. In an embodiment, the bispecific antibody is an IgG1 antibody.

In an embodiment, the multispecific antigen binding protein (e.g., bispecific antigen binding protein) or bispecific antibody comprises an IgG1K constant region. In an embodiment, the bispecific antibody is an IgG1κ antibody.

In an embodiment, the multispecific antigen binding protein (e.g., bispecific antigen binding protein) or the bispecific antibody is a disulfide-linked α2β2 tetramer. In an embodiment, the multispecific antigen binding protein (e.g., bispecific antigen binding protein) or bispecific antibody comprises two light (kappa, κ) and two heavy (IgG1) chains.

Fully human antibodies can be obtained using a variety of methods, for example using yeast-based libraries or transgenic animals (e.g., mice) that can produce repertoires of human antibodies. Yeast presenting human antibodies on their surface that bind to an antigen of interest can be selected using FACS (Fluorescence-Activated Cell Sorting) based methods or by capture on beads using labelled antigens. Transgenic animals that have been modified to express human immunoglobulin genes can be immunized with an antigen of interest and antigen-specific human antibodies isolated using B-cell sorting techniques. Human antibodies produced using these techniques can then be characterized for desired properties such as affinity, developability and selectivity.

As previously described, in a preferred embodiment the multispecific antigen binding proteins disclosed herein are bispecific antibodies. In an embodiment the multispecific antigen binding proteins or bispecific antibodies disclosed herein comprise an Fc domain (alternatively, Fc region). In an embodiment, said Fc domain is engineered.

Fc engineering methods can be applied to modify the functional or pharmacokinetics properties of a multispecific antigen binding protein (e.g., bispecific antigen binding protein) or bispecific antibody of the disclosure. Effector function may be altered by making mutations in the Fc region that increase or decrease binding to C1q or Fcγ receptors and modify CDC or ADCC activity respectively. Modifications to the glycosylation pattern of an antibody can also be made to change the effector function. The in vivo half-life of an antibody can be altered by making mutations that affect binding of the Fc to the FcRn (Neonatal Fc Receptor).

The interaction between the Fc region of an antigen binding protein or antibody and various Fc receptors (FcR), including FcγRI (CD64), FcγRII (CD32), FcγRIII (CD16), FcRn, C1q, and type II Fc receptors is believed to mediate the effector functions of the antigen binding protein or antibody. Significant biological effects can be a consequence of effector functionality. Effector function can be assessed in a number of ways including, for example, evaluating ADCC effector function of antibody coated to target cells mediated by Natural Killer (NK) cells via FcγRIII, or monocytes/macrophages via FcγRI, or evaluating CDC effector function of antibody coated to target cells mediated by complement cascade via C1q. Examples of ADCC assays can be found in Shields et al, 2001, The Journal of Biological Chemistry, Vol. 276, p. 6591-6604; Chappel et al, 1993, The Journal of Biological Chemistry, Vol 268, p. 25124-25131; Lazar et al, 2006, PNAS, 103; 4005-4010. Examples of assays to determine CDC function include those described in J Imm Meth, 1995, 184: 29-38.

The effects of mutations on effector functions (e.g., FcRn binding, FcγRs and C1q binding, CDC, ADCML, ADCC, ADCP) can be assessed, e.g., as described in Grevys et al., J Immunol. 2015 Jun. 1; 194(11): 5497-5508, or Tam et al., Antibodies 2017, 6(3); Monnet et al., 2014 mAbs, 6:2, 422-436.

Throughout this disclosure, amino acid residues in Fc regions are numbered according to the EU index numbering convention (unless otherwise mentioned).

Some isotypes of human constant regions, in particular IgG4 and IgG2 isotypes, essentially lack the functions of a) activation of complement by the classical pathway; and b) ADCC. Various modifications to the heavy chain constant region of multispecific antigen binding proteins may be carried out to alter effector function depending on the desired effector property. IgG1 constant regions containing specific mutations that reduce binding to Fc receptors and reduce an effector function, such as ADCC and CDC, have been described (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168).

In one embodiment the multispecific antigen binding proteins (e.g., bispecific antigen binding proteins) or bispecific antibodies of the present disclosure comprise a constant region such that the multispecific antigen binding protein (e.g., bispecific antigen binding protein) or bispecific antibody has reduced effector function, for example such as reduced ADCC and/or CDC. In one such embodiment, the heavy chain constant region may comprise a naturally disabled constant region of an IgG2 or IgG4 isotype or a mutated IgG1 constant region. Examples of suitable modifications are described in EP0307434. One example comprises substitution with alanine at positions 235 and 237 (EU index numbering), i.e., L235A and G237A (commonly referred to as "LAGA" mutations). Another example comprises substitution with alanine at positions 234 and 235 (EU index numbering), i.e., L234A and L235A (commonly referred to as "LALA" mutations). Further examples, described in EP2691417 and U.S. Pat. No. 8,969,526, comprise P329G or P329R, in combination with the LALA mutations (EU index numbering) for IgG1 Fcs and P329G or P329R in combination with S228P and L235E for IgG4 Fcs (EU index numbering). In a particular embodiment the multispecific antigen binding proteins (or bispecific antibodies) disclosed herein comprise an Fc domain and wherein said Fc domain comprises the amino acid substitutions L235A and G237A (EU index numbering).

Additional alterations and mutations to decrease effector function include: (with reference to IgG1 unless otherwise noted): aglycosylated N297A or N297Q or N297G; L235E; IgG4:F234A/L235A; and chimeric IgG2/IgG4. IgG2: H268Q/V309L/A330S/P331S, and IgG2: V234A/G237A/P238S/H268A/V309L/A330S/P331S can reduce FcγR and C1q binding (Wang et al. 2018 and U.S. Pat. No. 8,961,967).

Other mutations that decrease effector function include L234F/L235E/P331S; a chimeric antibody created using the CH1 and hinge region from human IgG2 and the CH2 and CH3 regions from human IgG4; IgG2m4, based on the IgG2 isotype with four key amino acid residue changes derived from IgG4 (H268Q, V309L, A330S and P331S); IgG26 that contains V234A/G237A/P238S/H268A/V309L/A330S/P331S substitutions to eliminate affinity for Fcγ receptors and C1q complement protein; IgG2m4 (H268Q/V309L/A330S/P331S, changes to IgG4); IgG4 (S228P/L234A/L235A); huIgG1 L234A/L235A (AA); huIgG4 S228P/L234A/L235A; IgG1 (L234A/L235A/G237A/P238S/H268A/A330S/P331S); IgG461 (S228P/F234A/L235A/G237A/P238S); and IgG462 (S228P/F234A/L235A/ΔG236/G237A/P238S, wherein Δ denotes a deletion) (Tam et al., Antibodies 2017, 6(3)).

The long half-life of IgG antibodies is reported to be dependent on their binding to FcRn. Therefore, substitutions that increase the binding affinity of IgG to FcRn at pH 6.0 while maintaining the pH dependence of the interaction with target, by engineering the constant region, have been extensively studied (Ghetie et al., Nature Biotech. 15: 637-640, 1997; Hinton et al., JBC 279: 6213-6216, 2004; Dall'Acqua et al., 10 J Immunol 117: 1129-1138, 2006). The in vivo half-life of multispecific antigen binding proteins or bispecific antibodies of the present disclosure may be altered by modification of a heavy chain constant domain or an FcRn binding domain therein.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells and, if they bind to FcRn, are recycled out of the cells back into circulation. In contrast, IgG molecules that enter the cells and do not bind to FcRn and are targeted to the lysosomal pathway where they are degraded.

FcRn is believed to be involved in both antibody clearance and the transcytosis across tissues (see Junghans R. P (1997) Immunol. Res 16. 29-57 and Ghetie et al (2000)

Annu. Rev. Immunol. 18, 739-766). Human IgG1 residues determined to interact directly with human FcRn include Ile253, Ser254, Lys288, Thr307, Gln311, Asn434 and His435. Mutations at any of these positions may enable increased serum half-life and/or altered effector properties of multispecific antigen binding proteins of the disclosure.

Multispecific antigen binding proteins (e.g., bispecific antigen binding proteins) and bispecific antibodies of the present disclosure may have amino acid modifications that increase the affinity of the constant domain or fragment thereof for FcRn. Increasing the half-life (i.e., serum half-life) of therapeutic and diagnostic IgG antibodies and other bioactive molecules has many benefits including reducing the amount and/or frequency of dosing of these molecules.

Thus, in an embodiment, a multispecific antigen binding protein or bispecific antibody of the disclosure comprises a half-life extending mutation or set of mutations. In one embodiment, a multispecific antigen binding protein or bispecific antibody of the disclosure comprises all or a portion (an FcRn binding portion) of an IgG constant domain having one or more of the following amino acid modifications.

For example, with reference to IgG1, M252Y/S254T/T256E (commonly referred to as "YTE" mutations) and M428L/N434S (commonly referred to as "LS" mutations) increase FcRn binding at pH 6.0 (Wang et al. 2018). In a particular embodiment, the multispecific antigen binding protein or bispecific antibody of the disclosure comprises YTE (M252Y/S254T/T256E). In an embodiment, the multispecific antigen binding protein or bispecific antibody of the disclosure comprises an Fc domain wherein said Fc domain comprises M252Y/S254T/T256E. In an embodiment, a multispecific antigen binding protein or bispecific antibody of the disclosure comprises LS (M428L/N434S). In an embodiment, a multispecific antigen binding protein or bispecific antibody of the disclosure comprises DHS (L309D/Q311H/N434S).

The multispecific antigen binding proteins disclosed herein may therefore comprise a heavy chain Fc domain (e.g., an IgG1 Fc) comprising a tyrosine residue at position 252, a threonine residue at position 254 and a glutamic acid residue at position 256. The multispecific antigen binding protein may comprise a human IgG1 Fc domain comprising a tyrosine residue at position 252, a threonine residue at position 254 and a glutamic acid residue at position 256. The numbering of the amino acids in the heavy chain Fc domain (i.e., a tyrosine residue at position 252, a threonine residue at position 254 and a glutamic acid residue at position 256) was derived using EU numbering, as described in: Edelman et al. (1969) Proc. Natl. Acad. USA, 63: 78-85 [PMID: 5257969].

Half-life can also be enhanced by T250Q/M428L, V259I/V308F/M428L, N434A, and T307A/E380A/N434A mutations (with reference to IgG1 and Kabat numbering) (Monnet et al.). Half-life and FcRn binding can also be extended by introducing H433K and N434F mutations (commonly referred to as "HN" or "NHance" mutations) (with reference to IgG1) (WO2006/130834). In an embodiment, a multispecific antigen binding protein or bispecific antibody of the disclosure comprises H433K and N434F. WO00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386,388, 400, 413, 415, 424, 433, 434, 435, 436, 439, and 447 of the Fc region (EU index numbering).

WO02/060919 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435.

Shields et al. (2001, J Biol Chem; 276:6591-604) used alanine scanning mutagenesis to alter residues in the Fc region of a human IgG1 antibody and then assessed the binding to human FcRn. Positions that effectively abrogated binding to FcRn when changed to alanine include I253, S254, H435, and Y436. Other positions showed a less pronounced reduction in binding as follows: E233-G236, R255, K288, L309, S415, and H433. Several amino acid positions exhibited an improvement in FcRn binding when changed to alanine; notable among these are P238, T256, E272, V305, T307, Q311, D312, K317, D376, E380, E382, S424, and N434. Many other amino acid positions exhibited a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

The most pronounced effect with respect to improved FcRn binding was found for combination variants. At pH 6.0, the E380A/N434A variant showed over 8-fold better binding to FcRn, relative to native IgG1, compared with 2-fold for E380A and 3.5-fold for N434A. Adding T307A to this resulted in a 12-fold improvement in binding relative to native IgG1. In one embodiment the multispecific antigen binding protein or bispecific antibody of the disclosure comprises the E380A/N434A mutations and has increased binding to FcRn.

Dall'Acqua et al. (2002, J Immunol.; 169:5171-80) describes random mutagenesis and screening of human IgG1 hinge-Fc fragment phage display libraries against mouse FcRn. They disclosed random mutagenesis of positions 251, 252, 254-256, 308, 309, 311, 312, 314, 385-387, 389, 428, 433, 434, and 436. The major improvements in IgG1-human FcRn complex stability occur when substituting residues located in a band across the Fc-FcRn interface (M252, S254, T256, H433, N434, and Y436) and to lesser extent substitutions of residues at the periphery, such as V308, L309, Q311, G385, Q386, P387, and N389. The variant with the highest affinity to human FcRn was obtained by combining the M252Y/S254T/T256E ("YTE") and H433K/N434F/Y436H mutations and exhibited a 57-fold increase in affinity relative to the wild-type IgG1. The in vivo behavior of such a mutated human IgG1 exhibited a nearly 4-fold increase in serum half-life in cynomolgus monkey as compared to wild-type IgG1.

The present disclosure therefore provides a multispecific antigen binding protein, in particular a bispecific antibody, with optimized binding to FcRn. In an embodiment, the multispecific antigen binding protein comprises at least one amino acid modification in the Fc domain of said multispecific antigen binding protein, wherein said modification is at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc domain.

Additionally, various publications describe methods for obtaining physiologically active molecules with modified half-lives, either by introducing an FcRn-binding polypeptide into the molecules (WO97/43316, U.S. Pat. Nos. 5,869, 046, 5,747,035, WO96/32478 and WO91/14438) or by fusing the molecules with antibodies whose FcRn-binding affinities are preserved, but affinities for other Fc receptors have been greatly reduced (WO99/43713) or fusing with FcRn binding domains of antibodies (WO00/09560, U.S. Pat. No. 4,703,039).

FcRn affinity enhanced Fc variants to improve both antibody cytotoxicity and half-life were identified in screens at pH 6.0. The selected IgG variants can be produced as low fucosylated molecules. The resulting variants show increased serum persistence in hFcRn mice, as well as conserved enhanced ADCC (Monnet et al.) Exemplary variants include (with reference to IgG1 and Kabat numbering): P230T/V303A/K322R/N389T/F404L/N434S; P228R/N434S; Q311R/K334R/Q342E/N434Y; C226G/Q386R/N434Y; T307P/N389T/N434Y; P230S/N434S; P230T/V305A/T307A/A378V/L398P/N434S; P230T/P387S/N434S; P230Q/E269D/N434S; N276S/A378V/N434S; T307A/N315D/A330V/382V/N389T/N434Y; T256N/A378V/S383N/N434Y; N315D/A330V/N361D/A387V/N434Y; V259I/N315D/M428L/N434Y; P230S/N315D/M428L/N434Y; F241L/V264E/T307P/A378V/H433R; T250A/N389K/N434Y; V305A/N315D/A330V/P395A/N434Y; V264E/Q386R/P396L/N434S/K439R; E294del/T307P/N434Y (wherein 'del' indicates a deletion).

In an embodiment there is provided a multispecific antigen binding protein comprising an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15 and wherein said multispecific antigen binding protein comprises an Fc domain, said Fc domain comprising amino acid modifications that reduce effector function compared to an Fc domain without said modifications. In an embodiment there is provided a multispecific antigen binding protein comprising an IL-18 binding domain and an IL-23 binding domain wherein said IL-18 binding domain comprises a VH domain of SEQ ID NO: 8 and a VL domain of SEQ ID NO: 9; and said IL-23 binding domain comprises a VH domain of SEQ ID NO: 16 and a VL domain of SEQ ID NO: 17 and wherein said multispecific antigen binding protein comprises a Fc domain, said Fc domain comprising amino acid modifications that reduce effector function compared to an Fc domain without said modifications.

In an embodiment there is provided a multispecific antigen binding protein comprising an IL-18 binding domain and an IL-23 binding domain wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15 and wherein said multispecific antigen binding protein comprises an Fc domain, said Fc domain comprising amino acid modifications that increase the half life of the multispecific antigen binding protein compared to an Fc domain without said modifications, optionally wherein said modifications are M252Y/S254T/T256E. In an embodiment there is provided a multispecific antigen binding protein comprising an IL-18 binding domain and an IL-23 binding domain wherein said IL-18 binding domain comprises a VH domain of SEQ ID NO: 8 and a VL domain of SEQ ID NO: 9; and said IL-23 binding domain comprises a VH domain of SEQ ID NO: 16 and a VL domain of SEQ ID NO: 17 and wherein said multispecific antigen binding protein comprises an Fc domain, said Fc domain comprising amino acid modifications that increase the half life of the multispecific antigen binding protein compared to an Fc domain without said modifications, optionally wherein said modifications are M252Y/S254T/T256E.

The present disclosure provides multispecific antigen binding proteins, in particular bispecific antibodies, that bind (or are capable of binding) to IL-18 and IL-23. In an embodiment said multispecific antigen binding protein or bispecific antibody comprises an IL-18 binding domain and an IL-23 binding domain wherein said IL-18 binding domain comprises a heavy chain and a light chain and wherein said IL-23 binding domain comprises a heavy chain and a light chain.

In an embodiment said multispecific antigen binding protein or bispecific antibody comprises an IL-18 binding domain and an IL-23 binding domain wherein said IL-18 binding domain comprises:

a heavy chain having 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID NOs: 42, 47, 50 or 55; and a light chain having 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID Nos: 44, 49, 52 or 57.

In an embodiment said multispecific antigen binding protein or bispecific antibody comprises an IL-18 binding domain and an IL-23 binding domain wherein said IL-18 binding domain comprises:

a heavy chain wherein said heavy chain is a variant of the amino acid sequence set forth in any of SEQ ID NOs: 42, 47, 50 or 55 that contains 10, 9, 8, 7, 6, 5, 4, 3, 2 or 1 amino acid substitutions, insertions, or deletions; and a light chain wherein said light chain is a variant of the amino acid sequence set forth in any of SEQ ID Nos: 44, 49, 52 or 57 that contains that contains 10, 9, 8, 7, 6, 5, 4, 3, 2 or 1 amino acid substitutions, insertions, or deletions.

In an embodiment said multispecific antigen binding protein or bispecific antibody comprises an IL-18 binding domain and an IL-23 binding domain wherein said IL-18 binding domain comprises:

a heavy chain comprising any of SEQ ID NOs: 42, 47, 50 or 55; and a light chain comprising any of SEQ ID Nos: 44, 49, 52 or 57.

In an embodiment said multispecific antigen binding protein or bispecific antibody comprises an IL-18 binding domain and an IL-23 binding domain wherein said IL-23 binding domain comprises:

a heavy chain having 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID NOs: 43, 46, 51 or 54; and a light chain having 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID Nos: 45, 48, 53 or 56.

In an embodiment said multispecific antigen binding protein or bispecific antibody comprises an IL-18 binding domain and an IL-23 binding domain wherein said IL-23 binding domain comprises:

a heavy chain wherein said heavy chain is a variant of the amino acid sequence set forth in any of SEQ ID NOs: 43, 46, 51 or 54 that contains 10, 9, 8, 7, 6, 5, 4, 3, 2 or 1 amino acid substitutions, insertions, or deletions; and a light chain wherein said light chain is a variant of the amino acid sequence set forth in any of SEQ ID Nos: 45, 48, 53 or 56 that contains that contains 10, 9, 8, 7, 6, 5, 4, 3, 2 or 1 amino acid substitutions, insertions, or deletions.

In an embodiment said multispecific antigen binding protein or bispecific antibody comprises an IL-18 binding domain and an IL-23 binding domain wherein said IL-23 binding domain comprises:

a heavy chain comprising any of SEQ ID NOs: 43, 46, 51 or 54; and a light chain comprising any of SEQ ID Nos: 45, 48, 53 or 56.

In an embodiment said multispecific antigen binding protein or bispecific antibody comprises an IL-18 binding domain and an IL-23 binding domain wherein said IL-18 binding domain comprises a heavy chain (IL-18-HC) and a light chain (IL-18-LC) and wherein said IL-23 binding domain comprises a heavy chain (IL-23-HC) and a light chain (IL-23-LC), wherein:

said IL-18-HC has 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID NOs: 42, 47, 50 or 55;

said IL-18-LC has 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID Nos: 44, 49, 52 or 57;

said IL-23-HC has 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID NOs: 43, 46, 51 or 54; and said IL-23-LC has 90% or greater, 91% or greater, 92% or greater, 93% or greater, 94% or greater, 95% or greater, 96% or greater, 97% or greater, 98% or greater, 99% or greater or 100% identity to the amino acid sequence set forth in any of SEQ ID Nos: 45, 48, 53 or 56.

In an embodiment said multispecific antigen binding protein or bispecific antibody comprises an IL-18 binding domain and an IL-23 binding domain wherein said IL-18 binding domain comprises a heavy chain (IL-18-HC) and a light chain (IL-18-LC) and wherein said IL-23 binding domain comprises a heavy chain (IL-23-HC) and a light chain (IL-23-LC), wherein:

said IL-18-HC is a variant of the amino acid sequence set forth in any of SEQ ID NOs: 42, 47, 50 or 55 that contains 10, 9, 8, 7, 6, 5, 4, 3, 2 or 1 amino acid substitutions, insertions, or deletions;

said IL-18-LC is a variant of the amino acid sequence set forth in any of SEQ ID Nos: 44, 49, 52 or 57 that contains that contains 10, 9, 8, 7, 6, 5, 4, 3, 2 or 1 amino acid substitutions, insertions, or deletions;

said IL-23-HC is a variant of the amino acid sequence set forth in any of SEQ ID NOs: 43, 46, 51 or 54 that contains 10, 9, 8, 7, 6, 5, 4, 3, 2 or 1 amino acid substitutions, insertions, or deletions; and said IL-23-LC is a variant of the amino acid sequence set forth in any of SEQ ID Nos: 45, 48, 53 or 56 that contains that contains 10, 9, 8, 7, 6, 5, 4, 3, 2 or 1 amino acid substitutions, insertions, or deletions.

In an embodiment said multispecific antigen binding protein or bispecific antibody comprises an IL-18 binding domain and an IL-23 binding domain wherein said IL-18 binding domain comprises a heavy chain (IL-18-HC) and a light chain (IL-18-LC) and wherein said IL-23 binding domain comprises a heavy chain (IL-23-HC) and a light chain (IL-23-LC), wherein:

said IL-18-HC comprises any of SEQ ID NOs: 42, 47, 50 or 55;

said IL-18-LC comprises any of SEQ ID Nos: 44, 49, 52 or 57;

said IL-23-HC comprises any of SEQ ID NOs: 43, 46, 51 or 54; and said IL-23-LC comprises any of SEQ ID Nos: 45, 48, 53 or 56.

In an embodiment, the multispecific antigen binding protein or bispecific antibody of the present disclosure comprises two heavy chains and two light chains. Thus, in an embodiment there is provided a multispecific antigen binding protein or bispecific antibody comprising an IL-18 binding domain and an IL-23 binding domain wherein said multispecific antigen binding protein or bispecific antibody comprises:

a. a heavy chain comprising a sequence at least 90%, 91%, 92%, 93%, 94%, 95%, 96%, 97%, 98%, 99% or 100% identical to SEQ ID NO:42, a light chain comprising a sequence at least 90%, 91%, 92%, 93%, 94%, 95%, 96%, 97%, 98%, 99% or 100% identical to SEQ ID NO: 44, a heavy chain comprising a sequence at least 90%, 91%, 92%, 93%, 94%, 95%, 96%, 97%, 98%, 99% or 100% identical to SEQ ID NO: 43, and a light chain comprising a sequence at least 90%, 91%, 92%, 93%, 94%, 95%, 96%, 97%, 98%, 99% or 100% identical to SEQ ID NO:45;

b. a heavy chain comprising a sequence at least 90%, 91%, 92%, 93%, 94%, 95%, 96%, 97%, 98%, 99% or 100% identical to SEQ ID NO:47, a light chain comprising a sequence at least 90%, 91%, 92%, 93%, 94%, 95%, 96%, 97%, 98%, 99% or 100% identical to SEQ ID NO: 49, a heavy chain comprising a sequence at least 90%, 91%, 92%, 93%, 94%, 95%, 96%, 97%, 98%, 99% or 100% identical to SEQ ID NO: 46, and a light chain comprising a sequence at least 90%, 91%, 92%, 93%, 94%, 95%, 96%, 97%, 98%, 99% or 100% identical to SEQ ID NO:48;

c. a heavy chain comprising a sequence at least 90%, 91%, 92%, 93%, 94%, 95%, 96%, 97%, 98%, 99% or 100% identical to SEQ ID NO:50, a light chain comprising a sequence at least 90%, 91%, 92%, 93%, 94%, 95%, 96%, 97%, 98%, 99% or 100% identical to SEQ ID NO: 52, a heavy chain comprising a sequence at least 90%, 91%, 92%, 93%, 94%, 95%, 96%, 97%, 98%, 99% or 100% identical to SEQ ID NO: 51, and a light chain comprising a sequence at least 90%, 91%, 92%, 93%, 94%, 95%, 96%, 97%, 98%, 99% or 100% identical to SEQ ID NO:53; or d. a heavy chain comprising a sequence at least 90%, 91%, 92%, 93%, 94%, 95%, 96%, 97%, 98%, 99% or 100% identical to SEQ ID NO: 54, a light chain comprising a sequence at least 90%, 91%, 92%, 93%, 94%, 95%, 96%, 97%, 98%, 99% or 100% identical to SEQ ID NO: 56, a heavy chain comprising a sequence at least 90%, 91%, 92%, 93%, 94%, 95%, 96%, 97%, 98%, 99% or 100% identical to SEQ ID NO: 55, and a light chain comprising a sequence at least 90%, 91%, 92%, 93%, 94%, 95%, 96%, 97%, 98%, 99% or 100% identical to SEQ ID NO:57.

In a particular embodiment, the multispecific antigen binding protein or bispecific antibody comprises an IL-18 binding domain and an IL-23 binding domain wherein said multispecific antigen binding protein or bispecific antibody comprises a heavy chain comprising a sequence at least 90%, 91%, 92%, 93%, 94%, 95%, 96%, 97%, 98%, 99% or 100% identical to SEQ ID NO: 54, a light chain comprising a sequence at least 90%, 91%, 92%, 93%, 94%, 95%, 96%, 97%, 98%, 99% or 100% identical to SEQ ID NO: 56, a heavy chain comprising a sequence at least 90%, 91%, 92%, 93%, 94%, 95%, 96%, 97%, 98%, 99% or 100% identical to SEQ ID NO: 55, and a light chain comprising a sequence at least 90%, 91%, 92%, 93%, 94%, 95%, 96%, 97%, 98%, 99% or 100% identical to SEQ ID NO:57. In an embodiment, the multispecific antigen binding protein or bispecific antibody comprises an IL-18 binding domain and an IL-23 binding domain wherein said multispecific antigen binding protein or bispecific antibody comprises a heavy chain comprising a sequence at least 95% identical to SEQ ID NO: 54, a light chain comprising a sequence at least 95% identical to SEQ ID NO: 56, a heavy chain comprising a sequence at least 95% identical to SEQ ID NO: 55, and a light chain comprising a sequence at least 95% identical to SEQ ID NO:57.

In an embodiment there is provided a multispecific antigen binding protein or bispecific antibody comprising an IL-18 binding domain and an IL-23 binding domain wherein said multispecific antigen binding protein comprises:

a. a heavy chain comprising a variant of the amino acid sequence set forth in SEQ ID NO:42, a light chain comprising a variant of the amino acid sequence set forth in SEQ ID NO: 44, a heavy chain comprising a variant of the amino acid sequence set forth in SEQ ID NO: 43, and a light chain comprising a variant of the amino acid sequence set forth in SEQ ID NO:45;

b. a heavy chain comprising a variant of the amino acid sequence set forth in SEQ ID NO:47, a light chain comprising a variant of the amino acid sequence set forth in SEQ ID NO: 49, a heavy chain comprising a variant of the amino acid sequence set forth in SEQ ID NO: 46, and a light chain comprising a variant of the amino acid sequence set forth in SEQ ID NO:48;

c. a heavy chain comprising a variant of the amino acid sequence set forth in SEQ ID NO:50, a light chain comprising a variant of the amino acid sequence set forth in SEQ ID NO: 52, a heavy chain comprising a variant of the amino acid sequence set forth in SEQ ID NO: 51, and a light chain comprising a variant of the amino acid sequence set forth in SEQ ID NO:53; or d. a heavy chain comprising a variant of the amino acid sequence set forth in SEQ ID NO: 54, a light chain comprising a variant of the amino acid sequence set forth in SEQ ID NO: 56, a heavy chain comprising a variant of the amino acid sequence set forth in SEQ ID NO: 55, and a light chain comprising a variant of the amino acid sequence set forth in SEQ ID NO:57;

wherein in each case, each variant may contain 10, 9, 8, 7, 6, 5, 4, 3, 2 or 1 amino acid substitutions, insertions, or deletions.

In a particular embodiment, the multispecific antigen binding protein or bispecific antibody comprises an IL-18 binding domain and an IL-23 binding domain wherein said multispecific antigen binding protein comprises a heavy chain comprising a variant of the amino acid sequence set forth in SEQ ID NO: 54, a light chain comprising a variant of the amino acid sequence set forth in SEQ ID NO: 56, a heavy chain comprising a variant of the amino acid sequence set forth in SEQ ID NO: 55, and a light chain comprising a variant of the amino acid sequence set forth in SEQ ID NO:57, wherein in each case, each variant may contain 10, 9, 8, 7, 6, 5, 4, 3, 2 or 1 amino acid substitutions, insertions, or deletions.

In an embodiment there is provided a multispecific antigen binding protein or bispecific antibody comprising an IL-18 binding domain and an IL-23 binding domain wherein said multispecific antigen binding protein comprises:

a. a heavy chain of SEQ ID NO:42, a light chain of SEQ ID NO: 44, a heavy chain of SEQ ID NO: 43, and a light chain of SEQ ID NO:45;

b. a heavy chain of SEQ ID NO:47, a light chain of SEQ ID NO: 49, a heavy chain of SEQ ID NO: 46, and a light chain of SEQ ID NO:48;

c. a heavy chain of SEQ ID NO:50, a light chain of SEQ ID NO: 52, a heavy chain of SEQ ID NO: 51, and a light chain of SEQ ID NO:53; or d. a heavy chain of SEQ ID NO: 54, a light chain of SEQ ID NO: 56, a heavy chain of SEQ ID NO: 55, and a light chain of SEQ ID NO:57.

In a particular embodiment, the multispecific antigen binding protein comprises an IL-18 binding domain and an IL-23 binding domain wherein said multispecific antigen binding protein comprises a heavy chain of SEQ ID NO: 54, a light chain of SEQ ID NO: 56, a heavy chain of SEQ ID NO: 55, and a light chain of SEQ ID NO:57.

In an embodiment, the multispecific antigen binding protein or bispecific antibody of the present disclosure comprises an IL-18 binding domain and an IL-23 binding domain wherein said multispecific antigen binding protein or bispecific antibody comprises:

a. an IL-18 binding domain having a heavy chain comprising a sequence at least 90%, 91%, 92%, 93%, 94%, 95%, 96%, 97%, 98%, 99% or 100% identical to SEQ ID NO: 42 and a light chain comprising a sequence at least 90%, 91%, 92%, 93%, 94%, 95%, 96%, 97%, 98%, 99% or 100% identical to SEQ ID NO:44 and an IL-23 binding domain having a heavy chain comprising a sequence at least 90%, 91%, 92%, 93%, 94%, 95%, 96%, 97%, 98%, 99% or 100% identical to SEQ ID NO: 43, and a light chain comprising a sequence at least 90%, 91%, 92%, 93%, 94%, 95%, 96%, 97%, 98%, 99% or 100% identical to SEQ ID NO: 45;

b. an IL-18 binding domain having a heavy chain comprising a sequence at least 90%, 91%, 92%, 93%, 94%, 95%, 96%, 97%, 98%, 99% or 100% identical to SEQ ID NO: 47 and a light chain comprising a sequence at least 90%, 91%, 92%, 93%, 94%, 95%, 96%, 97%, 98%, 99% or 100% identical to SEQ ID NO:49 and an IL-23 binding domain having a heavy chain comprising a sequence at least 90%, 91%, 92%, 93%, 94%, 95%, 96%, 97%, 98%, 99% or 100% identical to SEQ ID NO: 46, and a light chain comprising a sequence at least 90%, 91%, 92%, 93%, 94%, 95%, 96%, 97%, 98%, 99% or 100% identical to SEQ ID NO: 48;

c. an IL-18 binding domain having a heavy chain comprising a sequence at 90%, 91%, 92%, 93%, 94%, 95%, 96%, 97%, 98%, 99% or 100% identical to SEQ ID NO: 50 and a light chain comprising a sequence at least 90%, 91%, 92%, 93%, 94%, 95%, 96%, 97%, 98%, 99% or 100% identical to SEQ ID NO:52 and an IL-23 binding domain having a heavy chain comprising a sequence at least 90%, 91%, 92%, 93%, 94%, 95%, 96%, 97%, 98%, 99% or 100% identical to SEQ ID NO: 51 and a light chain comprising a sequence at least 90%, 91%, 92%, 93%, 94%, 95%, 96%, 97%, 98%, 99% or 100% identical to SEQ ID NO: 53; or d. an IL-18 binding domain having a heavy chain comprising a sequence at least 90%, 91%, 92%, 93%, 94%, 95%, 96%, 97%, 98%, 99% or 100% identical to SEQ ID NO: 55 and a light chain comprising a sequence at least 90%, 91%, 92%, 93%, 94%, 95%, 96%, 97%, 98%, 99% or 100% identical to SEQ ID NO:57 and an IL-23 binding domain having a heavy chain comprising a sequence at least 90%, 91%, 92%, 93%, 94%, 95%, 96%, 97%, 98%, 99% or 100% identical to SEQ ID NO: 54, and a light chain comprising a sequence at least 90%, 91%, 92%, 93%, 94%, 95%, 96%, 97%, 98%, 99% or 100% identical to SEQ ID NO: 56.

In a particular embodiment, the multispecific antigen binding protein or bispecific antibody comprises an IL-18 binding domain and an IL-23 binding domain wherein said IL-18 binding domain comprises a heavy chain comprising a sequence at least 90%, 91%, 92%, 93%, 94%, 95%, 96%, 97%, 98%, 99% or 100% identical to SEQ ID NO: 55 and a light chain comprising a sequence at least 90%, 91%, 92%, 93%, 94%, 95%, 96%, 97%, 98%, 99% or 100% identical to SEQ ID NO:57 and said IL-23 binding domain comprises a heavy chain comprising a sequence at least 90%, 91%, 92%, 93%, 94%, 95%, 96%, 97%, 98%, 99% or 100% identical to SEQ ID NO: 54 and a light chain comprising a sequence at least 90%, 91%, 92%, 93%, 94%, 95%, 96%, 97%, 98%, 99% or 100% identical to SEQ ID NO: 56. In an embodiment, the multispecific antigen binding protein or bispecific antibody comprises an IL-18 binding domain and an IL-23 binding domain wherein said IL-18 binding domain comprises a heavy chain comprising a sequence at least 95% identical to SEQ ID NO: 55 and a light chain comprising a sequence at least 95% identical to SEQ ID NO:57 and said IL-23 binding domain comprises a heavy chain comprising a sequence at least 95% identical to SEQ ID NO: 54 and a light chain comprising a sequence at least 95% identical to SEQ ID NO: 56.

In an embodiment, the multispecific antigen binding protein or bispecific antibody of the present disclosure comprises an IL-18 binding domain and an IL-23 binding domain wherein said multispecific antigen binding protein or bispecific antibody comprises:

a. an IL-18 binding domain having a heavy chain comprising a variant of the amino acid sequence set forth in SEQ ID NO: 42 and a light chain comprising a variant of the amino acid sequence set forth in SEQ ID NO:44 and an IL-23 binding domain having a heavy chain comprising a variant of the amino acid sequence set forth in SEQ ID NO: 43, and a light chain comprising a variant of the amino acid sequence set forth in SEQ ID NO: 45;

b. an IL-18 binding domain having a heavy chain comprising a variant of the amino acid sequence set forth in SEQ ID NO: 47 and a light chain comprising a variant of the amino acid sequence set forth in SEQ ID NO:49 and an IL-23 binding domain having a heavy chain comprising a variant of the amino acid sequence set forth in SEQ ID NO: 46 and a light chain comprising a variant of the amino acid sequence set forth in SEQ ID NO: 48;

c. an IL-18 binding domain having a heavy chain comprising a variant of the amino acid sequence set forth in SEQ ID NO: 50 and a light chain comprising a variant of the amino acid sequence set forth in SEQ ID NO:52 and an IL-23 binding domain having a heavy chain comprising a variant of the amino acid sequence set forth in SEQ ID NO: 51, and a light chain comprising a variant of the amino acid sequence set forth in SEQ ID NO: 53; or d. an IL-18 binding domain having a heavy chain comprising a variant of the amino acid sequence set forth in SEQ ID NO: 55 and a light chain comprising a variant of the amino acid sequence set forth in SEQ ID NO:57 and an IL-23 binding domain having a heavy chain comprising a variant of the amino acid sequence set forth in SEQ ID NO: 54, and a light chain comprising a variant of the amino acid sequence set forth in SEQ ID NO: 56, wherein in each case, each variant may contain 10, 9, 8, 7, 6, 5, 4, 3, 2 or 1 amino acid substitutions, insertions, or deletions.

In a particular embodiment, the multispecific antigen binding protein or bispecific antibody comprises an IL-18 binding domain and an IL-23 binding domain wherein said IL-18 binding domain comprises a heavy chain comprising a variant of the amino acid sequence set forth in SEQ ID NO: 55 and a light chain comprising a variant of the amino acid sequence set forth in SEQ ID NO:57 and said IL-23 binding domain comprises a heavy chain comprising a variant of the amino acid sequence set forth in SEQ ID NO: 54 and a light chain comprising a variant of the amino acid sequence set forth in SEQ ID NO: 56, wherein in each case, each variant may contain 10, 9, 8, 7, 6, 5, 4, 3, 2 or 1 amino acid substitutions, insertions, or deletions.

In an embodiment, the multispecific antigen binding protein or bispecific antibody of the present disclosure comprises an IL-18 binding domain and an IL-23 binding domain wherein said multispecific antigen binding protein or bispecific antibody comprises:

a. an IL-18 binding domain having a heavy chain of SEQ ID NO: 42 and a light chain of SEQ ID NO:44 and an IL-23 binding domain having a heavy chain of SEQ ID NO: 43, and a light chain of SEQ ID NO: 45;

b. an IL-18 binding domain having a heavy chain of SEQ ID NO: 47 and a light chain of SEQ ID NO:49 and an IL-23 binding domain having a heavy chain of SEQ ID NO: 46 and a light chain of SEQ ID NO: 48;

c. an IL-18 binding domain having a heavy chain of SEQ ID NO: 50 and a light chain of SEQ ID NO:52 and an IL-23 binding domain having a heavy chain of SEQ ID NO: 51, and a light chain of SEQ ID NO: 53; or d. an IL-18 binding domain having a heavy chain of SEQ ID NO: 55 and a light chain of SEQ ID NO:57 and an IL-23 binding domain having a heavy chain of SEQ ID NO: 54, and a light chain of SEQ ID NO: 56.

In a particular embodiment, the multispecific antigen binding protein or bispecific antibody of the disclosure comprises an IL-18 binding domain and an IL-23 binding domain wherein said IL-18 binding domain comprises a heavy chain of SEQ ID NO: 55 and a light chain of SEQ ID NO:57 and said IL-23 binding domain comprises a heavy chain of SEQ ID NO: 54, and a light chain of SEQ ID NO: 56. In an embodiment, the antigen binding protein or bispecific antibody of the disclosure comprises: an anti-IL-18 HC of SEQ ID NO:55; an anti-IL-18 LC of SEQ ID NO:57; an anti-IL-23 HC of SEQ ID NO:54; and an anti-IL-23 LC of SEQ ID NO:56. In an embodiment the multispecific antigen binding protein or bispecific antibody of the disclosure is an anti-IL-18 and anti-IL-23 bispecific antibody, wherein the anti-IL-18 heavy chain sequence is that of SEQ ID NO: 55, the anti-IL-18 light chain sequence is that of SEQ ID NO: 57, the anti-IL-23 heavy chain sequence is that of SEQ ID NO: 54, and the anti-IL-23 light chain sequence is that of SEQ ID NO:56.

In an embodiment, the multispecific antigen binding protein or bispecific antibody of the disclosure comprises an IL-18 binding domain and an IL-23 binding domain wherein:

i) said IL-18 binding domain comprises a heavy chain comprising a variant of the amino acid sequence set forth in SEQ ID NO: 55 that contains up to 10 amino acid substitutions, insertions, or deletions; and a light chain comprising a variant of the amino acid sequence set forth in SEQ ID NO:57 that contains up to 10 amino acid substitutions, insertions, or deletions; and wherein ii) said IL-23 binding domain comprises a heavy chain comprising a variant of the amino acid sequence set forth in SEQ ID NO: 54 that contains up to 10 amino acid substitutions, insertions, or deletions; and a light chain comprising a variant of the amino acid sequence set forth in SEQ ID NO: 56 that contains up to 10 amino acid substitutions, insertions, or deletions;

wherein none of the amino acid substitutions, insertions, or deletions are within any of the CDRs.

In an embodiment, the multispecific antigen binding protein or bispecific antibody of the disclosure comprises an IL-18 binding domain and an IL-23 binding domain wherein:

i) said IL-18 binding domain comprises a heavy chain comprising a variant of the amino acid sequence set forth in SEQ ID NO: 55 that contains up to 5 amino acid substitutions, insertions, or deletions; and a light chain comprising a variant of the amino acid sequence set forth in SEQ ID NO:57 that contains up to 5 amino acid substitutions, insertions, or deletions; and wherein ii) said IL-23 binding domain comprises a heavy chain comprising a variant of the amino acid sequence set forth in SEQ ID NO: 54 that contains up to 5 amino acid substitutions, insertions, or deletions; and a light chain comprising a variant of the amino acid sequence set forth in SEQ ID NO: 56 that contains up to 5 amino acid substitutions, insertions, or deletions;

wherein none of the amino acid substitutions, insertions, or deletions are within any of the CDRs.

In an embodiment, the multispecific antigen binding protein or bispecific antibody of the disclosure comprises an IL-18 binding domain and an IL-23 binding domain wherein:

i) said IL-18 binding domain comprises a heavy chain comprising a variant of the amino acid sequence set forth in SEQ ID NO: 55 that contains up to 10 amino acid substitutions, insertions, or deletions; and a light chain comprising a variant of the amino acid sequence set forth in SEQ ID NO:57 that contains up to 10 amino acid substitutions, insertions, or deletions; and wherein ii) said IL-23 binding domain comprises a heavy chain comprising a variant of the amino acid sequence set forth in SEQ ID NO: 54 that contains up to 10 amino acid substitutions, insertions, or deletions; and a light chain comprising a variant of the amino acid sequence set forth in SEQ ID NO: 56 that contains up to 10 amino acid substitutions, insertions, or deletions;

wherein none of the amino acid substitutions, insertions, or deletions are within any of the CDRs and none of the amino acid substitutions, insertions, or deletions are within YTE (M252Y/S254T/T256E).

In an embodiment, the multispecific antigen binding protein or bispecific antibody of the disclosure comprises an IL-18 binding domain and an IL-23 binding domain wherein:

i) said IL-18 binding domain comprises a heavy chain comprising a variant of the amino acid sequence set forth in SEQ ID NO: 55 that contains up to 5 amino acid substitutions, insertions, or deletions; and a light chain comprising a variant of the amino acid sequence set forth in SEQ ID NO:57 that contains up to 5 amino acid substitutions, insertions, or deletions; and wherein ii) said IL-23 binding domain comprises a heavy chain comprising a variant of the amino acid sequence set forth in SEQ ID NO: 54 that contains up to 5 amino acid substitutions, insertions, or deletions; and a light chain comprising a variant of the amino acid sequence set forth in SEQ ID NO: 56 that contains up to 5 amino acid substitutions, insertions, or deletions;

wherein none of the amino acid substitutions, insertions, or deletions are within any of the CDRs and none of the amino acid substitutions, insertions, or deletions are within YTE (M252Y/S254T/T256E).

In an embodiment, the multispecific antigen binding protein or bispecific antibody of the disclosure comprises an IL-18 binding domain and an IL-23 binding domain wherein:

i) said IL-18 binding domain comprises a heavy chain comprising CDRH1 (SEQ ID NO:2), CDRH2 (SEQ ID NO:3), and CDRH3 (SEQ ID NO:4), and having 95% or greater identity to SEQ ID NO: 55 and a light chain comprising CDRL1 (SEQ ID NO:5), CDRL2 (SEQ ID NO:6), and CDRL3 (SEQ ID NO:7), and having 95% or greater identity to SEQ ID NO: 57; and wherein ii) said IL-23 binding domain comprises a heavy chain comprising CDRH1 (SEQ ID NO:10), CDRH2 (SEQ ID NO:11), and CDRH3 (SEQ ID NO:12), and having 95% or greater identity to SEQ ID NO: 54 and a light chain comprising CDRL1 (SEQ ID NO:13), CDRL2

(SEQ ID NO:14), and CDRL3 (SEQ ID NO:15), and having 95% or greater identity to SEQ ID NO: 56.

In an embodiment, the multispecific antigen binding protein or bispecific antibody of the disclosure comprises an IL-18 binding domain and an IL-23 binding domain wherein:

i) said IL-18 binding domain comprises a heavy chain comprising CDRH1 (SEQ ID NO:2), CDRH2 (SEQ ID NO:3), and CDRH3 (SEQ ID NO:4), and YTE (M252Y/S254T/T256E), and having 95% or greater identity to SEQ ID NO: 55 and a light chain comprising CDRL1 (SEQ ID NO:5), CDRL2 (SEQ ID NO:6), and CDRL3 (SEQ ID NO:7), and having 95% or greater identity to SEQ ID NO: 57; and wherein ii) said IL-23 binding domain comprises a heavy chain comprising CDRH1 (SEQ ID NO:10), CDRH2 (SEQ ID NO:11), and CDRH3 (SEQ ID NO:12), and YTE (M252Y/S254T/T256E), and having 95% or greater identity to SEQ ID NO: 54 and a light chain comprising CDRL1 (SEQ ID NO:13), CDRL2 (SEQ ID NO:14), and CDRL3 (SEQ ID NO:15), and having 95% or greater identity to SEQ ID NO: 56.

Further provided within the present disclosure are anti-IL-18 and anti-IL-23 bispecific antibodies, comprising:

a. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15; wherein the anti-IL-18 heavy chain has a sequence identity of 95% or greater to SEQ ID NO: 42, the anti-IL-18 light chain has a sequence identity of 95% or greater to SEQ ID NO:44, the anti-IL-23 heavy chain has a sequence identity of 95% or greater to SEQ ID NO:43, and the anti-IL-23 light chain has a sequence identity of 95% or greater to SEQ ID NO: 45;

b. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15; wherein the anti-IL-18 heavy chain has a sequence identity of 95% or greater to SEQ ID NO: 47, the anti-IL-18 light chain has a sequence identity of 95% or greater to SEQ ID NO:49, the anti-IL-23 heavy chain has a sequence identity of 95% or greater to SEQ ID NO:46, and the anti-IL-23 light chain has a sequence identity of 95% or greater to SEQ ID NO: 48.

c. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:18, CDRH2 of SEQ ID NO:19, CDRH3 of SEQ ID NO:20, CDRL1 of SEQ ID NO:21, CDRL2 of SEQ ID NO:22 and CDRL3 of SEQ ID NO:23; wherein the anti-IL-18 heavy chain has a sequence identity of 95% or greater to SEQ ID NO: 50, the anti-IL-18 light chain has a sequence identity of 95% or greater to SEQ ID NO:52, the anti-IL-23 heavy chain has a sequence identity of 95% or greater to SEQ ID NO:51, and the anti-IL-23 light chain has a sequence identity of 95% or greater to SEQ ID NO: 53; or d. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15; wherein the anti-IL-18 heavy chain has a sequence identity of 95% or greater to SEQ ID NO: 55, the anti-IL-18 light chain has a sequence identity of 95% or greater to SEQ ID NO:57, the anti-IL-23 heavy chain has a sequence identity of 95% or greater to SEQ ID NO:54, and the anti-IL-23 light chain has a sequence identity of 95% or greater to SEQ ID NO:56.

In an embodiment, the anti-IL-18 and anti-IL-23 bispecific antibody comprises:

i. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7;

ii. anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15;

iii. an Fc region comprising M252Y, S254T and T256E; wherein the anti-IL-18 heavy chain has a sequence identity of 95% or greater to SEQ ID NO: 55, the anti-IL-18 light chain has a sequence identity of 95% or greater to SEQ ID NO:57, the anti-IL-23 heavy chain has a sequence identity of 95% or greater to SEQ ID NO:54, and the anti-IL-23 light chain has a sequence identity of 95% or greater to SEQ ID NO:56. In an embodiment, the Fc region further comprises the amino acid substitutions L235A and G237A (EU index numbering).

Further provided herein are bispecific antibodies comprising an IL-18 binding domain and a domain comprising a means for specifically binding IL-23. In a particular embodiment there is provided a bispecific antibody comprising an IL-18 binding domain comprising the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and a domain comprising a means for specifically binding IL-23 (e.g. human IL-23, in particular human IL-23-p19 the sequence of which is as shown in SEQ ID NO: 74). In an embodiment, said IL-18 binding domain comprises a VH domain comprising a sequence at least 90% identical to SEQ ID NO: 8 and a VL domain comprising a sequence at least 90% identical to SEQ ID NO: 9. In an embodiment, said IL-18 binding domain comprises a VH domain comprising SEQ ID NO: 8 and a VL domain comprising SEQ ID NO: 9. In an embodiment, the means for specifically binding IL-23 comprises a VH domain and a VL domain, optionally wherein the VH domain comprises a sequence at least 90%, at least 95% or at least 98% identical to SEQ ID NO: 16 and wherein the VL domain comprises a sequence at least 90%, at least 95% or at least 98% identical to SEQ ID NO: 17. In an embodiment said means for specifically binding IL-23 has an equilibrium affinity of at least 600 pM at 25° C. as measured by surface plasmon resonance.

Additionally provided herein are bispecific antibodies comprising an IL-23 binding domain and a domain comprising a means for specifically binding IL-18. In a particular embodiment there is provided a bispecific antibody comprising an IL-23 binding domain comprising the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15 and a domain comprising a means for specifically binding IL-18 (e.g. human IL-18, in particular human IL-18 the sequence of which is as shown in SEQ ID NO: 1). In an embodiment, said IL-23 binding domain comprises a VH domain comprising a sequence at least 90% identical to SEQ ID NO: 16 and a VL domain comprising a sequence at least 90% identical to SEQ ID NO: 17. In an embodiment, said IL-23 binding domain comprises a VH domain comprising SEQ ID NO: 16 and a VL domain comprising SEQ ID NO: 17. In an embodiment, the means for specifically binding IL-18 comprises a VH domain and a VL domain, optionally wherein the VH domain comprises a sequence at least 90%, at least 95% or at least 98% identical to SEQ ID NO: 8 and wherein the VL domain comprises a sequence at least 90%, at least 95% or at least 98% identical to SEQ ID NO: 9. In an embodiment said means for specifically binding IL-18 has an equilibrium affinity of at least 100 pM at 25° C. as measured by surface plasmon resonance.

Further provided herein are bispecific antibodies comprising: i) an IL-18 binding domain comprising the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7; and ii) a means for specifically binding a human IL-23 protein. In an embodiment, said means for specifically binding human IL-23 has an equilibrium affinity of at least 600 pM at 25° C. as measured by surface plasmon resonance. In an embodiment, the means for specifically binding a human IL-23 protein comprises a VH domain and a VL domain. In an embodiment, the VH domain of the means for specifically binding a human IL-23 comprises SEQ ID NO: 16, SEQ ID NO: 24, SEQ ID NO: 32, SEQ ID NO: 40 or SEQ ID NO: 64. In an embodiment the VL domain of the means for specifically binding a human IL-23 comprises SEQ ID NO: 17, SEQ ID NO: 25, SEQ ID NO: 33, SEQ ID NO: 41 or SEQ ID NO: 65. In an embodiment said bispecific antibody is a Het-mAb. In an embodiment said bispecific antibody is an IgG1κ antibody, optionally wherein the IgG1 Fc portion is mutated at the sequences corresponding to the canonocial IgG1 framework at each of the following positions: M252Y, S254T, and T256E. In an embodiment the Fc region further comprises the amino acid substitutions L235A and G237A.

Additionally provided herein are bispecific antibodies comprising: i) an IL-23 binding domain comprising the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15; and ii) a means for specifically binding a human IL-18 protein. In an embodiment, said means for specifically binding human IL-18 has an equilibrium affinity of at least 100 pM at 25° C. as measured by surface plasmon resonance. In an embodiment, the means for specifically binding a human IL-18 protein comprises a VH domain and a VL domain. In an embodiment, the VH domain of the means for specifically binding a human IL-18 comprises SEQ ID NO: 8, SEQ ID NO: 72 or SEQ ID NO: 82. In an embodiment the VL domain of the means for specifically binding a human IL-18 comprises SEQ ID NO: 9, SEQ ID NO: 73 or SEQ ID NO: 83. In an embodiment said bispecific antibody is a Het-mAb. In an embodiment said bispecific antibody is an IgG1κ antibody, optionally wherein the IgG1 Fc portion is mutated at the sequences corresponding to the canonocial IgG1 framework at each of the following positions: M252Y, S254T, and T256E. In an embodiment the Fc region further comprises the amino acid substitutions L235A and G237A.

In an embodiment there is provided a Het-mAb format bispecific antibody comprising an IL-18 binding domain comprising a VH domain according to SEQ ID NO: 8 and a VL domain according to SEQ ID NO: 9, an IgG1 Fc domain, and a means for specifically binding to human IL-23. In an embodiment, the means for specifically binding to human IL-23 has an equilibrium affinity of at least 600 pM at 25° C. as measured by surface plasmon resonance. In an embodiment there is provided a Het-mAb format bispecific antibody comprising an IL-23 binding domain comprising a VH domain according to SEQ ID NO: 16 and a VL domain according to SEQ ID NO: 17, an IgG1 Fc domain, and a means for specifically binding to human IL-18. In an embodiment, the means for specifically binding to human IL-23 has an equilibrium affinity of at least 100 pM at 25° C. as measured by surface plasmon resonance.

A multispecific antigen binding protein or bispecific antibody of the disclosure may neutralise the activity of IL-18 by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to IL-18 activity in the absence of the IL-18 binding domain (or relative to IL-18 activity in the presence of a control antibody). Neutralisation may be determined or measured using one or more assays known to the skilled person or as described herein, for example (but by no means limited to) the KG-1 assay (see Example 6).

A multispecific antigen binding protein or bispecific antibody of the disclosure may neutralise the activity of IL-23 by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to IL-23 activity in the absence of the IL-23 binding domain (or relative to the IL-23 activity in the presence of a control antibody). Neutralisation may be determined or measured using one or more assays known to the skilled person or as described herein, for example (but by no means limited to) the DB assay (see Example 5).

In an embodiment, the multispecific antigen binding protein or bispecific antibody of the disclosure down-regulates C-X-C motif chemokine ligand 13 (CXCL13) expression. CXCL13 (that is also known as B cell attracting chemokine (BCA-1) or B lymphocyte chemoattractant (BLC)) is a chemokine that regulates the homing of B cells and T cells subsets (Jiang et al. *J Clin Invest* (2016) 126:745-61). In an embodiment, the multispecific antigen binding protein or bispecific antibody of the disclosure down-regulates or inhibits CXCL13 secretion following introduction of said multispecific antigen binding protein or bispecific antibody to a co-culture comprising activated CD14$^+$ myeloid cells and CD3$^+$ T cells. In an embodiment, said multispecific antigen binding or bispecific antibody down-regulates or inhibits CXCL13 secretion by greater than 10%, greater than 15%, greater than 20%, greater than 25%, greater than 30%, greater than 35%, greater than 40% or greater than 45% compared to a negative control antigen binding protein (e.g., an isotype control antibody or an antibody that does not bind to either IL-18 or IL-23 or that does bind to IL-18 or IL-23 but only with low affinity i.e., with a Kd of $1 \times 10^{-6}$ M or more, for example, $1 \times 10^{-5}$ M or more, $1 \times 10^{-4}$ M or more, $1 \times 10^{-3}$ M or more, or $1 \times 10^{-2}$ M or more) or compared to no treatment control.

In an embodiment, the equilibrium dissociation constant (KD) of the multispecific antigen binding protein—IL-18 interaction and/or of the multispecific antigen binding protein—IL-23 interaction is about 1 nM or less, 500 pM or less, 250 pM or less. of 150 pM or less, 100 pM or less, 50 pM or less, or 40 pM or less. Alternatively, the KD may be between about 10 pM and about 150 pM, between about 10 pM and about 100 pM, between about 20 pM and about 100 pM; between about 20 pM and about 50 pM, or between about 20 pM and about 40 pM. A skilled person will appreciate that the smaller the KD numerical value, the stronger the binding. The reciprocal of KD (i.e., 1/KD) is the equilibrium association constant (KA) having units M$^{-1}$. A skilled person will appreciate that the larger the KA numerical value, the stronger the binding. The KD values provided herein are all provided in respect of binding to human IL-18 and human IL-23.

In an embodiment, the KD of the multispecific antigen binding protein (or bispecific antibody)—IL-18 interaction is less than about 150 pM at 25° C. In an embodiment, the KD of the multispecific antigen binding protein (or bispecific antibody)—IL-18 interaction is less than about 110 pM at 25° C. In an embodiment, the KD of the multispecific antigen binding protein (or bispecific antibody)—IL-18 interaction is less than about 50 pM at 25° C. In an embodiment, the KD of the multispecific antigen binding protein (or bispecific antibody)—IL-18 interaction is less than about 40 pM at 25° C. In an embodiment, the KD of the multispecific antigen binding protein (or bispecific antibody)—IL-18 interaction is between about 10 pM and about 150 pM. In an embodiment, the KD of the multispecific antigen binding protein (or bispecific antibody)—IL-18 interaction is between about 10 pM and about 110 pM. In an embodiment, the KD of the multispecific antigen binding protein (or bispecific antibody)—IL-18 interaction is between about 20 pM and about 50 pM. In an embodiment, the KD of the multispecific antigen binding protein (or bispecific antibody)—IL-18 interaction is between about 25 pM and about 45 pM at 25° C. In an embodiment, said IL-18 is human IL-18.

In an embodiment, the KD of the multispecific antigen binding protein (or bispecific antibody)—IL-23 interaction is less than about 750 pM at 25° C. In an embodiment, the KD of the multispecific antigen binding protein (or bispecific antibody)—IL-23 interaction is less than about 600 pM at 25° C. In an embodiment, the KD of the multispecific antigen binding protein (or bispecific antibody)—IL-23 interaction is less than about 450 pM at 25° C. In an embodiment, the KD of the multispecific antigen binding protein (or bispecific antibody)—IL-23 interaction is less than about 350 pM at 25° C. In an embodiment, the KD of the multispecific antigen binding protein (or bispecific antibody)—IL-23 interaction is between about 50 pM and about 600 pM. In an embodiment, the KD of the multispecific antigen binding protein (or bispecific antibody)—IL-23 interaction is between about 100 pM and about 500 pM. In an embodiment, the KD of the multispecific antigen binding protein (or bispecific antibody)—IL-23 interaction is between about 150 pM and about 400 pM. In an embodiment, the KD of the multispecific antigen binding protein (or bispecific antibody)—IL-23 interaction is between about 250 pM and about 350 pM at 25° C. In an embodiment, said IL-23 is human IL-23.

A skilled person will appreciate that surface plasmon resonance (SPR) is a suitable method to measure binding affinity and also determine binding kinetics, see, e.g., Day et al., Direct comparison of binding equilibrium, thermodynamic, and rate constants determined by surface- and solution-based biophysical methods, Protein Science (2002), 11:1017-1025; and, Hearty et al, "Measuring antibody-antigen binding kinetics using surface plasmon resonance" Methods Mol Biol (2012) 907:411-4.

In some embodiments, the multispecific antigen binding proteins and bispecific antibodies of the present disclosure show cross-reactivity between human IL-23 and IL-23 from another species, such as cynomolgus macaque IL-23 and/or show cross-reactivity between human IL-18 and IL-18 from another species, such as cynomolgus macaque IL-18. In an embodiment, the IL-23 binding domains of the disclosure specifically bind human and macaque IL-23. In an embodiment, the IL-18 binding domains of the disclosure specifically bind human and macaque IL-18. In an embodiment, the IL-23 binding domains of the disclosure specifically bind human and macaque IL-23 and the IL-18 binding domains of the disclosure specifically bind human and macaque IL-18. This is particularly useful, since drug development typically requires testing of lead drug candidates in animal systems before the drug is tested in humans. Cross reactivity between other species used in disease models such as dog or mice is also desirable and could be readily tested by the person skilled in the art.

Production:

Multispecific antigen binding proteins of the disclosure, including bispecific antibodies, may be prepared by any of a number of conventional techniques. For example, multispecific antigen binding proteins may be purified from cells that naturally express them (e.g., an antibody can be purified from a hybridoma that produces it) or produced in recombinant expression systems. A number of different expression systems and purification regimes can be used to generate the multispecific antigen binding proteins and bispecific antibodies of the disclosure. Generally, host cells are transformed with a recombinant expression vector encoding the desired multispecific antigen binding protein or bispecific antibody. The expression vector may be maintained by the host as a separate genetic element or integrated into the host chromosome depending on the expression system.

In an embodiment the multispecific antigen binding proteins of the present disclosure have been tested in a number of assays, including those to assess the developability of said binding proteins. For example, the multispecific antigen binding proteins were found to be desirable candidates for further clinical development based on having a low propensity for self-association (i.e., aggregation), greater stability (e.g., under stressed conditions), low levels of non-specific binding and were capable of being formulated into high concentration formulations (such as those required for subcutaneous administration).

In an aspect of the disclosure there is provided a nucleic acid sequence encoding a multispecific antigen binding protein or a bispecific antibody of the disclosure. In an embodiment, the nucleic acid sequence encodes any one, two, three or all four of the following amino acid sequences: a heavy chain of SEQ ID NO: 54, a light chain of SEQ ID NO: 56, a heavy chain of SEQ ID NO:55 and a light chain of SEQ ID NO:57.

In an aspect of the disclosure, an expression vector comprising the nucleic acid sequence(s) of the disclosure is provided. In an embodiment, the vector comprises a nucleic acid sequence encoding any one, two, three or all four of the following amino acid sequences: a heavy chain of SEQ ID NO: 54, a light chain of SEQ ID NO: 56, a heavy chain of SEQ ID NO:55 and a light chain of SEQ ID NO:57. In an embodiment, the vector comprises the following nucleic acid sequences: a nucleic acid sequence encoding a heavy chain of SEQ ID NO: 54, a nucleic acid sequence encoding a light chain of SEQ ID NO:56, a nucleic acid sequence encoding a heavy chain of SEQ ID NO:55, and a nucleic acid sequence encoding a light chain of SEQ ID NO:57. In an embodiment, the vector comprises a nucleic acid sequence encoding a heavy chain of SEQ ID NO: 54 and a nucleic acid sequence encoding a light chain of SEQ ID NO:56. In an embodiment, the vector comprises a nucleic acid sequence encoding a heavy chain of SEQ ID NO:55 and a nucleic acid sequence encoding a light chain of SEQ ID NO:57. In an embodiment, the vector comprises a nucleic acid sequence encoding a heavy chain of SEQ ID NO: 54. In an embodiment, the vector comprises a nucleic acid sequence encoding a light chain of SEQ ID NO:56. In an embodiment, the vector comprises a nucleic acid sequence encoding a heavy chain of SEQ ID NO:55. In an embodiment, the vector comprises a nucleic acid sequence encoding a nucleic acid sequence encoding a light chain of SEQ ID NO:57.

In a further aspect of the disclosure there is provided a recombinant host cell comprising the nucleic acid sequence(s) or the expression vector(s) of the disclosure. A wide range of host cells can be employed, including Prokaryotes (including Gram negative or Gram-positive bacteria, for example *Escherichia coli*, Bacilli sp., *Pseudomonas* sp., *Corynebacterium* sp.), Eukaryotes including yeast (for example *Saccharomyces cerevisiae, Pichia pastoris*), fungi (for example *Aspergillus* sp.), or higher Eukaryotes including insect cells and cell lines of mammalian origin (for example, CHO, NS0, PER.C6, HEK293, HeLa).

The host cell may be an isolated host cell. The host cell is usually not part of a multicellular organism (e.g., plant or animal). The host cell may be a non-human host cell.

Appropriate cloning and expression vectors for use with bacterial, fungal, yeast, and mammalian host cells are known in the art.

The cells can be cultured under conditions that promote expression of the multispecific antigen binding protein or bispecific antibody using a variety of equipment such as shake flasks, spinner flasks, and bioreactors. The polypeptide is (or polypeptides are) recovered by conventional protein purification procedures. Protein purification procedures typically consist of a series of unit operations comprised of various filtration and chromatographic processes developed to selectively concentrate and isolate the antigen binding protein. The purified multispecific antigen binding protein or bispecific antibody may be formulated in a pharmaceutically acceptable composition.

Further provided are cell lines engineered to express the multispecific antigen binding proteins or the bispecific antibodies of the disclosure. In an embodiment, the multispecific antigen binding protein or bispecific antibody of the disclosure is produced in CHO cells.

Further provided are methods for the production of a multispecific antigen binding protein or bispecific antibody said method comprising culturing the recombinant host cell of the disclosure under conditions suitable for expression of said nucleic acid sequence(s) or vector(s), whereby said multispecific antigen binding protein or bispecific antibody is produced. Multispecific antigen binding proteins and bispecific antibodies produced by this method is furthermore provided.

Pharmaceutical Compositions and Methods of Use:

Multispecific antigen binding proteins and bispecific antibodies as described herein may be incorporated into pharmaceutical compositions for use in the treatment of diseases (e.g., human diseases) as described herein. Thus, in a further aspect there is provided a pharmaceutical composition comprising any of the multispecific antigen binding proteins or bispecific antibodies disclosed herein in combination with a pharmaceutically acceptable excipient.

In an embodiment the pharmaceutical composition comprises a multispecific antigen binding protein or bispecific antibody comprising an IL-18 binding domain and an IL-23 binding domain wherein, said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and wherein said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15, in combination with one or more pharmaceutically acceptable carriers and/or excipients.

In an embodiment the pharmaceutical composition comprises a multispecific antigen binding protein or bispecific antibody comprising an IL-18 binding domain and an IL-23 binding domain wherein:

i) said IL-18 binding domain comprises a heavy chain comprising CDRH1 (SEQ ID NO:2), CDRH2 (SEQ ID NO:3), and CDRH3 (SEQ ID NO:4), and having 95% or greater identity to SEQ ID NO: 55 and a light chain comprising CDRL1 (SEQ ID NO:5), CDRL2 (SEQ ID NO:6), and CDRL3 (SEQ ID NO:7), and having 95% or greater identity to SEQ ID NO: 57; and wherein ii) said IL-23 binding domain comprises a heavy chain comprising CDRH1 (SEQ ID NO:10), CDRH2 (SEQ ID NO:11), and CDRH3 (SEQ ID NO:12), and having 95% or greater identity to SEQ ID NO: 54 and a light chain comprising CDRL1 (SEQ ID NO:13), CDRL2 (SEQ ID NO:14), and CDRL3 (SEQ ID NO:15), and having 95% or greater identity to SEQ ID NO: 56, in combination with one or more pharmaceutically acceptable carriers and/or excipients.

In an embodiment the pharmaceutical composition comprises a multispecific antigen binding protein or bispecific antibody comprising an IL-18 binding domain and an IL-23 binding domain wherein: said IL-18 binding domain comprises a heavy chain of SEQ ID NO: 55 and a light chain of SEQ ID NO:57 and said IL-23 binding domain comprises a heavy chain of SEQ ID NO: 54, and a light chain of SEQ ID NO: 56 in combination with one or more pharmaceutically acceptable carriers and/or excipients. In an embodiment, said pharmaceutical composition is suitable for subcutaneous administration.

Pharmaceutical compositions may be administered by injection or continuous infusion (examples include, but are not limited to, intravenous, intraperitoneal, intradermal, subcutaneous, intramuscular, intraocular, and intraportal). In one embodiment, the pharmaceutical composition is suitable for intravenous or subcutaneous administration.

The pharmaceutical compositions of the present disclosure may be included in a kit containing the multispecific antigen binding protein or bispecific antibody together with other medicaments, and/or with instructions for use. For convenience, the kit may comprise the reagents in predetermined amounts with instructions for use. The kit may also include devices used for administration of the pharmaceutical composition. The kit may also include a device to be used for administration of the pharmaceutical composition, multispecific antigen binding protein or bispecific antibody of the disclosure. In an embodiment, each unit dose of the multispecific antigen binding protein or bispecific antibody of the disclosure is in a prefilled syringe. In an embodiment, the prefilled syringe is for subcutaneous injection. In an embodiment, each unit dose of the multispecific antigen binding protein or bispecific antibody of the disclosure is in an autoinjector. In an embodiment, the autoinjector is for subcutaneous injection. In an embodiment, the kit comprises one or more additional medicaments.

The multispecific antigen binding proteins and bispecific antibodies described herein may be used in methods of treatment. It will be appreciated by those skilled in the art that references herein to treatment refer to the treatment of established conditions. However, multispecific antigen binding proteins and bispecific antibodies described herein may, depending on the condition, also be useful in the prevention of certain diseases. The multispecific antigen binding proteins or bispecific antibodies described herein may be used in an effective amount for therapeutic, prophylactic or preventative treatment. A therapeutically effective amount of the multispecific antigen binding proteins or bispecific antibodies described herein is an amount effective to ameliorate or reduce one or more symptoms of, or to prevent or cure, the disease. The terms "individual", "subject" and "patient" are used herein interchangeably. In one embodiment, the subject is an animal. In another embodiment, the subject is a mammal, such as a primate, for example a marmoset or monkey. In another embodiment, the subject is a human. It is preferred that the subject is a human.

In an embodiment a multispecific antigen binding protein, in particular a bispecific antibody, described herein can be used for prophylactic or preventative treatment. In this case, the multispecific antigen binding protein or bispecific antibody is administered to an individual in order to prevent or delay the onset of one or more aspects or symptoms of a disease. The subject can be asymptomatic. The subject may have a genetic predisposition to the disease. In some embodiments, a prophylactically effective amount of the multispecific antigen binding protein or bispecific antibody is administered to such an individual. In some embodiments, a prophylactically effective amount is an amount which prevents or delays the onset of one or more aspects or symptoms of a disease described herein.

Those in need of treatment may include individuals already suffering from a medical disease in addition to those who may develop the disease in the future. In an embodiment, the subjects have inadequately responded to treatment prior biologic therapies for the same disease.

The use of a multispecific antigen binding protein, in particular a bispecific antibody, described herein need not affect a complete cure or eradicate every symptom or manifestation of the disease to constitute a viable therapeutic treatment. As is recognized in the pertinent field, therapeutic agents may reduce the severity of a given disease state but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient. In an embodiment, a treatment may comprise further monitoring of a disease or condition of a subject. A treatment may comprise a single treatment. A treatment may comprise a recurring treatment. A treatment may comprise a recurring treatment over a remaining lifespan of a subject. For example, treatment may comprise a weekly treatment. In some embodiments, a treatment may be selected based on an assessment of a patient or a sample obtained from the subject.

The present disclosure further provides a method for the treatment of disease in a subject in need thereof comprising administering to said subject a therapeutically effective amount of a multispecific antigen binding protein, a bispecific antibody or a pharmaceutical composition as disclosed herein.

In an aspect there is provided a method for the treatment of an immunoinflammatory disease in a subject in need thereof comprising administering to said subject a therapeutically effective amount of a multispecific antigen binding protein, a bispecific antibody or a pharmaceutical composition as disclosed herein.

In an aspect there is provided a method for the treatment of an immunoinflammatory disease selected from the group consisting of celiac disease, multiple sclerosis, atopic dermatitis, giant cell arteritis, rheumatoid arthritis, psoriasis, psoriatic arthritis, Behcet's disease and inflammatory bowel disease (IBD), including Crohn's disease (CD) and ulcerative colitis (UC), in a subject in need thereof comprising administering to said subject a therapeutically effective amount of a multispecific antigen binding protein, a bispecific antibody or a pharmaceutical composition as disclosed herein. In a particular aspect there is provided a method for the treatment of IBD in a subject in need thereof comprising administering to said subject a therapeutically effective amount of a multispecific antigen binding protein, a bispecific antibody or a pharmaceutical composition as disclosed herein. In an even more particular aspect, there is provided a method for the treatment of Crohn's disease and/or ulcerative colitis in a subject in need thereof comprising administering to said subject a therapeutically effective amount of a multispecific antigen binding protein, a bispecific antibody or a pharmaceutical composition as disclosed herein.

In a further aspect, there is provided a multispecific antigen binding protein, a bispecific antibody or a pharmaceutical composition of the present disclosure for use in the treatment of disease.

In an aspect there is provided a multispecific antigen binding protein, a bispecific antibody or a pharmaceutical composition of the present disclosure for use in the treatment of an immunoinflammatory disease.

In a further aspect there is provided a multispecific antigen binding protein, a bispecific antibody or a pharmaceutical composition of the present disclosure for use in the treatment of an immunoinflammatory disease selected from the group consisting of celiac disease, multiple sclerosis, atopic dermatitis, giant cell arteritis, rheumatoid arthritis, psoriasis, psoriatic arthritis, Behcet's disease and inflammatory bowel disease (IBD), including Crohn's disease (CD) and ulcerative colitis (UC). In particular there is provided a multispecific antigen binding protein, a bispecific antibody or a pharmaceutical composition of the present disclosure for use in the treatment of IBD. Even more particularly there is provided a multispecific antigen binding protein, a bispecific antibody or a pharmaceutical composition of the present disclosure for use in the treatment of Crohn's disease and/or ulcerative colitis.

In an embodiment, a multispecific antigen binding protein, in particular a bispecific antibody, of the disclosure is used as a 1st line therapy in the treatment of an immunoinflammatory disease, such as IBD. In an embodiment, a multispecific antigen binding protein, in particular a bispecific antibody, of the disclosure is used as a 2nd line therapy in the treatment of an immunoinflammatory disease, such as IBD. In an embodiment, a multispecific antigen binding protein, in particular a bispecific antibody, of the disclosure is used as a 3rd line therapy in the treatment of an immunoinflammatory disease, such as IBD.

In an embodiment there is provided a multispecific antigen binding protein or bispecific antibody comprising an IL-18 binding domain and an IL-23 binding domain wherein, said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and wherein said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15, for use in the treatment of an immunoinflammatory disease selected from the group consisting of celiac disease, multiple sclerosis, atopic dermatitis, giant cell arteritis, rheumatoid arthritis, psoriasis, psoriatic arthritis, Behcet's disease and inflammatory bowel disease (IBD), including Crohn's disease (CD) and ulcerative colitis (UC).

In an embodiment there is provided a multispecific antigen binding protein or bispecific antibody comprising an IL-18 binding domain and an IL-23 binding domain wherein:
i) said IL-18 binding domain comprises a heavy chain comprising CDRH1 (SEQ ID NO:2), CDRH2 (SEQ ID NO:3), and CDRH3 (SEQ ID NO:4), and having 95% or greater identity to SEQ ID NO: 55 and a light chain comprising CDRL1 (SEQ ID NO:5), CDRL2 (SEQ ID NO:6), and CDRL3 (SEQ ID NO:7), and having 95% or greater identity to SEQ ID NO: 57; and wherein
ii) said IL-23 binding domain comprises a heavy chain comprising CDRH1 (SEQ ID NO:10), CDRH2 (SEQ ID NO:11), and CDRH3 (SEQ ID NO:12), and having 95% or greater identity to SEQ ID NO: 54 and a light chain comprising CDRL1 (SEQ ID NO:13), CDRL2 (SEQ ID NO:14), and CDRL3 (SEQ ID NO:15), and having 95% or greater identity to SEQ ID NO: 56; for use in the treatment of an immunoinflammatory disease selected from the group consisting of multiple sclerosis, atopic dermatitis, rheumatoid arthritis, psoriasis, psoriatic arthritis and inflammatory bowel disease (IBD) including Crohn's disease (CD) and ulcerative colitis (UC).

In an embodiment there is provided a multispecific antigen binding protein or bispecific antibody comprising an IL-18 binding domain and an IL-23 binding domain wherein: said IL-18 binding domain comprises a heavy chain of SEQ ID NO: 55 and a light chain of SEQ ID NO:57 and said IL-23 binding domain comprises a heavy chain of SEQ ID NO: 54, and a light chain of SEQ ID NO: 56 for use in the treatment of an immunoinflammatory disease selected from the group consisting of celiac disease, multiple sclerosis, atopic dermatitis, giant cell arteritis, rheumatoid arthritis, psoriasis, psoriatic arthritis, Behcet's disease and inflammatory bowel disease (IBD), including Crohn's disease (CD) and ulcerative colitis (UC).

In an embodiment there is provided a multispecific antigen binding protein or bispecific antibody comprising an IL-18 binding domain and an IL-23 binding domain wherein, said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and wherein said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15, for use in the treatment of IBD.

In an embodiment there is provided a multispecific antigen binding protein or bispecific antibody comprising an IL-18 binding domain and an IL-23 binding domain wherein:

i) said IL-18 binding domain comprises a heavy chain comprising CDRH1 (SEQ ID NO:2), CDRH2 (SEQ ID NO:3), and CDRH3 (SEQ ID NO:4), and having 95% or greater identity to SEQ ID NO: 55 and a light chain comprising CDRL1 (SEQ ID NO:5), CDRL2 (SEQ ID NO:6), and CDRL3 (SEQ ID NO:7), and having 95% or greater identity to SEQ ID NO: 57; and wherein ii) said IL-23 binding domain comprises a heavy chain comprising CDRH1 (SEQ ID NO:10), CDRH2 (SEQ ID NO:11), and CDRH3 (SEQ ID NO:12), and having 95% or greater identity to SEQ ID NO: 54 and a light chain comprising CDRL1 (SEQ ID NO:13), CDRL2 (SEQ ID NO:14), and CDRL3 (SEQ ID NO:15), and having 95% or greater identity to SEQ ID NO: 56; for use in the treatment of IBD.

In an embodiment there is provided a multispecific antigen binding protein or bispecific antibody comprising an IL-18 binding domain and an IL-23 binding domain wherein: said IL-18 binding domain comprises a heavy chain of SEQ ID NO: 55 and a light chain of SEQ ID NO:57 and said IL-23 binding domain comprises a heavy chain of SEQ ID NO: 54, and a light chain of SEQ ID NO: 56 for use in the treatment of IBD.

In an embodiment there is provided a multispecific antigen binding protein or bispecific antibody comprising an IL-18 binding domain and an IL-23 binding domain wherein, said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and wherein said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15, for use in the treatment of Crohn's disease and/or ulcerative colitis.

In an embodiment there is provided a multispecific antigen binding protein or bispecific antibody comprising an IL-18 binding domain and an IL-23 binding domain wherein:

i) said IL-18 binding domain comprises a heavy chain comprising CDRH1 (SEQ ID NO:2), CDRH2 (SEQ ID NO:3), and CDRH3 (SEQ ID NO:4), and having 95% or greater identity to SEQ ID NO: 55 and a light chain comprising CDRL1 (SEQ ID NO:5), CDRL2 (SEQ ID NO:6), and CDRL3 (SEQ ID NO:7), and having 95% or greater identity to SEQ ID NO: 57; and wherein ii) said IL-23 binding domain comprises a heavy chain comprising CDRH1 (SEQ ID NO:10), CDRH2 (SEQ ID NO:11), and CDRH3 (SEQ ID NO:12), and having 95% or greater identity to SEQ ID NO: 54 and a light chain comprising CDRL1 (SEQ ID NO:13), CDRL2 (SEQ ID NO:14), and CDRL3 (SEQ ID NO:15), and having 95% or greater identity to SEQ ID NO: 56; for use in the treatment of Crohn's disease and/or ulcerative colitis.

In an embodiment there is provided a multispecific antigen binding protein or bispecific antibody comprising an IL-18 binding domain and an IL-23 binding domain wherein: said IL-18 binding domain comprises a heavy chain of SEQ ID NO: 55 and a light chain of SEQ ID NO:57 and said IL-23 binding domain comprises a heavy chain of SEQ ID NO: 54, and a light chain of SEQ ID NO: 56 for use in the treatment of Crohn's disease and/or ulcerative colitis.

Further provided is the use of a multispecific antigen binding protein, a bispecific antibody, or a pharmaceutical composition disclosed herein in the manufacture of a medicament for use in the treatment of a disease, optionally wherein the disease is an immunoinflammatory disease. Further provided is the use of a multispecific antigen binding protein, a bispecific antibody, or a pharmaceutical composition disclosed herein in the manufacture of a medicament for use in the treatment of IBD. Further provided is the use of a multispecific antigen binding protein, a bispecific antibody, or a pharmaceutical composition disclosed herein in the manufacture of a medicament for use in the treatment of Crohn's disease and/or ulcerative colitis.

Embodiments are further described in the subsequent numbered clauses:

1. A multispecific antigen binding protein comprising an interleukin 18 (IL-18) binding domain and an interleukin 23 (IL-23) binding domain.

2. The multispecific antigen binding protein of clause 1 wherein said IL-18 binding domain binds to human IL-18 and said IL-23 binding domain binds to human IL-23.

3. The multispecific antigen binding protein of clause 1 or clause 2 wherein said IL-23 binding domain binds to human IL-23-p19.

4. The multispecific antigen binding protein of clauses 1-3 wherein said IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7.

5. The multispecific antigen binding protein of clauses 1-3 wherein said IL-23 binding domain comprises the following CDRs:

a. CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15;

b. CDRH1 of SEQ ID NO: 18, CDRH2 of SEQ ID NO: 19, CDRH3 of SEQ ID NO: 20, CDRL1 of SEQ ID NO: 21, CDRL2 of SEQ ID NO: 22 and CDRL3 of SEQ ID NO: 23;

c. CDRH1 of SEQ ID NO: 26, CDRH2 of SEQ ID NO: 27, CDRH3 of SEQ ID NO: 28, CDRL1 of SEQ ID NO: 29, CDRL2 of SEQ ID NO: 30 and CDRL3 of SEQ ID NO: 31;

d. CDRH1 of SEQ ID NO: 34, CDRH2 of SEQ ID NO: 35, CDRH3 of SEQ ID NO: 36, CDRL1 of SEQ ID NO: 37, CDRL2 of SEQ ID NO: 38 and CDRL3 of SEQ ID NO: 39; or e. CDRH1 of SEQ ID NO: 58, CDRH2 of SEQ ID NO: 59, CDRH3 of SEQ ID NO: 60, CDRL1 of SEQ ID NO: 61, CDRL2 of SEQ ID NO: 62 and CDRL3 of SEQ ID NO: 63.

6. The multispecific antigen binding protein of clause 5 wherein said IL-23 binding domain comprises the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15.

7. The multispecific antigen binding protein of any preceding clause wherein said multispecific antigen binding protein comprises an IL-18 binding domain comprising the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7 and an IL-23 binding domain comprising the following CDRs: CDRH1 of SEQ ID NO: 10, CDRH2 of SEQ ID NO: 11, CDRH3 of SEQ ID NO: 12, CDRL1 of SEQ ID NO: 13, CDRL2 of SEQ ID NO: 14 and CDRL3 of SEQ ID NO: 15.

8. The multispecific antigen binding protein of clauses 1-7 wherein said IL-18 binding domain comprises a VH domain comprising a sequence at least 90% identical or at least 95% identical to SEQ ID NO: 8 and/or a VL domain comprising a sequence at least 90% identical or at least 95% identical to SEQ ID NO: 9.

9. The multispecific antigen binding protein of clauses 1-7 wherein said IL-23 binding domain comprises:
   a. a VH domain comprising a sequence at least 90% identical or at least 95% identical to SEQ ID NO: 16 and/or a VL domain comprising a sequence at least 90% identical or at least 95% identical to SEQ ID NO: 17;
   b. a VH domain comprising a sequence at least 90% identical or at least 95% identical to SEQ ID NO: 24 and/or a VL domain comprising a sequence at least 90% identical or at least 95% identical to SEQ ID NO: 25;
   c. a VH domain comprising a sequence at least 90% identical or at least 95% identical to SEQ ID NO: 32 and/or a VL domain comprising a sequence at least 90% identical or at least 95% identical to SEQ ID NO: 33;
   d. a VH domain comprising a sequence at least 90% identical or at least 95% identical to SEQ ID NO: 40 and/or a VL domain comprising a sequence at least 90% identical or at least 95% identical to SEQ ID NO: 41; or
   e. a VH domain comprising a sequence at least 90% identical or at least 95% identical to SEQ ID NO: 64 and/or a VL domain comprising a sequence at least 90% identical or at least 95% identical to SEQ ID NO: 65.

10. The multispecific antigen binding protein of clause 9 wherein said IL-23 binding domain comprises a VH domain comprising a sequence at least 90% identical or at least 95% identical to SEQ ID NO: 16 and a VL domain comprising a sequence at least 90% identical or at least 95% identical to SEQ ID NO: 17.

11. The multispecific antigen binding protein of clauses 1-10 wherein said multispecific antigen binding protein comprises:
   i. an IL-18 binding domain comprising a VH domain comprising a sequence at least 90% identical or at least 95% identical to SEQ ID NO: 8 and a VL domain comprising a sequence at least 90% identical or at least 95% identical to SEQ ID NO: 9; and
   ii. an IL-23 binding domain comprising a VH domain comprising a sequence at least 90% identical or at least 95% identical to SEQ ID NO: 16 and a VL domain comprising a sequence at least 90% identical or at least 95% identical to SEQ ID NO: 17.

12. The multispecific antigen binding protein of any clauses 1-7 wherein said IL-18 binding domain comprises a VH domain of SEQ ID NO: 8 and a VL domain of SEQ ID NO: 9.

13. The multispecific antigen binding protein of any of clauses 1-7 wherein said IL-23 binding domain comprises:
   a. a VH domain of SEQ ID NO: 16 and a VL domain of SEQ ID NO: 17;
   b. a VH domain of SEQ ID NO: 24 and a VL domain of SEQ ID NO: 25;
   c. a VH domain of SEQ ID NO: 32 and a VL domain of SEQ ID NO: 33;
   d. a VH domain of SEQ ID NO: 40 and a VL domain of SEQ ID NO: 41; or
   e. a VH domain of SEQ ID NO: 64 and a VL domain of SEQ ID NO: 65.

14. The multispecific antigen binding protein of clause 13 wherein said IL-23 binding domain comprises a VH domain of SEQ ID NO: 16 and a VL domain of SEQ ID NO: 17.

15. The multispecific antigen binding protein of clauses 1-14 wherein said multispecific antigen binding protein comprises:
   i. an IL-18 binding domain comprising a VH domain of SEQ ID NO: 8 and a VL domain of SEQ ID NO: 9; and
   ii. an IL-23 binding domain comprising a VH domain of SEQ ID NO: 16 and a VL domain of SEQ ID NO: 17.

16. The multispecific antigen binding protein of any preceding clause comprising an Fc domain.

17. The multispecific antigen binding protein of clause 16 wherein the Fc domain comprises a half-life extending mutation of set of mutations.

18. The multispecific antigen binding protein of clause 16 or clause 17 wherein the Fc domain comprises M252Y, S254T and T256E.

19. The multispecific antigen binding protein of clause 16 wherein the Fc domain has reduced effector function.

20. The multispecific antigen binding protein of clause 16 wherein said Fc domain comprises the amino acid substitutions L235A and G237A (EU index numbering).

21. The multispecific antigen binding protein of clause 16 wherein the Fc domain comprises Azymetric Fc mutations, optionally wherein said Azymetric Fc mutations comprise one or more mutations that drive heavy chain dimerization.

22. The multispecific antigen binding protein according to clauses 1-21 wherein said multispecific antigen binding protein comprises:
   a. a heavy chain of SEQ ID NO:42, a light chain of SEQ ID NO: 44, a heavy chain of SEQ ID NO: 43, and a light chain of SEQ ID NO:45;
   b. a heavy chain of SEQ ID NO:47, a light chain of SEQ ID NO: 49, a heavy chain of SEQ ID NO: 46, and a light chain of SEQ ID NO:48;
   c. a heavy chain of SEQ ID NO:50, a light chain of SEQ ID NO: 52, a heavy chain of SEQ ID NO: 51, and a light chain of SEQ ID NO:53; or
   d. a heavy chain of SEQ ID NO: 54, a light chain of SEQ ID NO: 56, a heavy chain of SEQ ID NO: 55, and a light chain of SEQ ID NO:57.

23. The multispecific antigen binding protein of clause 22 wherein said multispecific antigen binding protein comprises a heavy chain of SEQ ID NO: 54, a light chain of SEQ ID NO: 56, a heavy chain of SEQ ID NO: 55, and a light chain of SEQ ID NO:57.

24. The multispecific antigen binding protein according to clause 1-21 wherein said multispecific antigen binding protein comprises:
   a. an IL-18 binding domain having a heavy chain of SEQ ID NO: 42 and a light chain of SEQ ID NO:44 and an IL-23 binding domain having a heavy chain of SEQ ID NO: 43, a light chain of SEQ ID NO: 45;
   b. an IL-18 binding domain having a heavy chain of SEQ ID NO: 47 and a light chain of SEQ ID NO:49 and an IL-23 binding domain having a heavy chain of SEQ ID NO: 46, a light chain of SEQ ID NO: 48;
   c. an IL-18 binding domain having a heavy chain of SEQ ID NO: 50 and a light chain of SEQ ID NO:52 and an IL-23 binding domain having a heavy chain of SEQ ID NO: 51, a light chain of SEQ ID NO: 53; or
   d. an IL-18 binding domain having a heavy chain of SEQ ID NO: 55 and a light chain of SEQ ID NO:57 and an IL-23 binding domain having a heavy chain of SEQ ID NO: 54, a light chain of SEQ ID NO: 56.

25. The multispecific antigen binding protein of clause 24 wherein said multispecific antigen binding protein comprises an IL-18 binding domain having a heavy chain of SEQ ID NO: 55 and a light chain of SEQ ID NO:57 and an IL-23 binding domain having a heavy chain of SEQ ID NO: 54, a light chain of SEQ ID NO: 56.

26. The multispecific antigen binding protein of any preceding clause wherein said multispecific antigen binding protein is a bispecific antigen binding protein.

27. The multispecific antigen binding protein of clause 26 wherein said bispecific antigen binding protein is a bispecific antibody, optionally wherein said bispecific antibody is a Het-mAb.

28. The multispecific antigen binding protein of any preceding clause wherein said multispecific antigen binding protein down-regulates CXCL13 secretion.

29. The multispecific antigen binding protein of clause 28 wherein said multispecific antigen binding protein down-regulates CXCL13 secretion by greater than 10%, greater than 15%, greater than 20%, greater than 25%, greater than 30%, greater than 35%, greater than 40% or greater than 45% compared to a negative control antigen binding protein.

30. An anti-IL-18 and anti-IL-23 bispecific antibody comprising anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7 and anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15.

31. The anti-IL-18 and anti-IL-23 bispecific antibody of clause 30 wherein said anti-IL-18 comprises a VH domain of SEQ ID NO: 8 and a VL domain of SEQ ID NO: 9 and wherein said anti-IL-23 comprises a VH domain of SEQ ID NO: 16 and a VL domain of SEQ ID NO: 17.

32. An anti-IL-18 and anti-IL-23 bispecific antibody, comprising:
   a. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15; wherein the anti-IL-18 heavy chain has a sequence identity of 95% or greater to SEQ ID NO: 42, the anti-IL-18 light chain has a sequence identity of 95% or greater to SEQ ID NO:44, the anti-IL-23 heavy chain has a sequence identity of 95% or greater to SEQ ID NO:43, and the anti-IL-23 light chain has a sequence identity of 95% or greater to SEQ ID NO: 45.
   b. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15; wherein the anti-IL-18 heavy chain has a sequence identity of 95% or greater to SEQ ID NO: 47, the anti-IL-18 light chain has a sequence identity of 95% or greater to SEQ ID NO:49, the anti-IL-23 heavy chain has a sequence identity of 95% or greater to SEQ ID NO:46, and the anti-IL-23 light chain has a sequence identity of 95% or greater to SEQ ID NO: 48.
   c. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:18, CDRH2 of SEQ ID NO:19, CDRH3 of SEQ ID NO:20, CDRL1 of SEQ ID NO:21, CDRL2 of SEQ ID NO:22 and CDRL3 of SEQ ID NO:23; wherein the anti-IL-18 heavy chain has a sequence identity of 95% or greater to SEQ ID NO: 50, the anti-IL-18 light chain has a sequence identity of 95% or greater to SEQ ID NO:52, the anti-IL-23 heavy chain has a sequence identity of 95% or greater to SEQ ID NO:51, and the anti-IL-23 light chain has a sequence identity of 95% or greater to SEQ ID NO: 53.
   d. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7; anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15; wherein the anti-IL-18 heavy chain has a sequence identity of 95% or greater to SEQ ID NO: 55, the anti-IL-18 light chain has a sequence identity of 95% or greater to SEQ ID NO:57, the anti-IL-23 heavy chain has a sequence identity of 95% or greater to SEQ ID NO:54, and the anti-IL-23 light chain has a sequence identity of 95% or greater to SEQ ID NO:56.

33. The anti-IL-18 and anti-IL-23 bispecific antibody according to clause 32 comprising:
   i. anti-IL-18 having the following CDRs: CDRH1 of SEQ ID NO:2, CDRH2 of SEQ ID NO:3, CDRH3 of SEQ ID NO:4, CDRL1 of SEQ ID NO:5, CDRL2 of SEQ ID NO:6 and CDRL3 of SEQ ID NO:7;
   ii. anti-IL-23 having the following CDRs: CDRH1 of SEQ ID NO:10, CDRH2 of SEQ ID NO:11, CDRH3 of SEQ ID NO:12, CDRL1 of SEQ ID NO:13, CDRL2 of SEQ ID NO:14 and CDRL3 of SEQ ID NO:15;
   iii. an Fc region comprising M252Y, S254T and T256E; and wherein
   the anti-IL-18 heavy chain has a sequence identity of 95% or greater to SEQ ID NO: 55, the anti-IL-18 light chain has a sequence identity of 95% or greater to SEQ ID NO:57, the anti-IL-23 heavy chain has a sequence identity of 95% or greater to SEQ ID NO:54, and the anti-IL-23 light chain has a sequence identity of 95% or greater to SEQ ID NO:56.

34. The anti-IL-18 and anti-IL-23 bispecific antibody of clause 32 or clause 33 wherein the Fc region further comprises the amino acid substitutions L235A and G237A (EU index numbering).

35. The anti-IL-18 and anti-IL-23 bispecific antibody according to clauses 32-34, wherein the anti-IL-18 heavy chain sequence is that of SEQ ID NO: 55, the anti-IL-18 light chain sequence is that of SEQ ID NO: 57, the anti-IL-23 heavy chain sequence is that of SEQ ID NO: 54, and the anti-IL-23 light chain sequence is that of SEQ ID NO:56.

36. A bispecific antibody comprising an IL-18 binding domain and a domain comprising a means for specifically binding IL-23.

37. The bispecific antibody of clause 36 wherein the IL-18 binding domain comprises the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7

38. The bispecific antibody of clause 36 or clause 37 wherein the IL-18 binding domain comprises a VH domain comprising a sequence at least 90% identical to SEQ ID NO: 8 and a VL domain comprising a sequence at least 90% identical to SEQ ID NO: 9.

39. The bispecific antibody of clause 38 wherein the IL-18 binding domain comprises a VH domain comprising SEQ ID NO: 8 and a VL domain comprising SEQ ID NO: 9.

40. The bispecific antibody of clauses 36-39 wherein the means for specifically binding IL-23 binds to human IL23-p19.

41. The bispecific antibody of clauses 36-40 wherein the means for specifically binding IL-23 comprises a VH domain and a VL domain.

42. The bispecific antibody of any of clauses 36-41 wherein the means for specifically binding IL-23 has an equilibrium affinity of at least 600 pM at 25° C. as measured by surface plasmon resonance.

43. A bispecific antibody comprising:
   i. an IL-18 binding domain comprising the following CDRs: CDRH1 of SEQ ID NO: 2, CDRH2 of SEQ ID NO: 3, CDRH3 of SEQ ID NO: 4, CDRL1 of SEQ ID NO: 5, CDRL2 of SEQ ID NO: 6 and CDRL3 of SEQ ID NO: 7; and,
   ii. a means for specifically binding a human IL-23 protein.

44. The bispecific antibody of clause 43 wherein the means for specifically binding human IL-23 has an equilibrium affinity of at least 600 pM at 25° C. as measured by surface plasmon resonance.

45. The bispecific antibody of clause 43 or clause 44 wherein the bispecific antibody is a Het-mAb.

46. The bispecific antibody of clauses 43-45 wherein the bispecific antibody is an IgG1κ antibody.

47. The bispecific antibody of clause 46 wherein the IgG1 Fc portion is mutated at the sequences corresponding to the canonocial IgG1 framework at each of the following positions: M252Y, S254T, and T256E.

48. The bispecific antibody of clause 47 wherein the Fc region further comprises the amino acid substitutions L235A and G237A.

49. The bispecific antibody of clauses 43-48 wherein the means for specifically binding a human IL-23 protein comprises a VH domain and a VL domain.

50. The bispecific antibody of clause 49 wherein the VH domain of the means for specifically binding a human IL-23 comprises SEQ ID NO: 16, SEQ ID NO: 24, SEQ ID NO: 32, SEQ ID NO: 40 or SEQ ID NO: 64.

51. The bispecific antibody of clause 49 wherein the VL domain of the means for specifically binding a human IL-23 comprises SEQ ID NO: 17, SEQ ID NO: 25, SEQ ID NO: 33, SEQ ID NO: 41 or SEQ ID NO: 65.

52. A Het-mAb format bispecific antibody comprising an IL-18 binding domain comprising a VH domain according to SEQ ID NO: 8 and a VL domain according to SEQ ID NO: 9, an IgG1 Fc domain, and a means for specifically binding to human IL-23.

53. The Het-mAb format bispecific antibody of clause 52 wherein the means for specifically binding to human IL-23 has an equilibrium affinity of at least 600 pM at 25° C. as measured by surface plasmon resonance.

54. A nucleic acid sequence encoding the multispecific antigen binding protein of clauses 1-29 or the bispecific antibody of clauses 30-53.

55. A nucleic acid sequence encoding any one, two, three or all four of the following amino acid sequences: a heavy chain of SEQ ID NO: 54, a light chain of SEQ ID NO: 56, a heavy chain of SEQ ID NO: 55, and a light chain of SEQ ID NO:57.

56. An expression vector comprising the nucleic acid sequence(s) of clause 54 or clause 55.

57. A recombinant host cell comprising the nucleic acid sequence(s) according to clause 54 or clause 55 or the expression vector(s) according to clause 56.

58. A method for the production of a multispecific antigen binding protein, said method comprising culturing the recombinant host cell according to clause 57 under conditions suitable for expression of said nucleic acid sequence(s) or vector(s), whereby said multispecific antigen binding protein is produced.

59. A multispecific antigen binding protein produced by the method of clause 58.

60. A cell line engineered to express the multispecific antigen binding protein according to any one of clauses 1-29 or the bispecific antibody according to any one of clauses 30-53.

61. A pharmaceutical composition comprising the multispecific antigen binding protein according to any one of clauses 1-29 or the bispecific antibody according to any one of clauses 30-53 and a pharmaceutically acceptable excipient.

62. A method for the treatment of disease in a subject in need thereof comprising administering to said subject a therapeutically effective amount of the multispecific antigen binding protein according to any one of clauses 1-29, the bispecific antibody according to any one of clauses 30-53, or the pharmaceutical composition according to clause 61.

63. A method for the treatment of an immunoinflammatory disease in a subject in need thereof comprising administering to said subject a therapeutically effective amount of the multispecific antigen binding protein according to any one of clauses 1-29, the bispecific antibody according to any one of clauses 30-53, or the pharmaceutical composition according to clause 61.

64. A method for the treatment of inflammatory bowel disease (IBD) in a subject in need thereof comprising administering to said subject a therapeutically effective amount of the multispecific antigen binding protein according to any one of clauses 1-29, the bispecific antibody according to any one of clauses 30-53, or the pharmaceutical composition according to clause 61.

65. A method for the treatment of Crohn's disease and/or ulcerative colitis in a subject in need thereof comprising administering to said subject a therapeutically effective amount of the multispecific antigen binding protein according to any one of clauses 1-29, the bispecific antibody according to any one of clauses 30-53, or the pharmaceutical composition according to clause 61.

66. The multispecific antigen binding protein according to any one of clauses 1-29, the bispecific antibody according to any one of clauses 30-53, or a pharmaceutical composition according to clause 61 for use in the treatment of disease.

67. The multispecific antigen binding protein according to any one of clauses 1-29, the bispecific antibody according to any one of clauses 30-53, or a pharmaceutical composition according to clause 61 for use in the treatment of an immunoinflammatory disease.

68. The multispecific antigen binding protein according to any one of clauses 1-29, the bispecific antibody according to any one of clauses 30-53, or a pharmaceutical composition according to clause 61 for use in the treatment of IBD.

69. The multispecific antigen binding protein according to any one of clauses 1-29, the bispecific antibody according to any one of clauses 30-53, or a pharmaceutical composition according to clause 61 for use in the treatment of Crohn's disease and/or ulcerative colitis.

70. The method of clauses 62-65 or the multispecific antigen binding protein, bispecific antibody or pharmaceutical composition according to clause 66-69 wherein the subject is a human subject.

71. Use of a multispecific antigen binding protein according to any one of clause 1-29, a bispecific antibody according to any one of clauses 30-53, or a pharmaceutical composition according to clause 61 in the manufacture of a medicament for use in the treatment of a disease, optionally wherein the disease is an immunoinflammatory disease.

72. Use of a multispecific antigen binding protein according to any one of clause 1-29, a bispecific antibody according to any one of clauses 30-53, or a pharmaceutical composition according to clause 61 in the manufacture of a medicament for use in the treatment of IBD.

73. Use of a multispecific antigen binding protein according to any one of clause 1-29, a bispecific antibody according to any one of clauses 30-53, or a pharmaceutical composition according to clause 61 in the manufacture of a medicament for use in the treatment of Crohn's disease and/or ulcerative colitis.

The invention is further illustrated by the following non-limiting examples.

EXAMPLES

Antibody Details

In the Examples section below, the following bispecific antibodies (bsAbs) are described (see table 1a):

TABLE 1a

| Heterodimeric bsAbs | | |
|---|---|---|
| Identifier | Description | SEQ ID NO (Heavy Chain/Light Chain) |
| Heterodimeric bsAb 1 | Anti-IL-18 mAb on ZA and anti-IL-23 mAb (risankizumab) on ZB heterodimeric bsAb plus Fc and silencing mutations | HC1: 42 HC2: 43 LC1: 44 LC2: 45 |
| Heterodimeric bsAb 2 | Anti-IL-23 mAb (risankizumab) on ZA and anti-IL-18 mAb on ZB heterodimeric bsAb plus Fc and silencing mutations | HC1: 46 HC2: 47 LC1: 48 LC2: 49 |
| Heterodimeric bsAb 3 | Anti-IL-18 mAb on ZA and anti-IL-23 mAb (tildrakizumab) on ZB heterodimeric bsAb plus Fc and silencing mutations | HC1: 50 HC2: 51 LC1: 52 LC2: 53 |
| Heterodimeric bsAb 4 | Anti-IL-23 mAb (risankizumab) on ZA and anti-IL-18 mAb on ZB heterodimeric bsAb plus Fc, silencing and half life extending mutations | HC1: 54 HC2: 55 LC1: 56 LC2: 57 |

In the Examples section below, the following control antibodies are described (see table 1b):

TABLE 1b

| Control antibodies | |
|---|---|
| Identifier | Description |
| IL-18 control 1 | Anti-IL-18 mAb (VH = SEQ ID NO: 8, VL = SEQ ID NO: 9) plus Het-mAb Fc mutations of Heterodimeric bsAbs 1-4, silencing (LAGA) and half-life extending (YTE) mutations |
| IL-18 control 2 | Anti-IL-18 mAb (VH = SEQ ID NO: 8, VL = SEQ ID NO: 9) |
| IL-18 control 3 | Anti-IL-18 mAb plus Het-mAb Fc mutations of Heterodimeric bsAbs 1-4 |
| IL-18 control 4 | Anti-IL-18 mAb (VH = SEQ ID NO: 8, VL = SEQ ID NO: 9) plus Het-mAb Fc mutations of Heterodimeric bsAbs 1-4 and half-life extending (YTE) mutations. |
| IL-18 control 5 | Anti-IL-18 (VH = SEQ ID NO: 8, VL = SEQ ID NO: 9) mAb plus Het-mAb Fc mutations of Heterodimeric bsAbs 1-4 and silencing (LAGA) mutations. |

TABLE 1b-continued

| Control antibodies | |
|---|---|
| Identifier | Description |
| IL-23 control 1 | Anti-IL-23 (VH = SEQ ID NO: 16, VL = SEQ ID NO: 17, risankizumab) mAb plus Het-mAb Fc mutations of Heterodimeric bsAbs 1-4, silencing (LAGA) and half-life extending (YTE) mutations. |
| IL-23 control 2 | Anti-IL-23 (VH = SEQ ID NO: 16, VL = SEQ ID NO: 17, risankizumab) mAb plus Het-mAb Fc mutations of Heterodimeric bsAbs 1-4, and silencing (LAGA) mutations |
| IL-23 control 3 | Anti-IL-23 (VH = SEQ ID NO: 24, VL = SEQ ID NO: 25, tildrakizumab) plus Het-mAb Fc mutations of Heterodimeric bsAbs 1-4, and half-life extending (YTE) mutations |
| IL-23 control 4 | Anti-IL-23 (VH = SEQ ID NO: 16, VL = SEQ ID NO: 17, risankizumab) mAb plus Het-mAb Fc mutations of Heterodimeric bsAbs 1-4. |
| Negative control 1 | Anti-RSV mAb plus Het-mAb Fc mutations of Heterodimeric bsAbs 1-4. |
| Negative control 2 | Anti-RSV mAb plus half-life extending (YTE) mutations. |
| Negative control 3 | Anti-RSV mAb |

Example 1: Expression, Purification and Quality Control

Common light chain and heterodimeric bispecific 1-3 antibodies were expressed transiently in HEK293 6E cells using BalanCD HEK293 media (Irvine Scientific) and purified from filtered supernatants by Protein A affinity chromatography (MabSelect SuRE resin or MagSepharose PrismA magnetic beads, Cytiva) followed by size exclusion chromatography 15 (Superdex S200, Cytiva). Standard precautions for minimising endotoxin contamination were maintained at each stage of the purifications, and all preparations were filter sterilised by vacuum filtration (0.2 µM). Heterodimeric bsAb 4 was stably expressed in CHO cells and purified using similar conditions.

The proportion of high molecular weight (HMW), low molecular weight (LMW) and monomer species within each bispecific sample were characterised by analytical size-exclusion chromatography (aSEC). Samples were analysed on an Agilent 1260 Infinity (Agilent, UK) with DAD detector running Chemstation software (Agilent, UK). The bispecific sample composition was characterised by reversed-phase liquid chromatography mass spectrometry (RP-LCMS). The samples were deglycosylated with PNGase F and separated using an acetonitrile gradient (supplemented with trifluoracetic acid and acetic acid) on a Waters Acquity HPLC system (Waters, UK). The column eluate was analysed by UV detector and directed to an on-line Waters Synapt G2-Si mass spectrometer (Waters, UK). UV data and ESI mass spectra were processed together using Protein Metrics Intact Mass software (Protein Metrics Inc, USA) to provide semi-quantitative species proportions.

TABLE 2

| Analysis of antibody batch | | | | |
|---|---|---|---|---|
| | Analytical SEC | | | RP-LCMS |
| Molecule | HMW (%) | Monomer (%) | LMW (%) | Correct Bispecific (%) |
| Heterodimeric bsAb 1 | 0 | 96.6 | 4.4 | 91 |
| Heterodimeric bsAb 2 | 1.8 | 97.4 | 0.8 | 97 |
| Heterodimeric bsAb 3 | 0.5 | 99.5 | 0 | 90 |
| Heterodimeric bsAb 4 | 0 | 100 | 0 | 99.4 |

Examples 2 and 3: Binding of Heterodimeric bsAb to Human and Cynomolgus Monkey (Cyno) IL-18 and IL-23

A heterodimeric bsAb, alongside anti-IL-18 and anti-IL-23 common light chain control bispecific antibodies, were assessed for binding to human and cyno IL-18 and IL-23, using the Biacore 8K and T200 (Cytiva) surface plasmon resonance (SPR) instruments. All reagents were generated recombinantly in-house with the exception of Rhesus monkey IL-18 which was purchased from R&D systems (Cat #2548-RM-025/CF). Rhesus and cynomolgus monkey amino acid sequences are identical. Therefore, the protein will be referred to as cynomolgus monkey IL-18.

Heterodimeric bsAb, anti-IL-18 and anti-IL-23 common light chain bispecific control molecules were assessed for binding to recombinant human and cynomolgus monkey IL-18 and IL-23 using the Biacore 8K and T200 (Cytiva) SPR instruments. The antibodies were captured onto Protein A/G, which was immobilised onto flow cell 2 of 8 channels (Biacore 8K) or flow cells 2, 3 and 4 (Biacore T200) of a CM5 series S sensor chip by primary amine coupling. The IL-18 or IL-23 analytes were passed over the captured antibodies at varying concentrations between 0.04-25 nM. The association phase was for 240 seconds at 30 µl/min, followed by a dissociation step of up to 1200 seconds. A 0 nM (i.e., buffer alone) injection was used to double reference the binding curves. Regeneration of the chip surface between cycles was carried out using 50 mM NaOH. The assay was run at 25° C. in HBS-EP$^+$ buffer. Biacore 8K control software version 3.0 was used to run the experiment. Data was analysed using Biacore 8K Insight evaluation software version 3.0. Biacore T200 control software version 1.0 was used to run the experiment. Data was analysed using Biacore T200 evaluation software version 2.0. Affinities and kinetics were determined using the 1:1 kinetic fit inherent to the software where possible. All affinity values generated using both instruments were combined to determine geometric mean values.

Table 3 shows the affinities for heterodimeric bsAb 1-3 and relevant control antibodies to human and cyno IL-18 and IL-23, whilst table 4 shows the affinities for heterodimeric bsAb 4 and relevant control antibodies to human and cyno IL-18 and IL-23. Results indicate that the heterodimeric bsAbs have comparable affinities (within 2-fold) for binding to human and cyno IL-18 and IL-23 as the relevant control molecules.

TABLE 3

Binding of heterodimeric bsAbs to recombinant human
and cynomolgus monkey IL 23 and IL-18 using SPR.

| | Human IL-18 KD (pM) | Human IL-23 KD (pM) |
|---|---|---|
| Heterodimeric bsAb 1 | <10 | 374 |
| Heterodimeric bsAb 2 | <10 | 158 |
| Heterodimeric bsAb 3 | <10 | 499 |
| IL-23 control 2 | NB | 163 |
| IL-23 control 3 | NB | 576 |
| IL-18 control 5 | <10 | NB |

Key: Affinity values are n = 1. KD = Affinity; NB = No binding; SPR = surface plasmon resonance.

TABLE 4

Binding of heterodimeric bsAb-4 to recombinant human
and cynomolgus monkey IL-23 and IL-18 using SPR.

| | Human IL-18 Average KD (pM) | Cyno IL-18 Average KD (pM) | Human IL-23 Average KD (pM) | Cyno IL-23 Average KD (pM) |
|---|---|---|---|---|
| Heterodimeric bsAb-4 | 35 | 68 | 297 | 162 |
| IL-23 control 1 | NB | NB | 348 | 204 |
| IL-18 control 1 | 67 | 64 | NB | NB |

Key: Affinity values are the geometric mean of n = 3-5 replicates. Cyno = cynomolgus monkey; KD = Affinity; NB = No binding; SPR = surface plasmon resonance.

Example 4: Dual Engagement of Heterodimeric bsAb 4 with Recombinant Human IL-23 and IL-18 Using BLI Dual engagement of a heterodimeric bsAb with human IL-23 and human IL-18 was determined using a binding assay on the Sartorius Octet RED384 biolayer interferometry (BLI) instrument.

Human IL-18 at 200 nM was captured onto anti-Penta His dip and read biosensors for 240 seconds. The loaded sensors were dipped into either heterodimeric bsAb 4 (diluted to 20 µg/ml in PBSF) or PBSF for 240 seconds. Following which, the sensors were dipped into PBSF or human IL-23 (diluted to 200 nM in PBSF) or PBSF for 240 seconds. The sensors were then dipped back into buffer for the dissociation phase for 240 seconds. Blank sensors were included to check for non-specific binding of the proteins to the sensors. Regeneration of the biosensor tips was carried out using 10 mM glycine pH1.5. The analysis was run at 25° C., with a plate shaker speed of 1000 rpm. Data were aligned to the baseline, but no kinetics model was applied to the data.

There was no non-specific binding of the proteins to the anti-Penta His sensors or of human IL-23 to human IL-18. Simultaneous binding of heterodimeric bsAb 4 to human IL-23 and IL-18 was successfully confirmed (see table 5).

TABLE 5

Dual engagement of heterodimeric bsAb-4 with
recombinant human IL-23 and IL-18 using BLI.

| Sensor loading | Association 1 | Association 2 | Binding |
|---|---|---|---|
| Human IL-23 | Heterodimeric bsAb 4 | Human IL-18 | Binding |
| Human IL-23 | Buffer | Human IL-18 | No binding |
| Buffer | Heterodimeric bsAb 4 | Human IL-18 | No binding |
| Buffer | Buffer | Human IL-18 | No binding |

Example 5: Potency Against IL-23: DB Assay

DB cells are a diffuse B lymphoblast cell line. This assay quantifies the ability of anti-IL-23 molecules to neutralise IL-23 binding and activation of IL-23 receptor, by measuring the phosphorylated STAT3 (pSTAT3) levels from DB cells in response to IL-23R activation. Effective neutralising antibodies would disrupt the IL-23 interaction with IL-23R and lead to decreased pSTAT3 levels.

The pSTAT3 MSD assay was used to test the ability of heterodimeric bsAb to neutralise IL-23 induced pSTAT3 signalling in the DB cell line. For the neutralising study 6.52 pM-3328 pM heterodimeric bsAb (or control molecules) were pre-incubated with 3200 pM human IL-23 in a 1:1 ratio for 15 minutes at room temperature. Following the pre-incubation, 25 µl of antibody-antigen complex was added per well to a V-bottom 96 well plate (Greiner). Additionally, either 25 µl media alone or 25 µl media containing 800 pM human IL-18 was added to control wells as a negative/positive control. Final assay concentrations were 1.63 pM-832 pM heterodimeric bsAb/control mAbs and 800 pM human IL-23. To the preincubated mAbs or control wells, 25 µl of DB cells ($0.75 \times 10^6$ cells) were added and incubated for a further 15 minutes at room temperature. Post incubation, 25 µl of 1× cell lysis buffer containing 2 mM PMSF (Cell Signalling technologies) was added to the cells and incubated on ice for 15 minutes. Lysed cells were stored overnight at −20° C. before detection of the pSTAT3 signal from 40 µl of cell lysate using a standard MSD pSTAT3 detection kit (K150SVD-4; Meso Scale Discovery).

Raw data was generated on the MSD plate reader. Raw MSD counts were exported as a delimited text file, and further analysis performed in ActivityBase, derived pIC50 values were obtained from each independent experiment, and the geometric mean was calculated between these values, along with the range. The calculated geometric means and ranges of pIC50 values were converted to picomolar using the following formula: $IC50 \ (pM)=10^{-pIC50} * 10^{12}$.

Heterodimeric bsAb-4 was found to neutralise human IL-23 with a mean IC50 between 4 replicates of 59 pM. The IL-23 control 1 molecule had a mean IC50 between 4 replicates of 16 pM. The negative control 2 and IL-18 control 1 molecules were found to be inactive in this assay as expected (Table 6).

TABLE 6

Human IL-23 neutralisation of heterodimeric
bsAb 4 and control antibodies

| Ab | PIC50 (Geomean) | PIC50 (Range) | IC50 pM (Geomean) | IC50 pM (Range) |
|---|---|---|---|---|
| Heterodimeric bsAb 4 | 10.23 | 10.06-10.60 | 58.88 | 25-87 |
| IL-23 control 1 | 10.78 | 10.60-10.97 | 16.60 | 10-25 |
| Negative control 2 | N/A | N/A | N/A | N/A |
| IL-18 control 1 | N/A | N/A | N/A | N/A |

Example 6: Potency Against IL-18: KG-1 Assay

KG-1 cells are immortalised human macrophages, and express IL-18 receptor on the cell surface, which can be upregulated by stimulation with TNFa. Binding of IL-18 to IL-18 receptor leads to receptor dimerisation and activation, recruitment of kinase protein and downstream activation of NFkB. NFkB upregulates expression of interferon gamma, which is secreted from the cells, and can be detected in supernatants using a sandwich immunoassay, specific for interferon gamma.

The binding of an antibody to IL-18 in this system disrupts the interaction between the cytokine and its receptor, which in turn prevents the IL-18 mediated secretion of interferon gamma. The interferon gamma present in the supernatants can be normalised to assay wells which contain IL-18 alone, and assay wells which contain no IL-18 to determine percentage inhibition. These values can then be used to plot a 4-point logistical curve fit, which enable determination of molecule potency (IC50).

KG-1 cells were dispensed into a 96-well flat-bottom plate and stimulated with 10 ng/mL human TNFa (GRITS48613) in full media (IMDM (Gibco 21980-032)+ 10% FBS (Gibco 10100-147)) overnight at 37 C, 5% CO2.

Human IL-18 or Cynomolgus IL-18 (R&D Systems 2548-RM-025/CF) were prepared to a concentration of 333 pM in full media. 50 uL of this IL-18 preparation was dispensed into all columns of a 96-well flat-bottom plate (Corning 3596), with the exception of column 11. 50 uL full media was dispensed into column 11.

Tested antibodies were prepared to a concentration of 13.3 nM in full media in a 96-well V-bottom plate (Greiner 651201) and were serially diluted 1:3 over 10 points. Columns 11 and 12 had full media added alone. 50 uL from this plate was transferred into the flat-bottom plate containing human IL-18. This plate was incubated for 30 minutes at room temperature on an orbital rocker to allow the antibodies to pre-complex with IL-18.

Plates containing TNFa-stimulated KG-1 cells were collected from the incubator, and contents were transferred to a 96-well U-bottom plate prior to centrifugation at 1500 rpm for 5 minutes. Spent media was discarded and cell pellets were resuspended in 100 uL full media to wash, and plates were centrifuged as before. Spent media was discarded and cell pellets were resuspended in 100 uL full media. Cell suspensions were transferred to the plate containing antibodies and IL-18. The plate was returned to the incubator overnight at 37 C, 5% CO2.

One plate from an MSD interferon gamma immunoassay kit (MSD K151AEB) was obtained, and 150 uL of MSD Blocker B (1% w/v MSD Blocker B powder in TC-grade PBS) was dispensed into each well of the plate. The plate was covered with an aluminium foil seal and was incubated at room temperature on an orbital rocker for 1 hour. Following this incubation, the plate was washed three times with PBS+0.1% Tween-20 using the BioTek ELX405U plate washer. Cell plates prepared on the previous day were obtained from the incubator, contents were transferred to a 96-well U-bottom plate and were centrifuged at 1500 rpm for 5 minutes. 25 uL of supernatant was aspirated from each well using the Integra ViaFlo and were dispensed into the MSD plate. The plate was sealed as before and incubated at room temperature on an orbital rocker for 1 hour. The interferon gamma detection antibody was diluted from 50× stock to 1× by adding 60 uL to 2.94 mL of Diluent 100 from the kit. The plate was washed 3 times as before, and 25 uL detection antibody solution was dispensed into each well. The plate was sealed as before and incubated at room temperature on an orbital rocker for 1 hour. Following this incubation, the plate was washed as before. 2× Read Buffer T was prepared from a 4× Read Buffer T stock (MSD R92TC) by diluting 2-fold in dH2O and 150 uL was dispensed per well, and the plate was read on the MSD Sector S 600 imager.

Raw data was generated on the MSD Sector S 600 imager using MSD Workbench (MSD). Raw MSD counts were exported as a delimited text file, and further analysis was performed in ActivityBase for human and cynomolgus IL-18 neutralisation data, respectively.

Mean pIC50 values were obtained from each independent experiment, and the geometric mean was calculated between these values, along with the range. The calculated geometric mean pIC50 value for each antibody was converted to picomolar using the following formula: IC50 (pM)= $10^{-pIC50}*10^{12}$.

In these experiments, heterodimeric bsAbs were tested alongside control molecules and negative control 1 (see Tables 7 and 8). Heterodimeric bsAb 4 was found to neutralise human IL-18 with a mean IC50 between 3 true replicates of 114.82 pM. The IL-18 control 1 was observed to have a small increase in potency, with a mean IC50 between 3 true replicates of 52.48 pM (Table 8). Heterodimeric bsAb 4 was found to neutralise cynomolgus IL-18 with a mean IC50 between 3 true replicates of 97.72 pM. The IL-18 control 1 was observed to have a small increase in potency, with a mean IC50 between 3 true replicates of 53.70 pM (Table 9). The IL-23 control 1 and negative control 1 were found to be inactive in this assay, demonstrating no neutralisation of human or cynomolgus IL-18.

TABLE 7

Human IL-18 Neutralisation potency by heterodimeric bsAb 1-3 and control antibodies

| Identifier | pIC50 (GeoMean) | pIC50 (Range) | IC50 (pM, Mean) |
|---|---|---|---|
| Heterodimeric bsAb 1 | 9.88 | 0.18 | 132.74 |
| Heterodimeric bsAb 2 | 10.11 | 0.11 | 77.62 |
| Heterodimeric bsAb 3 | 9.98 | 0.13 | 104.71 |
| IL-18 control 5 | 10.28 | 0.19 | 52.48 |
| IL-18 control 2 | 10.39 | 0.19 | 41.02 |
| IL-23 control 2 | <8.48 | 0 | Inactive |

TABLE 8

Human IL-18 Neutralisation potency by heterodimeric bsAb 4 and control antibodies

| Identifier | pIC50 (GeoMean) | pIC50 (Range) | IC50 (pM, Mean) |
|---|---|---|---|
| Heterodimeric bsAb 4 | 9.94 | 0.04 | 114.82 |
| IL-23 control 1 | <8.48 | 0 | Inactive |
| IL-18 control 1 | 10.28 | 0.05 | 52.48 |
| IL-18 control 2 | 10.40 | 0.02 | 39.81 |
| Negative control 1 | <8.48 | 0 | Inactive |

TABLE 9

| | pIC50 | pIC50 | IC50 |
|---|---|---|---|
| Identifier | (GeoMean) | (Range) | (pM, Mean) |
| Heterodimeric bsAb 4 | 10.01 | 0.07 | 97.72 |
| IL-23 control 1 | <8.48 | 0 | Inactive |
| IL-18 control 1 | 10.27 | 0.11 | 53.70 |
| IL-18 control 2 | 10.19 | 0 | 64.57 |
| Negative control 1 | <8.48 | 0 | Inactive |

Cynomolgus IL-18 Neutralisation potency by heterodimeric bsAb 4 and control antibodies

Example 7. Inhibition of IFNγ Production by Heterodimeric bsAbs in LPS+IL-12 Stimulated Human Whole Blood Materials and Methods: All human samples were obtained with patient informed consent under a protocol approved by a national, regional or investigational centre ethics committee or an Institutional Review Board (IRB) approved protocol. On the day of the assay, 10× solutions of the antibodies, LPS (10 ug/mL), and recombinant human IL-12 (500 pg/mL) were prepared. Serial dilutions (1:3) from the top 10× concentration (10 ug/mL) of the antibodies were prepared. A 96-well flat bottom plate (Falcon 353072) was prepared by adding 20 uL LPS, IL-12, or antibody solutions to the appropriate wells. 140 uL of human whole blood was added to each well to a final assay volume of 200 uL. PBS was added where needed to reach a final assay volume of 200 uL. The plates were gently mixed and incubated at 37° C. with 5% $CO_2$ for 6h. Following the incubation period, 100 uL of PBS was added to each well and the plates were centrifuged at 2000 rpm for 5 min. The supernatants were transferred to a 96-well round bottom plate and stored at −20° C. To quantify IFNγ in the supernatants, the plates were thawed to room temperature and applied to a human IFNγ detection plate (K151AEB-2) following manufacturer's protocol (Meso Scale Discovery). Molarity for the antibodies was calculated using the equation: M=g/L×1/MW, where the molecular weight=150 kD. pIC50 was calculated using the equation pIC50=−log(IC50), where IC50 is in molar concentration. IFNγ concentrations were normalized to the mean negative control 3 response (representing 100%, or 1.0) on each assay plate. The normalized data were pooled across donors and antibodies, and dose-response (four-parameter logistic) curves for each antibody were fit with a shared min, max, and slope across antibodies for every donor, and a shared change in antibody IC50 across donors. For every antibody, donor-level IC50s were estimated from the fitted curves; mean IC50 estimates across donors were calculated by taking the geometric mean while 95% confidence intervals were constructed using the t-distribution and standard deviations calculated from donor-level IC50s. Additionally, an IC50 fold change estimate between Heterodimeric bsAbs and IL-18 controls and 95% confidence interval was obtained from the fitted model. All analyses were performed using the statistical programming language R, version 4.0.3.

Results: Table 10 shows IL-18 control 3 and different Heterodimeric bsAbs inhibited IFNγ secretion at 6 hours in a concentration dependent manner.

TABLE 10

IC50 summary of LPS + IL12-induced IFN-γ inhibition by IL-18 control 3 and Heterodimeric bsAbs in human whole blood.

| Heterodimeric bsAbs | Parent | IC50 Heterodimeric bsAbs* (nM) | IC50 Parent* (nM) | IC50 Heterodimeric bsAbs (% of Parent) | Lower 95% CL | Upper 95% CL | P-Value ** |
|---|---|---|---|---|---|---|---|
| Heterodimeric bsAb-1 | IL-18 control 3 | 16.0 | 8.4 | 190.9 | 158.9 | 229.4 | <0.0001 |
| Heterodimeric bsAb-2 | IL-18 control 3 | 18.2 | 7.6 | 240.4 | 189.0 | 305.7 | <0.0001 |
| Heterodimeric bsAb-3 | IL-18 control 3 | 21.7 | 7.8 | 279.7 | 229.1 | 341.4 | <0.0001 |

FIG. 1 shows IL-18 control 1 inhibited IFNγ secretion at 6 hours in a concentration dependent manner with an estimated IC50=5.5 nM with 95% CI (3.2 nM-9.3 nM). Heterodimeric bsAb-4 inhibited IFNγ secretion in a concentration dependent manner with an estimated IC50=10.5 nM with 95% CI (6.2 nM-17.7 nM). The IC50 results for the LPS+IL-12 stimulated whole blood secretion of IFNγ are summarized in Table 11.

TABLE 11

IC50 summary of LPS + IL12-induced IFN-γ inhibition by IL-18 control 1 and Heterodimeric bsAb-4 in human whole blood.

| Identifier | pIC50 | pIC50 (95% CI) | IC50 nM | IC50 nM (95% CI) | Fold change (from IL-18 control 1) (95% CI) |
|---|---|---|---|---|---|
| IL-18 control 1 | 8.3 | 8.5-8.0 | 5.5 | 3.2-9.3 | — |
| Heterodimeric bsAB-4 | 8.0 | 8.2-7.8 | 10.5 | 6.2-17.7 | 1.9 (1.5-2.4) |

Example 8. Inhibition of IL-23 Induced pSTAT3 in Healthy Human Whole Blood

Materials and Method: Blood was withdrawn from healthy volunteers by venepuncture and transferred into a vacutainer tube spray coated with sodium heparin. All human samples were obtained with patient informed consent under a protocol approved by a national, regional or investigational centre ethics committee or an Institutional Review Board (IRB) approved protocol. Each whole blood container (BD Bioscience 367874) was inverted gently 2-3 times to ensure even suspension and 100 μl whole blood was immediately added to each assay well. Serial dilutions (1:3) from the top concentration (10 μg/mL) were prepared. Recombinant IL-23 [2.16 ng/mL] was made up to 4× final assay concentration in culture medium and 50 μl was added to each assay well and mixed by gentle pipetting. After gently pipetting, plates were incubated at 37° C. for 15 min. 2 mL of pre-warmed 1× lyse/fix buffer (BD Bioscience 558049) was added to each well and incubated at 37° C. for 15 mins. Cells were then pelleted by centrifugation and washed with 2 mL Dulbecco's Phosphate-Buffered Salt Solution (DPBS). After wash in DPBS, cells were transferred to a 96-well culture plate and again pelleted by centrifugation and resuspended in 0.2 mL BD Phosflow Perm buffer III (BD Biosciences 558050) and incubated for 30 min on ice. After permeabilization, cells were washed in DPBS and pelleted by centrifugation, followed by addition of 25 μl of FcR mined by defining positive cells (pSTAT3+) from fluorescence minus one (FMO)-PE controls that were batch applied to all samples. Unstimulated recombinant IL-23 treatments alone and negative control 3 were included as controls. Data were background corrected and normalized to the mean "no mAb" control response (representing 100% or 1.0) and the mean unstimulated response (representing 0% or 0) on each assay plate. The normalized data were pooled across donors and antibodies and dose-response (four-parameter logistic) curves for every antibody and donor were fit with a shared min, max, and slope between antibodies for every donor, and a shared difference between antibody IC50s across donors. For each antibody, donor-level IC50s were estimated from the fitted curves, from which mean IC50 estimates across donors were calculated by taking an inverse-variance weighted geometric mean. 95% confidence intervals for the mean IC50s were derived from random effect meta-analyses of donor-level IC50s. Additionally, an IC50 fold change between Heterodimeric bsAbs and IL-23 controls and 95% confidence interval (CI) was estimated from the fitted model. All analyses were performed using the statistical programming language R, version 4.0.3.

Results: For each donor, the percentage of pSTAT3+ cells was normalized to the mean of whole blood samples treated with rhIL-23 alone (no mAb) and to the mean of the unstimulated samples. The data presented in Table 12 demonstrate the efficacy of Heterodimeric bsAbs in blocking STAT3 phosphorylation downstream of IL-23 stimulation.

TABLE 12

IC50 summary of IL-23-induced pSTAT3 inhibition by IL-23 controls and Heterodimeric bsAbs in T cells.

| Heterodimeric bsAbs | Parent | IC50 Heterodimeric bsAbs* (pM) | IC50 Parent* (pM) | IC50 Heterodimeric bsAbs (% of Parent) | Lower 95% CL | Upper 95% CL | P-Value ** |
|---|---|---|---|---|---|---|---|
| Heterodimeric bsAb-1 | IL-23 control 2 | 615 | 282 | 218.4 | 176.5 | 270.2 | 0.0000 |
| Heterodimeric bsAb-2 | IL-23 control 2 | 711 | 286 | 249.0 | 202.8 | 305.7 | 0.0000 |
| Heterodimeric bsAb-3 | IL-23 control 3 | 640 | 637 | 100.5 | 79.2 | 127.6 | 0.9659 |

*Geometric means across donors;
** Test of IC50 equality, Parent vs Heterodimeric bsAbs.

block reagent mix (Invitrogen 14-9161-73) and incubated on ice for 10 minutes followed by surface staining. The surface staining cocktail mastermix was prepared including the conjugated anti-CD3 (Biolegend 300448), anti-CD161 (Miltenyi Biotec 130-113-590) and anti-pSTAT3 (BD Biosciences 612569) antibodies in the flow cytometric staining buffer. 50 μl staining cocktail was added to the blocking reagent in each reaction well, pipetted to ensure mixing and incubated at room temperature for 60 minutes. Following incubation, reactions were topped with 200 μl staining buffer and pelleted by centrifugation. Cell pellets were resuspended in 200 μl staining buffer and stored at 4° C. until analysis by flow cytometry. Sample data was acquired using the BD LSR Fortessa flow cytometer with BD FACSDiva™ software (v9.0) and analyzed using the FlowJo software (v 10).

For pSTAT3 analysis, the gating strategy included doublet exclusion, size exclusion followed by gating on CD3+ CD161+ cells. Gating parameters for pSTAT3 were deter- The same recombinant IL-23 stimulated human whole blood assay was established to compare the potency of the Heterodimeric bsAb-4, to the parent IL-23 control 1. For each donor, the percentage of pSTAT3+ cells was normalized to the mean of whole blood samples treated with rhIL-23 alone (no mAb) and to the mean of the unstimulated samples. Individual dose response curves were generated to visualize the shift in potency observed for Heterodimeric bsAb-4 (FIG. 2).

To estimate potency, the data were pooled across all donors and dose-response (four parameter logistic) curves for each antibody were fit as described in Method section above. Table 13 shows IL-23 control 1 inhibited IL-23-induced pSTAT3 with an estimated IC50=163.3 pM with 95% CI (138.2 pM-192.8 pM). Heterodimeric bsAb-4 inhibited pSTAT3 with an estimated IC50=394.9 pM with 95% CI (334.5 pM-466.2 pM). The data presented here demonstrate the efficacy of Heterodimeric bsAb-4 in blocking STAT3 phosphorylation downstream of IL-23 stimulation.

TABLE 13

IC50 summary of IL-23-induced pSTAT3 inhibition by IL-23 control 1 and
Heterodimeric bsAb-4 in T cells. IC50 summary of IL-23-induced pSTAT3
inhibition by IL-23 control 1 and Heterodimeric bsAb-4 in T cells.
IC50 estimates for each antibody are reported with 95% confidence intervals
(CIs). A fold change estimate between Heterodimeric bsAb and IL-23
control potencies is provided (ratio of IC50 estimates).

| Antibody | pIC50 | pIC50 (95% CI) | IC50 nM | IC50 nM (95% CI) | Fold change (from anti-IL-23) |
|---|---|---|---|---|---|
| IL-23 Control 1 | 9.8 | 9.86-9.71 | 163.3 | 138.2-192.8 | — |
| Heterodimeric bsAb 4 | 9.4 | 9.48-9.33 | 394.9 | 334.5-466.2 | 2.42 |

Example 9: Inhibition of Cytokine Production by
Heterodimeric bsAb-4 in Mouse Splenocytes
Stimulated with Recombinant IL-23

Materials and Methods: On the day of the assay, 4×
solutions of the antibodies and recombinant human IL-23
were prepared. 250 ul of rhIL-23 was combined with 250 ul
of each antibody and incubated at 37 C for 60 minutes in
96-well deep well plates (Greiner BioOne 780271-D).
Recombinant human IL-23 was used at final concentration
of 2 ng/ml. Antibodies were used at 3 ug/ml at the top dose
and serial dilutions were made from top dose. Mouse
splenocytes were counted and brought up to 400K cells/100
ul in RPMI/10% FBS/10 ng/ml mouse IL-2. Splenocytes
were plated at 400K/well (100 ul) onto 96 well round bottom
plate (Falcon 353077) leaving the outer edges empty. Outer
wells were filled with 200 ul of sterile dPBS (Gibco 14190-
144). After 1 hour antibody/IL-23 incubation, 100 ul/well
IL-23/Ab mix was added to designated wells containing
preplated 400K mouse splenocytes and incubated at 37
C/5% CO2 for 72 hours. After 72 hours, the plates contain-
ing cells were then centrifuged at 400×g for 5 min to prevent
any floating cells from being taken. Supernatant (120 ul) was
then transferred to a clean 96 well polypropylene plate and min, max, and slope across antibodies for every experiment,
and a shared difference between antibody IC50s across
experiments. For each antibody, experiment-level IC50s
were estimated from the fitted curves, from which mean
IC50 estimates across experiments were calculated by taking
an inverse-variance weighted geometric mean. 95% confi-
dence intervals for the mean IC50s were derived from
random effect meta-analyses of experiment-level IC50s.
Additionally, an IC50 fold change estimate between Het-
erodimeric bsAb and IL-23 control 1 with 95% confidence
interval (CI) was obtained from the fitted model. All analy-
ses were performed using the statistical programming lan-
guage R, version 4.0.3.

Results: Individual dose response curves with shared min
and max across antibodies for every experiment were gen-
erated to visualize the shift in potency observed for Het-
erodimeric bsAb-4 (FIG. 3). To estimate potency, the data
were pooled across all experiments and dose-response (four
parameter logistic) curves for each antibody were fit as
described in Methods. Data for Heterodimeric bsAbs 1-3 (in
terms of IL-17A inhibition) are shown below in Table 14.
The data presented in Table 14 demonstrate the efficacy of
Heterodimeric bsAbs in blocking IL17A secretion down-
stream of IL-23 stimulation.

TABLE 14

IC50 summary of IL-23-induced mouse IL-17A inhibition by IL-23
controls and Heterodimeric bsAbs in mouse splenocytes.

| Heterodimeric bsAbs | Parent | IC50 Heterodimeric bsAb* (pM) | IC50 Parent* (pM) | IC50 Heterodimeric bsAb (% of Parent) | Lower 95% CL | Upper 95% CL | P-Value ** |
|---|---|---|---|---|---|---|---|
| Heterodimeric bsAb-1 | IL-23 control 2 | 153.3 | 60.0 | 253.9 | 182.8 | 352.6 | 0.0000 |
| Heterodimeric bsAb-2 | IL-23 control 2 | 146.7 | 53.3 | 274.1 | 192.6 | 390.3 | 0.0000 |
| Heterodimeric bsAb-3 | IL-23 control 3 | 2673.3 | 686.7 | 387.4 | 219.7 | 683.1 | 0.0000 |

*% changes reported between Heterodimeric bsAbs and Parent controls are representative for all data combined from studies
on different days. 100 refers to equality between Parent and Heterodimeric bsAbs.

tested for mouse IL-17A by MSD IL-17A U-Plex kit (MSD
K152UTK-4) following the manufacturer's protocol.

IL-17A concentrations were normalized to the mean "no
antibody" control response (representing 100%, or 1.0) on
each assay plate. The normalized data were pooled across
experiments and antibodies, and dose-response (four-param-
eter logistic) curves for each antibody were fit with a shared Table 15 below shows IL-23 control 1 inhibited IL-23-
induced IL-17A secretion with an estimated IC50=41.7 pM
with 95% CI (26.6 pM-65.4 pM). Heterodimeric bsAb-4
inhibited IL-23-induced IL-17A secretion with an estimated
IC50=111.3 pM with 95% CI (70.8 pM-175.0 pM).

TABLE 15

IC50 summary of IL-23-induced mouse IL-17A inhibition by IL-23
control 1 and Heterodimeric bsAb-4 in mouse splenocytes.

| Antibody | pIC50 (M) | pIC50 (95% CI) | IC50 PM | IC50 PM (95% CI) | Fold change (from anti-IL-23) |
|---|---|---|---|---|---|
| IL-23 Control 1 | 10.4 | 10.6-10.2 | 41.7 | 26.6-65.4 | — |
| Heterodimeric bsAb 4 | 10.0 | 10.2-9.8 | 111.3 | 70.8-175.0 | 2.67 |

Example 10. Impact of Heterodimeric bsAb on IL12-Induced Interferon Gamma Release from NK92 Cells Material and Methods: A cell suspension of unmodified human natural killer lymphoma cells (NK-92 cells) were transferred to a 50 ml conical tube pre-filled with culture media (alpha-MEM, 10% heat inactivated FBS, 10% horse serum, glutamax, penicillin-streptomycin, 20 uM of folic acid, 0.2 mM of inositol, recombinant human IL-2 at 10 ng/ml, and 0.1% of 50 mM 2-Mercaptoethanol), centrifuged (500 rpm for 5 minutes), and counted on the Vi-cell XR Cell Viability Analyzer.

NK-92 cells were resuspended in culture media at $0.5 \times 10^6$ cells/ml. Antibody dilutions of ustekinumab, Heterodimeric bsAbs, IL-23 control 1 and IL-18 control 1, and negative control 3 were prepared at 4× the required final concentration in culture media; 50 µl of prepared dilutions of antibody was added in the wells of a 96-well U bottom polystyrene plate. Human recombinant IL-12 was prepared at 4× the final concentration in culture media; 50 µl of prepared 4× recombinant IL-12 was added for a final concentration of 0.6 ng/ml. Culture medium was added in the appropriate wells. Antibodies (negative control 3) and IL-12 were pre-incubated for one hour at 37° C. (5% C02). Cells (100 µl) were added in the wells, at 50,000 cells/100 µl. The final volume is 200 µl. The plate was shaken at 600 rpm for 30 seconds to mix all reagents and incubated at 37° C. (5% C02).

After 24 hours incubation, the plate was centrifuged at 1200 rpm for 5 minutes and the supernatants were removed without disturbing the pellets and transferred to a new 96-well U-bottom plate. Supernatants were either used for MSD cytokine assay immediately after harvesting or stored at –80° C. until further use.

Results: The anti-IL12/23p40 selective antibody Ustekinumab inhibited IL-12 induced IFNγ secretion in a concentration dependent manner. As shown in FIG. 4, Heterodimeric bsAb-4, IL-23 control 1 and IL-18 control 1 show no activity (NA) in inhibiting IFNγ secretion. As shown in Table 16, Ustekinumab inhibited IFNγ secretion in a dose-dependent manner with an estimated IC50=0.13 ug/mL (molecular weight=148.6 kDa, IC50=875 pM). Therefore, inhibition of IL-12/23 activity by Heterodimeric bsAb-4 was not detected in this assay.

TABLE 16

IC50 summary of IL-12-induced IFNγ inhibition
by Heterodimeric bsAb-4, IL-18 control 1, IL-23
control 1, and Ustekinumab in NK-92 cells.

| Antibody | IC50 (ug/mL) | IC50 ug/mL (CI) | IC50 (pM) |
|---|---|---|---|
| IL-23 Control 1 | NA | NA | NA |
| IL-18 Control 1 | NA | NA | NA |

TABLE 16-continued

IC50 summary of IL-12-induced IFNγ inhibition
by Heterodimeric bsAb-4, IL-18 control 1, IL-23
control 1, and Ustekinumab in NK-92 cells.

| Antibody | IC50 (ug/mL) | IC50 ug/mL (CI) | IC50 (pM) |
|---|---|---|---|
| Heterodimeric bsAb-4 | NA | NA | NA |
| Ustekinumab | 0.13 | 0.07-0.18 | 875 |

Example 11. Impact of Heterodimeric bsAb-4 on Cytokine and Chemokine Profiles in a Myeloid-T Cell Co-Culture System Materials and Methods: Prior to the start of the assays, CD14+ monocytes were differentiated with GM-CSF for 6 days into M0 macrophages and immature dendritic cells (GM-CSF differentiated CD14+ cells). Cells were harvested and frozen into aliquots for use in future experiments. One day prior to start of the assay, GM-CSF-differentiated CD14+ cells were thawed and cultured overnight at 37 C in a humidified 5% $CO_2$ incubator. On the day of the assay, GM-CSF-differentiated CD14+ cells were harvested and diluted to a 4× concentration. Pan CD3+ T cells were thawed and diluted to a 2× concentration. A 4× mixture of anti-CD3 (4 ng/mL, final concentration=1 ng/mL), recombinant human IL-18 (2 ng/mL, final concentration=0.5 ng/mL), peptidoglycan (PGN, 40 ug/mL, final concentration=10 ug/mL), and antibodies was made in a polypropylene staging plate and incubated for 30 minutes prior to addition to assay plate. The antibodies used were: negative control 2 at 5 ug/mL and 10 ug/mL, anti-IL-18 antibody (IL-18 control 3) at 5 ug/mL, anti-IL-23 antibody (IL-23 control 1) at 5 ug/mL, anti-IL-23×IL-18 HETmAb (Heterodimeric bsAb-4) at 10 ug/mL and a combination of IL-23 control 1 at 5 ug/mL and IL-18 control 3 at 5 ug/mL antibodies. 5 ug/mL negative control 2 was the appropriate control for 5 ug/mL IL-18 control 3 and 5 ug/mL IL-23 control 1. 10 ug/mL negative control 2 was the appropriate control for 10 ug/mL Heterodimeric bsAb-4 and the combination of 5 ug/mL IL-18 control 3 and 5 ug/mL IL-23 control 1 (total of 10 ug/mL in this treatment condition).

Each 96-well plate was a different T cell donor while CD14+ cells all came from the same donor. Each T cell donor had 2 identical 96-well plates: one plate for day 2 collection, and the second plate for day 6 collection. 4,500 differentiated CD14+ myeloid cells (in 50 uL of 4× concentrated cell resuspension) were added to appropriate wells in a U-bottom polystyrene 96-well plate. 40,000 pan CD3+ T cells (in 100 µL of 2× concentrated cell resuspension) were added to appropriate wells in a U-bottom polystyrene 96-well plate. 50 uL of 4× mixture of anti-CD3, recombinant human IL-18, PGN, and antibodies were added to appropriate wells in a U-bottom polystyrene 96-well plate. The final volume of each well was 200 uL. The plates were incubated for either 2 or 6 days at 37 C in a humidified 5% $CO_2$ incubator.

Following incubation for either 2 or 6 days, 96-well plates were spun down at 400 g for 10 minutes and supernatant was carefully aliquoted. 50 uL of supernatant was aliquoted into polypropylene U-bottom 96-well plates and stored immediately at −80C for future Nomic nPlex analysis. 60 uL supernatant aliquoted into 2 identical polypropylene U-bottom 96-well plates and stored immediately at −80C for MSD cytokine analysis.

Results: Pro-inflammatory M1 macrophages and dendritic cells (DCs) are believed to be important in orchestrating T cell polarization and activation (i.e. Th1 & Th17) through the secretion of TNFα, IL-23, IL-18 and IL-1β. In IBD patients, gut-resident T cell activation can lead to excess production of IFNγ, IL-22 & IL-17 that together with IL-23 and IL-18 contribute to disease associated pathology. To model DC-T cell interactions, a primary human immune cell co-culture assay consisting of PGN-activated CD14$^+$ myeloid cells and CD3$^+$ T cells was used to examine the impact of antibodies on Th1 and Th17 cell differentiation. CD14$^+$ monocytes were first differentiated into immature DC/macrophages (myeloid cells) following 6 days of treatment with GM-CSF. These cells were then stimulated with 10 ug/mL PGN to induce secretion of endogenous cytokines including IL-23, TNFα, IL-18 and IL-1β. In the same condition, a natural IL-18 antagonist, IL-18 binding protein (IL-18BP) was also secreted at 500 μg/ml (data not shown). Therefore, recombinant IL-18 (0.5 ng/ml) was added to the culture. Anti-CD3 (1 ng/ml) was used to promote T cell activation and Th17 cell differentiation.

In all these studies, MSD analysis demonstrates sufficient IL-23, IL-1B and IL-18 secretion by PGN-stimulated immature DC/macrophages (data not shown). IL-23 control 1 and IL-18 control 1 were used at 5 μg/ml as a single treatment or in combination. Heterodimeric bsAb-4 was used at 10 μg/ml to match the molarity of IL-23 control 1 and IL-18 control 1. Since the molecules are of equivalent size then their molarity should be equivalent. Negative control 2 was used at 0, 5 and 10 μg/ml to match concentrations of tested articles. For final data analysis, 5 μg/ml and 10 μg/ml negative control 2 were both excluded as controls because of the potential for Fc-mediated activity with negative control 2 bearing intact Fc effector function while test articles such as Heterodimeric bsAb-4 have a LAGA mutation to "silence" the Fc effector function (data not shown). Therefore, 0 μg/ml aRSV (no Ab control) was used as control for MSD and nPlex data analysis.

As shown in FIG. 5, Heterodimeric bsAb-4 retained activity of the anti-IL-23 mAb arm, as measured by inhibition of IL-17A and IL-22 secretion at day 6 in a selective assessment of 6 donors who responded to anti-IL-23×IL-18 HET mAb. Whereas anti-IL-18 (IL-18 control 1) inhibited IFNγ secretion significantly, IL-23 control 1 alone enhanced IFNγ which was unexpected. Heterodimeric bsAb-4 showed partial inhibition of IFNγ secretion compared to the anti-IL-18 arm though not statistically different compared to control. Like Heterodimeric bsAb-4, the combination of anti-IL-23 and anti-IL-18 also showed partial inhibition of IFNγ secretion though not statistically different compared to control. Since it has been well established that anti-IL-23 mAbs reduce or stabilize IFNγ pathway activity in preclinical disease models or clinical trials [Hue 2006; Hirota 2011; Sofen 2014; Visvanathan 2018], the unexpected enhancement of IFNγ seen in this co-culture system may be an artifact of this in vitro assay. Furthermore, Heterodimeric bsAb-4 blocked LPS+IL-12 induced IFNγ production in a dose-dependent manner (as shown above in Example 7) demonstrating that Heterodimeric bsAb-4 can block IL-18-dependent IFNγ production. These data suggest that molar equivalents of Heterodimeric bsAb-4 can inhibit IL-23 and IL-18 dependent effects in a complex T cell-myeloid co-culture system to either an equivalent or partial level, respectively, compared to the parental mAbs.

As shown in FIG. 6, CXCL13 is down-regulated significantly by Heterodimeric bsAb-4 and the combination of anti-IL-23 and anti-IL-18, compared to a negative control antibody. Neither the ani-IL-23 control 1 or the anti-IL-18 control 1 alone significantly decrease CXCL13. In fact, Heterodimeric bsAb-4 downregulates CXCL13 expression significantly compared to both anti-IL-23 and anti-IL-18 controls indicating a potential synergistic effect of combined blockade of IL-18 and IL-23.

| SEQUENCE LISTING | |
| --- | --- |
| SEQ ID NO | Description |
| 1 | Human IL-18 |
| 2 | CDRH1 of IL-18 Binding Domain |
| 3 | CDRH2 of IL-18 Binding Domain |
| 4 | CDRH3 of IL-18 Binding Domain |
| 5 | CDRL1 of IL-18 Binding Domain |
| 6 | CDRL2 of IL-18 Binding Domain |
| 7 | CDRL3 of IL-18 Binding Domain |
| 8 | VH IL-18 Binding Domain |
| 9 | VL IL-18 Binding Domain |
| 10 | CDRH1 of first IL-23 Binding Domain |
| 11 | CDRH2 of first IL-23 Binding Domain |
| 12 | CDRH3 of first IL-23 Binding Domain |
| 13 | CDRL1 of first IL-23 Binding Domain |
| 14 | CDRL2 of first IL-23 Binding Domain |
| 15 | CDRL3 of first IL-23 Binding Domain |
| 16 | VH first IL-23 Binding Domain |
| 17 | VL first IL-23 Binding Domain |
| 18 | CDRH1 of second IL-23 Binding Domain |
| 19 | CDRH2 of second IL-23 Binding Domain |
| 20 | CDRH3 of second IL-23 Binding Domain |
| 21 | CDRL1 of second IL-23 Binding Domain |
| 22 | CDRL2 of second IL-23 Binding Domain |
| 23 | CDRL3 of second IL-23 Binding Domain |
| 24 | VH second IL-23 Binding Domain |
| 25 | VL second IL-23 Binding Domain |
| 26 | CDRH1 of third IL-23 Binding Domain |
| 27 | CDRH2 of third IL-23 Binding Domain |
| 28 | CDRH3 of third IL-23 Binding Domain |
| 29 | CDRL1 of third IL-23 Binding Domain |
| 30 | CDRL2 of third IL-23 Binding Domain |
| 31 | CDRL3 of third IL-23 Binding Domain |
| 32 | VH third IL-23 Binding Domain |
| 33 | VL third IL-23 Binding Domain |
| 34 | CDRH1 of fourth IL-23 Binding Domain |
| 35 | CDRH2 of fourth IL-23 Binding Domain |
| 36 | CDRH3 of fourth IL-23 Binding Domain |
| 37 | CDRL1 of fourth IL-23 Binding Domain |
| 38 | CDRL2 of fourth IL-23 Binding Domain |
| 39 | CDRL3 of fourth IL-23 Binding Domain |
| 40 | VH fourth IL-23 Binding Domain |
| 41 | VL fourth IL-23 Binding Domain |
| 42 | Heterodimeric bsAb 1 HC1 (anti-IL-18) |
| 43 | Heterodimeric bsAb 1 HC2 (anti-IL-23) |
| 44 | Heterodimeric bsAb 1 LC1 (anti-IL-18) |
| 45 | Heterodimeric bsAb 1 LC2 (anti-IL-23) |
| 46 | Heterodimeric bsAb 2 HC1 (anti-IL-23) |
| 47 | Heterodimeric bsAb 2 HC2 (anti-IL-18) |
| 48 | Heterodimeric bsAb 2 LC1 (anti-IL-23) |
| 49 | Heterodimeric bsAb 2 LC2 (anti-IL-18) |
| 50 | Heterodimeric bsAb 3 HC1 (anti-IL-18) |
| 51 | Heterodimeric bsAb 3 HC2 (anti-IL-23) |
| 52 | Heterodimeric bsAb 3 LC1 (anti-IL-18) |
| 53 | Heterodimeric bsAb 3 LC2 (anti-IL-23) |

| SEQUENCE LISTING | |
| --- | --- |
| SEQ ID NO | Description |
| 54 | Heterodimeric bsAb 4 HC1 (anti-IL-23) |
| 55 | Heterodimeric bsAb 4 HC2 (anti-IL-18) |
| 56 | Heterodimeric bsAb 4 LC1 (anti-IL-23) |
| 57 | Heterodimeric bsAb 4 LC2 (anti-IL-18) |
| 58 | CDRH1 of fifth IL-23 Binding Domain |
| 59 | CDRH2 of fifth IL-23 Binding Domain |
| 60 | CDRH3 of fifth IL-23 Binding Domain |
| 61 | CDRL1 of fifth IL-23 Binding Domain |
| 62 | CDRL2 of fifth IL-23 Binding Domain |
| 63 | CDRL3 of fifth IL-23 Binding Domain |
| 64 | VH fifth IL-23 Binding Domain |
| 65 | VL fifth IL-23 Binding Domain |
| 66 | CDRH1 of second IL-18 Binding Domain |
| 67 | CDRH2 of second IL-18 Binding Domain |
| 68 | CDRH3 of second IL-18 Binding Domain |
| 69 | CDRL1 of second IL-18 Binding Domain |

| SEQUENCE LISTING | |
| --- | --- |
| SEQ ID NO | Description |
| 70 | CDRL2 of second IL-18 Binding Domain |
| 71 | CDRL3 of second IL-18 Binding Domain |
| 72 | VH second IL-18 Binding Domain |
| 73 | VL second IL-18 Binding Domain |
| 74 | Human IL23p19 |
| 75 | Human IL12B/IL12p40 |
| 76 | CDRH1 of third IL-18 Binding Domain |
| 77 | CDRH2 of third IL-18 Binding Domain |
| 78 | CDRH3 of third IL-18 Binding Domain |
| 79 | CDRL1 of third IL-18 Binding Domain |
| 80 | CDRL2 of third IL-18 Binding Domain |
| 81 | CDRL3 of third IL-18 Binding Domain |
| 82 | VH third IL-18 Binding Domain |
| 83 | VL third IL-18 Binding Domain | human IL-18

SEQ ID NO: 1

YFGKLESKLSVIRNLNDQVLFIDQGNRPLFEDMTDSDCRDNAPRTIFIISMYKDSQPRGMAVTISVKCEKISTLSCENKIISFKEM

NPPDNIKDTKSDIIFFQRSVPGHDNKMQFESSSYEGYFLACEKERDLFKLILKKEDELGDRSIMFTVQNED

CDRH1 of IL-18 Binding Domain

SEQ ID NO: 2

GYYFH

CDRH2 of IL-18 Binding Domain

SEQ ID NO: 3

RIDPEDDSTKYAERFKD

CDRH3 of IL-18 Binding Domain

SEQ ID NO: 4

WRIYRDSSGRPFYVMDA

CDRL1 of IL-18 Binding Domain

SEQ ID NO: 5

LASEDIYTYLT

CDRL2 of IL-18 Binding Domain

SEQ ID NO: 6

GANKLQD

CDRL3 of IL-18 Binding Domain

SEQ ID NO: 7

LQGSKFPLT

VH IL-18 Binding Domain

SEQ ID NO: 8

QVQLVQSGAEVKKPGASVKVSCKVSGEISTGYYFHWVRQAPGKGLEWMGRIDPEDDSTKYAERFKDRVTMTEDTSTDTAYMELSSL

RSEDTAVYYCTTWRIYRDSSGRPFYVMDAWGQGTLVTVSS

VL IL-18 Binding Domain

SEQ ID NO: 9

DIQMTQSPSSVSASVGDRVTITCLASEDIYTYLTWYQQKPGKAPKLLIYGANKLQDGVPSRFSGSGSGTDYTLTISSLQPEDFATY

YCLQGSKFPLTFGQGTKLEIK

CDRH1 of IL-23 Binding Domain

SEQ ID NO: 10

DQTIH

CDRH2 of IL-23 Binding Domain

SEQ ID NO: 11

YIYPRDDSPKYNENFKG

CDRH3 of IL-23 Binding Domain

SEQ ID NO: 12

PDRSGYAWFIY

-continued

CDRL1 of IL-23 Binding Domain

SEQ ID NO: 13

KASRDVAIAVA

CDRL2 of IL-23 Binding Domain

SEQ ID NO: 14

WASTRHT

CDRL3 of IL-23 Binding Domain

SEQ ID NO: 15

HQYSSYPFT

VH IL-23 Binding Domain

SEQ ID NO: 16

QVQLVQSGAEVKKPGSSVKVSCKASGYTFTDQTIHWMRQAPGQGLEWIGYIYPRDDSPKYNENFKGKVTITADKSTSTAYMELSSL

RSEDTAVYYCAIPDRSGYAWFIYWGQGTLVTVSS

VL IL-23 Binding Domain

SEQ ID NO: 17

DIQMTQSPSSLSASVGDRVTITCKASRDVAIAVAWYQQKPGKVPKLLIYWASTRHTGVPSRFSGSGSRTDFTLTISSLQPEDVADY

FCHQYSSYPFTFGSGTKLEIK

CDRH1 of IL-23 Binding Domain

SEQ ID NO: 18

TYWMT

CDRH2 of IL-23 Binding Domain

SEQ ID NO: 19

QIFPASGSADYNEKFEG

CDRH3 of IL-23 Binding Domain

SEQ ID NO: 20

GGGGFAY

CDRL1 of IL-23 Binding Domain

SEQ ID NO: 21

RTSENIYSYLA

CDRL2 of IL-23 Binding Domain

SEQ ID NO: 22

NAKTLAE

CDRL3 of IL-23 Binding Domain

SEQ ID NO: 23

QHHYGIPFT

VH IL-23 Binding Domain

SEQ ID NO: 24

QVQLVQSGAEVKKPGASVKVSCKASGYIFITYWMTWVRQAPGQGLEWMGQIFPASGSADYNEKFEGRVTM

TTDTSTSTAYMELRSLRSDDTAVYYCARGGGGFAYWGQGTLVTVSS

VL IL-23 Binding Domain

SEQ ID NO: 25

DIQMTQSPSSLSASVGDRVTITCRTSENIYSYLAWYQQKPGKAPKLLIYNAKTLAEGVPSRFSGSGSGTD

FTLTISSLQPEDFATYYCQHHYGIPFTFGQGTKVEIK

CDRH1 of IL-23 Binding Domain

SEQ ID NO: 26

TYWLG

CDRH2 of IL-23 Binding Domain

SEQ ID NO: 27

IMSPVDSDIRYSPSFQG

CDRH3 of IL-23 Binding Domain

SEQ ID NO: 28

RRPGQGYFDF

CDRL1 of IL-23 Binding Domain

SEQ ID NO: 29

RASQGISSWLA

CDRL2 of IL-23 Binding Domain

SEQ ID NO: 30

AASSLQS

-continued

CDRL3 of IL-23 Binding Domain

SEQ ID NO: 31

QQYNIYPYT

VH IL-23 Binding Domain

SEQ ID NO: 32

EVQLVQSGAEVKKPGESLKISCKGSGYSFTTYWLGWVRQMPGKGLDWIGIMSPVDSDIRYSPSFQGQVTMSVDKSITTAYLQWNSL

KASDTAMYYCARRRPGQGYFDFWGQGTLVTVSS

VL IL-23 Binding Domain

SEQ ID NO: 33

DIQMTQSPSSLSASVGDRVTITCRASQGISSWLAWYQQKPEKAPKSLIYAASSLQSGVPSRFSGSGSGTD

FTLTISSLQPEDFATYYCQQYNIYPYTFGQGTKLEIK

CDRH1 of IL-23 Binding Domain

SEQ ID NO: 34

NYWIG

CDRH2 of IL-23 Binding Domain

SEQ ID NO: 35

IIDPSNSYTRYSPSFQG

CDRH3 of IL-23 Binding Domain

SEQ ID NO: 36

WYYKPFDV

CDRL1 of IL-23 Binding Domain

SEQ ID NO: 37

TGSSSNIGSGYDVH

CDRL2 of IL-23 Binding Domain

SEQ ID NO: 38

GNSKRPS

CDRL3 of IL-23 Binding Domain

SEQ ID NO: 39

ASWTDGLSLVV

VH IL-23 Binding Domain

SEQ ID NO: 40

EVQLVQSGAEVKKPGESLKISCKGSGYSFSNYWIGWVRQMPGKGLEWMGIIDPSNSYTRYSPSFQGQVTI

SADKSISTAYLQWSSLKASDTAMYYCARWYYKPFDVWGQGTLVTVSSAST

VL IL-23 Binding Domain

SEQ ID NO: 41

QSVLTQPPSVSGAPGQRVTISCTGSSSNIGSGYDVHWYQQLPGTAPKLLIYGNSKRPSGVPDRFSGSKSG

TSASLAITGLQSEDEADYYCASWTDGLSLVVFGGGTKLTVL

Heterodimeric bsAb 1 HC1 (anti-IL-18)

SEQ ID NO: 42

QVQLVQSGAEVKKPGASVKVSCKVSGEISTGYYFHWVRQAPGKGLEWMGRIDPEDDSTKYAERFKDRVTMTEDTSTDTAYMELSSL

RSEDTAVYYCTTWRIYRDSSGRPFYVMDAWGQGTLVTVSSASTKGPSVFPLAPSSKSTSGGTAALGCEVTDYFPEPVTVSWNSGAL

TSGVHTFPAVLESSGLYSLSSVVTVPSSSLGTQTYICNVNHKPSNTKVDKKVEPKSCDKTHTCPPCPAPELAGAPSVFLFPPKPKD

TLMISRTPEVTCVVVDVSHEDPEVKFNWYVDGVEVHNAKTKPREEQYNSTYRVVSVLTVLHQDWLNGKEYKCKVSNKALPAPIEKT

ISKAKGQPREPQVYVYPPSRDELTKNQVSLTCLVKGFYPSDIAVEWESNGQPENNYKTTPPVLDSDGSFALVSKLTVDKSRWQQGN

VFSCSVMHEALHNHYTQKSLSLSPGK

Heterodimeric bsAb 1 HC2 (anti-IL-18)

SEQ ID NO: 43

QVQLVQSGAEVKKPGSSVKVSCKASGYTFTDQTIHWMRQAPGQGLEWIGYIYPRDDSPKYNENFKGKVTITADKSTSTAYMELSSL

RSEDTAVYYCAIPDRSGYAWFIYWGQGTLVTVSSASTKGPSVFPLAPSSKSTSGGTAALGCRVKDYFPEPVTVSWNSGALTSGVHT

FPAVLQSSGLYSLSSVVTVPSSSLGTQTYICNVNHKPSNTKVDKKVEPKSCDKTHTCPPCPAPELAGAPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAKG

QPREPQVYVLPPSRDELTKNQVSLLCLVKGFYPSDIAVEWESNGQPENNYLTWPPVLDSDGSFFLYSKLTVDKSRWQQGNVFSCSV

MHEALHNHYTQKSLSLSPGK

-continued

Heterodimeric bsAb 1 LC1 (anti-IL-18)
                                                    SEQ ID NO: 44
DIQMTQSPSSVSASVGDRVTITCLASEDIYTYLTWYQQKPGKAPKLLIYGANKLQDGVPSRFSGSGSGTDYTLTISSLQPEDFATY YCLQGSKFPLTFGQGTKLEIKRTVAAPSVFIFPPSDERLKSGTASVVCLLNNFYPREAKVQWKVDNALQSGNSQESVTEQDSKDST

YSLSSRLTLSKADYEKHKVYACEVTHQGLSSPVTKSENRGEC

Heterodimeric bsAb 1 LC2 (anti-IL-23)
                                                    SEQ ID NO: 45
DIQMTQSPSSLSASVGDRVTITCKASRDVAIAVAWYQQKPGKVPKLLIYWASTRHTGVPSRFSGSGSRTDFTLTISSLQPEDVADY FCHQYSSYPFTFGSGTKLEIKRTVAAPSVFIFPPSDEELKSGTASVECLLNNFYPREAKVQWKVDNALQSGNSQESVTEQDSKDST

YSLSSTLTLSKADYEKHKVYACEVTHQGLSSPVTKSFNRGEC

Heterodimeric bsAb 2 HC1 (anti-IL-23)
                                                    SEQ ID NO: 46
QVQLVQSGAEVKKPGSSVKVSCKASGYTFTDQTIHWMRQAPGQGLEWIGYIYPRDDSPKYNENFKGKVTITADKSTSTAYMELSSL RSEDTAVYYCAIPDRSGYAWFIYWGQGTLVTVSSASTKGPSVFPLAPSSKSTSGGTAALGCRVKDYFPEPVTVSWNSGALTSGVHT

FPAVLQSSGLYSLSSVVTVPSSSLGTQTYICNVNHKPSNTKVDKKVEPKSCDKTHTCPPCP

Heterodimeric bsAb 2 HC2 (anti-IL-18)
                                                    SEQ ID NO: 47
QVQLVQSGAEVKKPGASVKVSCKVSGEISTGYYFHWVRQAPGKGLEWMGRIDPEDDSTKYAERFKDRVTMTEDTSTDTAYMELSSL RSEDTAVYYCTTWRIYRDSSGRPFYVMDAWGQGTLVTVSSASTKGPSVFPLAPSSKSTSGGTAALGCEVTDYFPEPVTVSWNSGAL TSGVHTFPAVLESSGLYSLSSVVTVPSSSLGTQTYICNVNHKPSNTKVDKKVEPKSCDKTHTCPPCPAPELAGAPSVFLFPPKPKD TLMISRTPEVTCVVVDVSHEDPEVKFNWYVDGVEVHNAKTKPREEQYNSTYRVVSVLTVLHQDWLNGKEYKCKVSNKALPAPIEKT ISKAKGQPREPQVYVLPPSRDELTKNQVSLLCLVKGFYPSDIAVEWESNGQPENNYLTWPPVLDSDGSFFLYSKLTVDKSRWQQGN

VFSCSVMHEALHNHYTQKSLSLSPGK

Heterodimeric bsAb 2 LC1 (anti-IL-23)
                                                    SEQ ID NO: 48
DIQMTQSPSSLSASVGDRVTITCKASRDVAIAVAWYQQKPGKVPKLLIYWASTRHTGVPSRFSGSGSRTDFTLTISSLQPEDVADY FCHQYSSYPFTFGSGTKLEIKRTVAAPSVFIFPPSDEELKSGTASVECLLNNFYPREAKVQWKVDNALQSGNSQESVTEQDSKDST

YSLSSTLTLSKADYEKHKVYACEVTHQGLSSPVTKSFNRGEC

Heterodimeric bsAb 2 LC2 (anti-IL-18)
                                                    SEQ ID NO: 49
DIQMTQSPSSVSASVGDRVTITCLASEDIYTYLTWYQQKPGKAPKLLIYGANKLQDGVPSRFSGSGSGTDYTLTISSLQPEDFATY YCLQGSKFPLTFGQGTKLEIKRTVAAPSVFIFPPSDERLKSGTASVVCLLNNFYPREAKVQWKVDNALQSGNSQESVTEQDSKDST

YSLSSRLTLSKADYEKHKVYACEVTHQGLSSPVTKSENRGEC

Heterodimeric bsAb 3 HC1 (anti-IL-18)
                                                    SEQ ID NO: 50
QVQLVQSGAEVKKPGASVKVSCKVSGEISTGYYFHWVRQAPGKGLEWMGRIDPEDDSTKYAERFKDRVTMTEDTSTDTAYMELSSL RSEDTAVYYCTTWRIYRDSSGRPFYVMDAWGQGTLVTVSSASTKGPSVFPLAPSSKSTSGGTAALGCEVTDYFPEPVTVSWNSGAL TSGVHTFPAVLESSGLYSLSSVVTVPSSSLGTQTYICNVNHKPSNTKVDKKVEPKSCDKTHTCPPCPAPELAGAPSVELFPPKPKD TLMISRTPEVTCVVVDVSHEDPEVKFNWYVDGVEVHNAKTKPREEQYNSTYRVVSVLTVLHQDWLNGKEYKCKVSNKALPAPIEKT ISKAKGQPREPQVYVYPPSRDELTKNQVSLTCLVKGFYPSDIAVEWESNGQPENNYKTTPPVLDSDGSFALVSKLTVDKSRWQQGN

VFSCSVMHEALHNHYTQKSLSLSPGK

Heterodimeric bsAb 3 HC2 (anti-IL-23)
                                                    SEQ ID NO: 51
QVQLVQSGAEVKKPGASVKVSCKASGYIFITYWMTWVRQAPGQGLEWMGQIFPASGSADYNEKFEGRVTMTTDTSTSTAYMELRSL RSDDTAVYYCARGGGGFPAYWGQGTLVTVSSASTKGPSVFPLAPSSKSTSGGTAALGCRVKDYFPEPVTVSWNSGALTSGVHTFPAV LQSSGLYSLSSVVTVPSSSLGTQTYICNVNHKPSNTKVDKKVEPKSCDKTHTCPPCPAPELAGAPSVFLFPPKPKDTLMISRTPEV -continued TCVVVDVSHEDPEVKENWYVDGVEVHNAKTKPREEQYNSTYRVVSVLTVLHQDWLNGKEYKCKVSNKALPAPIEKTISKAKGQPRE PQVYVLPPSRDELTKNQVSLLCLVKGFYPSDIAVEWESNGQPENNYLTWPPVLDSDGSFFLYSKLTVDKSRWQQGNVFSCSVMHEA

LHNHYTQKSLSLSPGK

Heterodimeric bsAb 3 LC1 (anti-IL-18)
                                                                        SEQ ID NO: 52
DIQMTQSPSSVSASVGDRVTITCLASEDIYTYLTWYQQKPGKAPKLLIYGANKLQDGVPSRFSGSGSGTDYTLTISSLQPEDFATY YCLQGSKFPLTFGQGTKLEIKRTVAAPSVFIFPPSDERLKSGTASVVCLLNNFYPREAKVQWKVDNALQSGNSQESVTEQDSKDST

YSLSSRLTLSKADYEKHKVYACEVTHQGLSSPVTKSENRGEC

Heterodimeric bsAb 3 LC2 (anti-IL-23)
                                                                        SEQ ID NO: 53
DIQMTQSPSSLSASVGDRVTITCRTSENIYSYLAWYQQKPGKAPKLLIYNAKTLAEGVPSRFSGSGSGTDFTLTISSLQPEDFATY YCQHHYGIPFTFGQGTKVEIKRTVAAPSVFIFPPSDEELKSGTASVECLLNNFYPREAKVQWKVDNALQSGNSQESVTEQDSKDST

YSLSSTLTLSKADYEKHKVYACEVTHQGLSSPVTKSENRGEC

Heterodimeric bsAb 4 HC1 (anti-IL-23)
                                                                        SEQ ID NO: 54
QVQLVQSGAEVKKPGSSVKVSCKASGYTFTDQTIHWMRQAPGQGLEWIGYIYPRDDSPKYNENFKGKVTITADKSTSTAYMELSSL RSEDTAVYYCAIPDRSGYAWFIYWGQGTLVTVSSASTKGPSVFPLAPSSKSTSGGTAALGCRVKDYFPEPVTVSWNSGALTSGVHT FPAVLQSSGLYSLSSVVTVPSSSLGTQTYICNVNHKPSNTKVDKKVEPKSCDKTHTCPPCPAPELAGAPSVFLFPPKPKDTLYITR EPEVTCVVVDVSHEDPEVKFNWYVDGVEVHNAKTKPREEQYNSTYRVVSVLTVLHQDWLNGKEYKCKVSNKALPAPIEKTISKAKG QPREPQVYVYPPSRDELTKNQVSLTCLVKGFYPSDIAVEWESNGQPENNYKTTPPVLDSDGSFALVSKLTVDKSRWQQGNVFSCSV

MHEALHNHYTQKSLSLSPGK

Heterodimeric bsAb 4 HC2 (anti-IL-18)
                                                                        SEQ ID NO: 55
QVQLVQSGAEVKKPGASVKVSCKVSGEISTGYYFHWVRQAPGKGLEWMGRIDPEDDSTKYAERFKDRVTMTEDTSTDTAYMELSSL RSEDTAVYYCTTWRIYRDSSGRPFYVMDAWGQGTLVTVSSASTKGPSVFPLAPSSKSTSGGTAALGCEVTDYFPEPVTVSWNSGAL TSGVHTFPAVLESSGLYSLSSVVTVPSSSLGTQTYICNVNHKPSNTKVDKKVEPKSCDKTHTCPPCPAPELAGAPSVFLFPPKPKD TLYITREPEVTCVVVDVSHEDPEVKFNWYVDGVEVHNAKTKPREEQYNSTYRVVSVLTVLHQDWLNGKEYKCKVSNKALPAPIEKT ISKAKGQPREPQVYVLPPSRDELTKNQVSLLCLVKGFYPSDIAVEWESNGQPENNYLTWPPVLDSDGSFFLYSKLTVDKSRWQQGN

VFSCSVMHEALHNHYTQKSLSLSPGK

Heterodimeric bsAb 4 LC1 (anti-IL-23)
                                                                        SEQ ID NO: 56
DIQMTQSPSSLSASVGDRVTITCKASRDVAIAVAWYQQKPGKVPKLLIYWASTRHTGVPSRFSGSGSRTDFTLTISSLQPEDVADY FCHQYSSYPFTFGSGTKLEIKRTVAAPSVFIFPPSDEELKSGTASVECLLNNFYPREAKVQWKVDNALQSGNSQESVTEQDSKDST

YSLSSTLTLSKADYEKHKVYACEVTHQGLSSPVTKSENRGEC

Heterodimeric bsAb 4 LC2 (anti-IL-18)
                                                                        SEQ ID NO: 57
DIQMTQSPSSVSASVGDRVTITCLASEDIYTYLTWYQQKPGKAPKLLIYGANKLQDGVPSRFSGSGSGTDYTLTISSLQPEDFATY YCLQGSKFPLTFGQGTKLEIKRTVAAPSVFIFPPSDERLKSGTASVVCLLNNFYPREAKVQWKVDNALQSGNSQESVTEQDSKDST

YSLSSRLTLSKADYEKHKVYACEVTHQGLSSPVTKSENRGEC

CDRH1 of IL-23 Binding Domain
                                                                        SEQ ID NO: 58
RYVMH CDRH2 of IL-23 Binding Domain
                                                                        SEQ ID NO: 59
YINPYNDGTNYNEKFKG CDRH3 of IL-23 Binding Domain
                                                                        SEQ ID NO: 60
NWDTGL -continued CDRL1 of IL-23 Binding Domain

SEQ ID NO: 61

KASDHILKFLT

CDRL2 of IL-23 Binding Domain

SEQ ID NO: 62

GATSLET

CDRL3 of IL-23 Binding Domain

SEQ ID NO: 63

QMYWSTPFT

VH IL-23 Binding Domain

SEQ ID NO: 64

QVQLVQSGAEVKKPGSSVKVSCKASGYKFTRYVMHWVRQAPGQGLEWMGYINPYNDGTNYNEKFKGRVTI

TADKSTSTAYMELSSLRSEDTAVYYCARNWDTGLWGQGTTVTVSS

VL IL-23 Binding Domain

SEQ ID NO: 65

DIQMTQSPSSLSASVGDRVTITCKASDHILKELTWYQQKPGKAPKLLIYGATSLETGVPSRFSGSGSGTD

FTLTISSLQPEDFATYYCQMYWSTPFTFGGGTKVEIK

CDRH1 of IL-18 Binding Domain

SEQ ID NO: 66

ADGYYWS

CDRH2 of IL-18 Binding Domain

SEQ ID NO: 67

SLYYSGSTYYNPSLKG

CDRH3 of IL-18 Binding Domain

SEQ ID NO: 68

TPAYFGQDRTDFFDV

CDRL1 of IL-18 Binding Domain

SEQ ID NO: 69

RASQGISSWLA

CDRL2 of IL-18 Binding Domain

SEQ ID NO: 70

KASTLES

CDRL3 of IL-18 Binding Domain

SEQ ID NO: 71

QQSHHPPWT

VH IL-18 Binding Domain

SEQ ID NO: 72

QVQLQESGPGLVKPSETLSLTCTVSGGSISADGYYWSWIRQPPGKGLEWIGSLYYSGSTYYNPSLKGRVT

ISGDTSKNQFSLKLSSVTAADTAVYYCARTPAYFGQDRTDFFDVWGRGTLVTVSS

VL IL-18 Binding Domain

SEQ ID NO: 73

DIQMTQSPSTLSASVGDRVTITCRASQGISSWLAWYQQKPGKAPKVLIYKASTLESGVPSRFSGSGSGTE

FTLTISSLQPDDFATYYCQQSHHPPWTFGQGTKLEIKRTV

Human IL23p19: Uniprot # Q9NPF7

SEQ ID NO: 74

MLGSRAVMLLLLLPWTAQGRAVPGGSSPAWTQCQQLSQKLCTLAWSAHPLVGHMDLREEGDEETTNDVPHIQCGDGCDPQGLRDNS

QFCLQRIHQGLIFYEKLLGSDIFTGEPSLLPDSPVGQLHASLLGLSQLLQPEGHHWETQQIPSLSPSQPWQRLLLRFKILRSLQAF

VAVAARVFAHGAATLSP

Human IL12B/IL12p40: Uniport P29460

SEQ ID NO: 75

MCHQQLVISWFSLVFLASPLVAIWELKKDVYVVELDWYPDAPGEMVVLTCDTPEEDGITWTLDQSSEVLGSGKTLTIQVKEFGDAG

QYTCHKGGEVLSHSLLLLHKKEDGIWSTDILKDQKEPKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYENYTSSFFIRDIIKPDPPKNLQLKPLKNSRQVEVSWEY

PDTWSTPHSYFSLTFCVQVQGKSKREKKDRVFTDKTSATVICRKNASISVRAQDRYYSSSWSEWASVPCS

-continued

CDRH1 of IL-18 Binding Domain

SEQ ID NO: 76

SYAIS

CDRH2 of IL-18 Binding Domain

SEQ ID NO: 77

NIIPMTGQTYYAQKFQG

CDRH3 of IL-18 Binding Domain

SEQ ID NO: 78

AAYHPLVFDN

CDRL1 of IL-18 Binding Domain

SEQ ID NO: 79

SGSSSNIGNHYVN

CDRL2 of IL-18 Binding Domain

SEQ ID NO: 80

RNNHRPS

CDRL3 of IL-18 Binding Domain

SEQ ID NO: 81

QSWDYSGFSTV

VH IL-18 Binding Domain

SEQ ID NO: 82

EVQLVQSGAEVKKPGSSVKVSCKASGGTFKSYAISWVRQAPGQGLEWMGNIIPMTGQTYYAQKFQGRVTITADESTSTAYMELSSL

RSEDTAVYYCARAAYHPLVFDNWGQGTLVTVSS

VL IL-18 Binding Domain

SEQ ID NO: 83

DIVLTQPPSVSGAPGQRVTISCSGSSSNIGNHYVNWYQQLPGTAPKLLIYRNNHRPSGVPDRFSGSKSGTSASLAITGLQSEDEAD

YYCQSWDYSGFSTVFGGGTKLTVL

---

We claim:

1. A multispecific antigen binding protein comprising an interleukin 18 (IL-18) binding domain and an interleukin 23 (IL-23) binding domain wherein said multispecific antigen binding protein comprises an IL-18 binding domain comprising a heavy chain of SEQ ID NO: 55 and a light chain of SEQ ID NO: 57, and an IL-23 binding domain comprising a heavy chain of SEQ ID NO: 54 and a light chain of SEQ ID NO:56.

2. The multispecific antigen binding protein of claim 1 wherein said multispecific antigen binding protein is a bispecific antigen binding protein.

3. The multispecific antigen binding protein of claim 2 wherein said bispecific antigen binding protein is a bispecific antibody, wherein said bispecific antibody consists of said interleukin 18 (IL-18) binding domain and said interleukin 23 (IL-23) binding domain, and wherein said IL-18 binding domain consists of a heavy chain of SEQ ID NO: 55 and a light chain of SEQ ID NO: 57, and said IL-23 binding domain consists of a heavy chain of SEQ ID NO: 54 and a light chain of SEQ ID NO:56.

4. The multispecific antigen binding protein of claim 1 wherein said multispecific antigen binding protein down-regulates CXCL13 secretion.

5. A nucleic acid sequence encoding the multispecific antigen binding protein of claim 4.

6. A pharmaceutical composition comprising the multispecific antigen binding protein according to claim 4 and a pharmaceutically acceptable excipient.

7. A method for the treatment of inflammatory bowel disease (IBD) in a human subject in need thereof comprising administering to said human subject a therapeutically effective amount of a multispecific antigen binding protein, wherein said multispecific antigen binding protein comprises:
   (i) an IL-18 binding domain comprising a heavy chain of SEQ ID NO: 55 and a light chain of SEQ ID NO: 57; and
   (ii) an IL-23 binding domain comprising a heavy chain of SEQ ID NO: 54 and a light chain of SEQ ID NO:56.

8. The method according to claim 7 wherein the inflammatory bowel disease (IBD) is ulcerative colitis (UC) or Crohn's Disease (CD).

9. A method for the treatment of UC or CD in a human subject in need thereof comprising administering to said human subject a therapeutically effective amount of a pharmaceutical composition, wherein said pharmaceutical composition comprises:
   (i) a multispecific antigen binding protein comprising an interleukin 18 (IL-18) binding domain and an interleukin 23 (IL-23) binding domain wherein the IL-18 binding domain comprises a heavy chain of SEQ ID NO: 55 and a light chain of SEQ ID NO: 57, and the IL-23 binding domain comprises a heavy chain of SEQ ID NO: 54 and a light chain of SEQ ID NO: 56; and
   (ii) a pharmaceutically acceptable excipient.

* * * * *

SEQUENCE LISTING

Sequence total quantity: 83
SEQ ID NO: 1              moltype = AA  length = 157
FEATURE                   Location/Qualifiers
source                    1..157
                          mol_type = protein
                          organism = Homo sapiens
SEQUENCE: 1
YFGKLESKLS VIRNLNDQVL FIDQGNRPLF EDMTDSDCRD NAPRTIFIIS MYKDSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 2              moltype = AA  length = 5
FEATURE                   Location/Qualifiers
source                    1..5
                          mol_type = protein
                          organism = synthetic construct
SEQUENCE: 2
GYYFH                                                               5

SEQ ID NO: 3              moltype = AA  length = 17
FEATURE                   Location/Qualifiers
source                    1..17
                          mol_type = protein
                          organism = synthetic construct
SEQUENCE: 3
RIDPEDDSTK YAERFKD                                                  17

SEQ ID NO: 4              moltype = AA  length = 17
FEATURE                   Location/Qualifiers
source                    1..17
                          mol_type = protein
                          organism = synthetic construct
SEQUENCE: 4
WRIYRDSSGR PFYVMDA                                                  17

SEQ ID NO: 5              moltype = AA  length = 11
FEATURE                   Location/Qualifiers
source                    1..11

-continued

```
                              mol_type = protein
                              organism = synthetic construct
SEQUENCE: 5
LASEDIYTYL T                                                       11

SEQ ID NO: 6          moltype = AA   length = 7
FEATURE               Location/Qualifiers
source                1..7
                      mol_type = protein
                      organism = synthetic construct
SEQUENCE: 6
GANKLQD                                                            7

SEQ ID NO: 7          moltype = AA   length = 9
FEATURE               Location/Qualifiers
source                1..9
                      mol_type = protein
                      organism = synthetic construct
SEQUENCE: 7
LQGSKFPLT                                                          9

SEQ ID NO: 8          moltype = AA   length = 126
FEATURE               Location/Qualifiers
source                1..126
                      mol_type = protein
                      organism = synthetic construct
SEQUENCE: 8
QVQLVQSGAE VKKPGASVKV SCKVSGEIST GYYFHWVRQA PGKGLEWMGR IDPEDDSTKY   60
AERFKDRVTM TEDTSTDTAY MELSSLRSED TAVYYCTTWR IYRDSSGRPF YVMDAWGQGT   120
LVTVSS                                                             126

SEQ ID NO: 9          moltype = AA   length = 107
FEATURE               Location/Qualifiers
source                1..107
                      mol_type = protein
                      organism = synthetic construct
SEQUENCE: 9
DIQMTQSPSS VSASVGDRVT ITCLASEDIY TYLTWYQQKP GKAPKLLIYG ANKLQDGVPS   60
RFSGSGSGTD YTLTISSLQP EDFATYYCLQ GSKFPLTFGQ GTKLEIK                107

SEQ ID NO: 10         moltype = AA   length = 5
FEATURE               Location/Qualifiers
source                1..5
                      mol_type = protein
                      organism = synthetic construct
SEQUENCE: 10
DQTIH                                                              5

SEQ ID NO: 11         moltype = AA   length = 17
FEATURE               Location/Qualifiers
source                1..17
                      mol_type = protein
                      organism = synthetic construct
SEQUENCE: 11
YIYPRDDSPK YNENFKG                                                 17

SEQ ID NO: 12         moltype = AA   length = 11
FEATURE               Location/Qualifiers
source                1..11
                      mol_type = protein
                      organism = synthetic construct
SEQUENCE: 12
PDRSGYAWFI Y                                                       11

SEQ ID NO: 13         moltype = AA   length = 11
FEATURE               Location/Qualifiers
source                1..11
                      mol_type = protein
                      organism = synthetic construct
SEQUENCE: 13
KASRDVAIAV A                                                       11

SEQ ID NO: 14         moltype = AA   length = 7
FEATURE               Location/Qualifiers
source                1..7
                      mol_type = protein
                      organism = synthetic construct
SEQUENCE: 14
WASTRHT                                                            7
```

-continued

```
SEQ ID NO: 15               moltype = AA   length = 9
FEATURE                     Location/Qualifiers
source                      1..9
                            mol_type = protein
                            organism = synthetic construct
SEQUENCE: 15
HQYSSYPFT                                                         9

SEQ ID NO: 16               moltype = AA   length = 120
FEATURE                     Location/Qualifiers
source                      1..120
                            mol_type = protein
                            organism = synthetic construct
SEQUENCE: 16
QVQLVQSGAE VKKPGSSVKV SCKASGYTFT DQTIHWMRQA PGQGLEWIGY IYPRDDSPKY  60
NENFKGKVTI TADKSTSTAY MELSSLRSED TAVYYCAIPD RSGYAWFIYW GQGTLVTVSS  120

SEQ ID NO: 17               moltype = AA   length = 107
FEATURE                     Location/Qualifiers
source                      1..107
                            mol_type = protein
                            organism = synthetic construct
SEQUENCE: 17
DIQMTQSPSS LSASVGDRVT ITCKASRDVA IAVAWYQQKP GKVPKLLIYW ASTRHTGVPS  60
RFSGSGSRTD FTLTISSLQP EDVADYFCHQ YSSYPFTFGS GTKLEIK              107

SEQ ID NO: 18               moltype = AA   length = 5
FEATURE                     Location/Qualifiers
source                      1..5
                            mol_type = protein
                            organism = synthetic construct
SEQUENCE: 18
TYWMT                                                             5

SEQ ID NO: 19               moltype = AA   length = 17
FEATURE                     Location/Qualifiers
source                      1..17
                            mol_type = protein
                            organism = synthetic construct
SEQUENCE: 19
QIFPASGSAD YNEKFEG                                                17

SEQ ID NO: 20               moltype = AA   length = 7
FEATURE                     Location/Qualifiers
source                      1..7
                            mol_type = protein
                            organism = synthetic construct
SEQUENCE: 20
GGGGFAY                                                           7

SEQ ID NO: 21               moltype = AA   length = 11
FEATURE                     Location/Qualifiers
source                      1..11
                            mol_type = protein
                            organism = synthetic construct
SEQUENCE: 21
RTSENIYSYL A                                                      11

SEQ ID NO: 22               moltype = AA   length = 7
FEATURE                     Location/Qualifiers
source                      1..7
                            mol_type = protein
                            organism = synthetic construct
SEQUENCE: 22
NAKTLAE                                                           7

SEQ ID NO: 23               moltype = AA   length = 9
FEATURE                     Location/Qualifiers
source                      1..9
                            mol_type = protein
                            organism = synthetic construct
SEQUENCE: 23
QHHYGIPFT                                                         9

SEQ ID NO: 24               moltype = AA   length = 116
FEATURE                     Location/Qualifiers
source                      1..116
                            mol_type = protein
```

-continued

```
                             organism = synthetic construct
SEQUENCE: 24
QVQLVQSGAE VKKPGASVKV SCKASGYIFI TYWMTWVRQA PGQGLEWMGQ IFPASGSADY   60
NEKFEGRVTM TTDTSTSTAY MELRSLRSDD TAVYYCARGG GGFAYWGQGT LVTVSS        116

SEQ ID NO: 25              moltype = AA  length = 107
FEATURE                    Location/Qualifiers
source                     1..107
                           mol_type = protein
                           organism = synthetic construct
SEQUENCE: 25
DIQMTQSPSS LSASVGDRVT ITCRTSENIY SYLAWYQQKP GKAPKLLIYN AKTLAEGVPS   60
RFSGSGSGTD FTLTISSLQP EDFATYYCQH HYGIPFTFGQ GTKVEIK                 107

SEQ ID NO: 26              moltype = AA  length = 5
FEATURE                    Location/Qualifiers
source                     1..5
                           mol_type = protein
                           organism = synthetic construct
SEQUENCE: 26
TYWLG                                                               5

SEQ ID NO: 27              moltype = AA  length = 17
FEATURE                    Location/Qualifiers
source                     1..17
                           mol_type = protein
                           organism = synthetic construct
SEQUENCE: 27
IMSPVDSDIR YSPSFQG                                                  17

SEQ ID NO: 28              moltype = AA  length = 10
FEATURE                    Location/Qualifiers
source                     1..10
                           mol_type = protein
                           organism = synthetic construct
SEQUENCE: 28
RRPGQGYFDF                                                          10

SEQ ID NO: 29              moltype = AA  length = 11
FEATURE                    Location/Qualifiers
source                     1..11
                           mol_type = protein
                           organism = synthetic construct
SEQUENCE: 29
RASQGISSWL A                                                        11

SEQ ID NO: 30              moltype = AA  length = 7
FEATURE                    Location/Qualifiers
source                     1..7
                           mol_type = protein
                           organism = synthetic construct
SEQUENCE: 30
AASSLQS                                                             7

SEQ ID NO: 31              moltype = AA  length = 9
FEATURE                    Location/Qualifiers
source                     1..9
                           mol_type = protein
                           organism = synthetic construct
SEQUENCE: 31
QQYNIYPYT                                                           9

SEQ ID NO: 32              moltype = AA  length = 119
FEATURE                    Location/Qualifiers
source                     1..119
                           mol_type = protein
                           organism = synthetic construct
SEQUENCE: 32
EVQLVQSGAE VKKPGESLKI SCKGSGYSFT TYWLGWVRQM PGKGLDWIGI MSPVDSDIRY   60
SPSFQGQVTM SVDKSITTAY LQWNSLKASD TAMYYCARRR PGQGYFDFWG QGTLVTVSS    119

SEQ ID NO: 33              moltype = AA  length = 107
FEATURE                    Location/Qualifiers
source                     1..107
                           mol_type = protein
                           organism = synthetic construct
SEQUENCE: 33
DIQMTQSPSS LSASVGDRVT ITCRASQGIS SWLAWYQQKP EKAPKSLIYA ASSLQSGVPS   60
RFSGSGSGTD FTLTISSLQP EDFATYYCQQ YNIYPYTFGQ GTKLEIK                 107
```

-continued

```
SEQ ID NO: 34          moltype = AA  length = 5
FEATURE                Location/Qualifiers
source                 1..5
                       mol_type = protein
                       organism = synthetic construct
SEQUENCE: 34
NYWIG                                                        5

SEQ ID NO: 35          moltype = AA  length = 17
FEATURE                Location/Qualifiers
source                 1..17
                       mol_type = protein
                       organism = synthetic construct
SEQUENCE: 35
IIDPSNSYTR YSPSFQG                                           17

SEQ ID NO: 36          moltype = AA  length = 8
FEATURE                Location/Qualifiers
source                 1..8
                       mol_type = protein
                       organism = synthetic construct
SEQUENCE: 36
WYYKPFDV                                                     8

SEQ ID NO: 37          moltype = AA  length = 14
FEATURE                Location/Qualifiers
source                 1..14
                       mol_type = protein
                       organism = synthetic construct
SEQUENCE: 37
TGSSSNIGSG YDVH                                              14

SEQ ID NO: 38          moltype = AA  length = 7
FEATURE                Location/Qualifiers
source                 1..7
                       mol_type = protein
                       organism = synthetic construct
SEQUENCE: 38
GNSKRPS                                                      7

SEQ ID NO: 39          moltype = AA  length = 11
FEATURE                Location/Qualifiers
source                 1..11
                       mol_type = protein
                       organism = synthetic construct
SEQUENCE: 39
ASWTDGLSLV V                                                 11

SEQ ID NO: 40          moltype = AA  length = 120
FEATURE                Location/Qualifiers
source                 1..120
                       mol_type = protein
                       organism = synthetic construct
SEQUENCE: 40
EVQLVQSGAE VKKPGESLKI SCKGSGYSFS NYWIGWVRQM PGKGLEWMGI IDPSNSYTRY  60
SPSFQGQVTI SADKSISTAY LQWSSLKASD TAMYYCARWY YKPFDVWGQG TLVTVSSAST  120

SEQ ID NO: 41          moltype = AA  length = 111
FEATURE                Location/Qualifiers
source                 1..111
                       mol_type = protein
                       organism = synthetic construct
SEQUENCE: 41
QSVLTQPPSV SGAPGQRVTI SCTGSSSNIG SGYDVHWYQQ LPGTAPKLLI YGNSKRPSGV  60
PDRFSGSKSG TSASLAITGL QSEDEADYYC ASWTDGLSLV VFGGGTKLTV L           111

SEQ ID NO: 42          moltype = AA  length = 456
FEATURE                Location/Qualifiers
source                 1..456
                       mol_type = protein
                       organism = synthetic construct
SEQUENCE: 42
QVQLVQSGAE VKKPGASVKV SCKVSGEIST GYYFHWVRQA PGKGLEWMGR IDPEDDSTKY  60
AERFKDRVTM TEDTSTDTAY MELSSLRSED TAVYYCTTWR IYRDSSGRPF YVMDAWGQGT  120
LVTVSSASTK GPSVFPLAPS SKSTSGGTAA LGCEVTDYFP EPVTVSWNSG ALTSGVHTFP  180
AVLESSGLYS LSSVVTVPSS SLGTQTYICN VNHKPSNTKV DKKVEPKSCD KTHTCPPCPA  240
PELAGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYVY  360
```

-continued

```
PPSRDELTKN QVSLTCLVKG FYPSDIAVEW ESNGQPENNY KTTPPVLDSD GSFALVSKLT  420
VDKSRWQQGN VFSCSVMHEA LHNHYTQKSL SLSPGK                              456

SEQ ID NO: 43              moltype = AA  length = 450
FEATURE                    Location/Qualifiers
source                     1..450
                           mol_type = protein
                           organism = synthetic construct
SEQUENCE: 43
QVQLVQSGAE VKKPGSSVKV SCKASGYTFT DQTIHWMRQA PGQGLEWIGY IYPRDDSPKY  60
NENFKGKVTI TADKSTSTAY MELSSLRSED TAVYYCAIPD RSGYAWFIYW GQGTLVTVSS  120
ASTKGPSVFP LAPSSKSTSG GTAALGCRVK DYFPEPVTVS WNSGALTSGV HTFPAVLQSS  180
GLYSLSSVVT VPSSSLGTQT YICNVNHKPS NTKVDKKVEP KSCDKTHTCP PCPAPELAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVLPPSRDE  360
LTKNQVSLLC LVKGFYPSDI AVEWESNGQP ENNYLTWPPV LDSDGSFFLY SKLTVDKSRW  420
QQGNVFSCSV MHEALHNHYT QKSLSLSPGK                                    450

SEQ ID NO: 44              moltype = AA  length = 214
FEATURE                    Location/Qualifiers
source                     1..214
                           mol_type = protein
                           organism = synthetic construct
SEQUENCE: 44
DIQMTQSPSS VSASVGDRVT ITCLASEDIY TYLTWYQQKP GKAPKLLIYG ANKLQDGVPS  60
RFSGSGSGTD YTLTISSLQP EDFATYYCLQ GSKFPLTFGQ GTKLEIKRTV AAPSVFIFPP  120
SDERLKSGTA SVVCLLNNFY PREAKVQWKV DNALQSGNSQ ESVTEQDSKD STYSLSSRLT  180
LSKADYEKHK VYACEVTHQG LSSPVTKSFN RGEC                               214

SEQ ID NO: 45              moltype = AA  length = 214
FEATURE                    Location/Qualifiers
source                     1..214
                           mol_type = protein
                           organism = synthetic construct
SEQUENCE: 45
DIQMTQSPSS LSASVGDRVT ITCKASRDVA IAVAWYQQKP GKVPKLLIYW ASTRHTGVPS  60
RFSGSGSRTD FTLTISSLQP EDVADYFCHQ YSSYPFTFGS GTKLEIKRTV AAPSVFIFPP  120
SDEELKSGTA SVECLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 46              moltype = AA  length = 233
FEATURE                    Location/Qualifiers
source                     1..233
                           mol_type = protein
                           organism = synthetic construct
SEQUENCE: 46
QVQLVQSGAE VKKPGSSVKV SCKASGYTFT DQTIHWMRQA PGQGLEWIGY IYPRDDSPKY  60
NENFKGKVTI TADKSTSTAY MELSSLRSED TAVYYCAIPD RSGYAWFIYW GQGTLVTVSS  120
ASTKGPSVFP LAPSSKSTSG GTAALGCRVK DYFPEPVTVS WNSGALTSGV HTFPAVLQSS  180
GLYSLSSVVT VPSSSLGTQT YICNVNHKPS NTKVDKKVEP KSCDKTHTCP PCP         233

SEQ ID NO: 47              moltype = AA  length = 456
FEATURE                    Location/Qualifiers
source                     1..456
                           mol_type = protein
                           organism = synthetic construct
SEQUENCE: 47
QVQLVQSGAE VKKPGASVKV SCKVSGEIST GYYFHWVRQA PGKGLEWMGR IDPEDDSTKY  60
AERFKDRVTM TEDTSTDTAY MELSSLRSED TAVYYCTTWR IYRDSSGRPF YVMDAWGQGT  120
LVTVSSASTK GPSVFPLAPS SKSTSGGTAA LGCEVTDYFP EPVTVSWNSG ALTSGVHTFP  180
AVLESSGLYS LSSVVTVPSS SLGTQTYICN VNHKPSNTKV DKKVEPKSCD KTHTCPPCPA  240
PELAGAPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYVL  360
PPSRDELTKN QVSLLCLVKG FYPSDIAVEW ESNGQPENNY LTWPPVLDSD GSFFLYSKLT  420
VDKSRWQQGN VFSCSVMHEA LHNHYTQKSL SLSPGK                              456

SEQ ID NO: 48              moltype = AA  length = 214
FEATURE                    Location/Qualifiers
source                     1..214
                           mol_type = protein
                           organism = synthetic construct
SEQUENCE: 48
DIQMTQSPSS LSASVGDRVT ITCKASRDVA IAVAWYQQKP GKVPKLLIYW ASTRHTGVPS  60
RFSGSGSRTD FTLTISSLQP EDVADYFCHQ YSSYPFTFGS GTKLEIKRTV AAPSVFIFPP  120
SDEELKSGTA SVECLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 49              moltype = AA  length = 214
FEATURE                    Location/Qualifiers
```

-continued

```
source                    1..214
                          mol_type = protein
                          organism = synthetic construct
SEQUENCE: 49
DIQMTQSPSS VSASVGDRVT ITCLASEDIY TYLTWYQQKP GKAPKLLIYG ANKLQDGVPS    60
RFSGSGSGTD YTLTISSLQP EDFATYYCLQ GSKFPLTFGQ GTKLEIKRTV AAPSVFIFPP   120
SDERLKSGTA SVVCLLNNFY PREAKVQWKV DNALQSGNSQ ESVTEQDSKD STYSLSSRLT   180
LSKADYEKHK VYACEVTHQG LSSPVTKSFN RGEC                               214

SEQ ID NO: 50             moltype = AA   length = 456
FEATURE                   Location/Qualifiers
source                    1..456
                          mol_type = protein
                          organism = synthetic construct
SEQUENCE: 50
QVQLVQSGAE VKKPGASVKV SCKVSGEIST GYYFHWVRQA PGKGLEWMGR IDPEDDSTKY    60
AERFKDRVTM TEDTSTDTAY MELSSLRSED TAVYYCTTWR IYRDSSGRPF YVMDAWGQGT   120
LVTVSSASTK GPSVFPLAPS SKSTSGGTAA LGCEVTDYFP EPVTVSWNSG ALTSGVHTFP   180
AVLESSGLYS LSSVVTVPSS SLGTQTYICN VNHKPSNTKV DKKVEPKSCD KTHTCPPCPA   240
PELAGAPSVF LFPPKPKDTL MISRTPEVTC VVVDVSHEDP EVKFNWYVDG VEVHNAKTKP   300
REEQYNSTYR VVSVLTVLHQ DWLNGKEYKC KVSNKALPAP IEKTISKAKG QPREPQVYVY   360
PPSRDELTKN QVSLTCLVKG FYPSDIAVEW ESNGQPENNY KTTPPVLDSD GSFALVSKLT   420
VDKSRWQQGN VFSCSVMHEA LHNHYTQKSL SLSPGK                            456

SEQ ID NO: 51             moltype = AA   length = 446
FEATURE                   Location/Qualifiers
source                    1..446
                          mol_type = protein
                          organism = synthetic construct
SEQUENCE: 51
QVQLVQSGAE VKKPGASVKV SCKASGYIFI TYWMTWVRQA PGQGLEWMGQ IFPASGSADY    60
NEKFEGRVTM TTDTSTSTAY MELRSLRSDD TAVYYCARGG GGFAYWGQGT LVTVSSASTK   120
GPSVFPLAPS SKSTSGGTAA LGCRVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELAGAPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYVL PPSRDELTKN   360
QVSLLCLVKG FYPSDIAVEW ESNGQPENNY LTWPPVLDSD GSFFLYSKLT VDKSRWQQGN   420
VFSCSVMHEA LHNHYTQKSL SLSPGK                                       446

SEQ ID NO: 52             moltype = AA   length = 214
FEATURE                   Location/Qualifiers
source                    1..214
                          mol_type = protein
                          organism = synthetic construct
SEQUENCE: 52
DIQMTQSPSS VSASVGDRVT ITCLASEDIY TYLTWYQQKP GKAPKLLIYG ANKLQDGVPS    60
RFSGSGSGTD YTLTISSLQP EDFATYYCLQ GSKFPLTFGQ GTKLEIKRTV AAPSVFIFPP   120
SDERLKSGTA SVVCLLNNFY PREAKVQWKV DNALQSGNSQ ESVTEQDSKD STYSLSSRLT   180
LSKADYEKHK VYACEVTHQG LSSPVTKSFN RGEC                               214

SEQ ID NO: 53             moltype = AA   length = 214
FEATURE                   Location/Qualifiers
source                    1..214
                          mol_type = protein
                          organism = synthetic construct
SEQUENCE: 53
DIQMTQSPSS LSASVGDRVT ITCRTSENIY SYLAWYQQKP GKAPKLLIYN AKTLAEGVPS    60
RFSGSGSGTD FTLTISSLQP EDFATYYCQH HYGIPFTFGQ GTKVEIKRTV AAPSVFIFPP   120
SDEELKSGTA SVECLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 54             moltype = AA   length = 450
FEATURE                   Location/Qualifiers
source                    1..450
                          mol_type = protein
                          organism = synthetic construct
SEQUENCE: 54
QVQLVQSGAE VKKPGSSVKV SCKASGYTFT DQTIHWMRQA PGQGLEWIGY IYPRDDSPKY    60
NENFKGKVTI TADKSTSTAY MELSSLRSED TAVYYCAIPD RSGYAWFIYW GQGTLVTVSS   120
ASTKGPSVFP LAPSSKSTSG GTAALGCRVK DYFPEPVTVS WNSGALTSGV HTFPAVLQSS   180
GLYSLSSVVT VPSSSLGTQT YICNVNHKPS NTKVDKKVEP KSCDKTHTCP PCPAPELAGA   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYVYPPSRDE   360
LTKNQVSLTC LVKGFYPSDI AVEWESNGQP ENNYKTTPPV LDSDGSFALV SKLTVDKSRW   420
QQGNVFSCSV MHEALHNHYT QKSLSLSPGK                                   450

SEQ ID NO: 55             moltype = AA   length = 456
FEATURE                   Location/Qualifiers
source                    1..456
```

-continued

```
                          mol_type = protein
                          organism = synthetic construct
SEQUENCE: 55
QVQLVQSGAE  VKKPGASVKV  SCKVSGEIST  GYYFHWVRQA  PGKGLEWMGR  IDPEDDSTKY   60
AERFKDRVTM  TEDTSTDTAY  MELSSLRSED  TAVYYCTTWR  IYRDSSGRPF  YVMDAWGQGT  120
LVTVSSASTK  GPSVFPLAPS  SKSTSGGTAA  LGCEVTDYFP  EPVTVSWNSG  ALTSGVHTFP  180
AVLESSGLYS  LSSVVTVPSS  SLGTQTYICN  VNHKPSNTKV  DKKVEPKSCD  KTHTCPPCPA  240
PELAGAPSVF  LFPPKPKDTL  YITREPEVTC  VVVDVSHEDP  EVKFNWYVDG  VEVHNAKTKP  300
REEQYNSTYR  VVSVLTVLHQ  DWLNGKEYKC  KVSNKALPAP  IEKTISKAKG  QPREPQVYVL  360
PPSRDELTKN  QVSLLCLVKG  FYPSDIAVEW  ESNGQPENNY  LTWPPVLDSD  GSFFLYSKLT  420
VDKSRWQQGN  VFSCSVMHEA  LHNHYTQKSL  SLSPGK                                456

SEQ ID NO: 56            moltype = AA  length = 214
FEATURE                  Location/Qualifiers
source                   1..214
                          mol_type = protein
                          organism = synthetic construct
SEQUENCE: 56
DIQMTQSPSS  LSASVGDRVT  ITCKASRDVA  IAVAWYQQKP  GKVPKLLIYW  ASTRHTGVPS   60
RFSGSGSRTD  FTLTISSLQP  EDVADYFCHQ  YSSYPFTFGS  GTKLEIKRTV  AAPSVFIFPP  120
SDEELKSGTA  SVECLLNNFY  PREAKVQWKV  DNALQSGNSQ  ESVTEQDSKD  STYSLSSTLT  180
LSKADYEKHK  VYACEVTHQG  LSSPVTKSFN  RGEC                                214

SEQ ID NO: 57            moltype = AA  length = 214
FEATURE                  Location/Qualifiers
source                   1..214
                          mol_type = protein
                          organism = synthetic construct
SEQUENCE: 57
DIQMTQSPSS  VSASVGDRVT  ITCLASEDIY  TYLTWYQQKP  GKAPKLLIYG  ANKLQDGVPS   60
RFSGSGSGTD  YTLTISSLQP  EDFATYYCLQ  GSKFPLTFGQ  GTKLEIKRTV  AAPSVFIFPP  120
SDERLKSGTA  SVVCLLNNFY  PREAKVQWKV  DNALQSGNSQ  ESVTEQDSKD  STYSLSSRLT  180
LSKADYEKHK  VYACEVTHQG  LSSPVTKSFN  RGEC                                214

SEQ ID NO: 58            moltype = AA  length = 5
FEATURE                  Location/Qualifiers
source                   1..5
                          mol_type = protein
                          organism = synthetic construct
SEQUENCE: 58
RYVMH                                                                     5

SEQ ID NO: 59            moltype = AA  length = 17
FEATURE                  Location/Qualifiers
source                   1..17
                          mol_type = protein
                          organism = synthetic construct
SEQUENCE: 59
YINPYNDGTN  YNEKFKG                                                      17

SEQ ID NO: 60            moltype = AA  length = 6
FEATURE                  Location/Qualifiers
source                   1..6
                          mol_type = protein
                          organism = synthetic construct
SEQUENCE: 60
NWDTGL                                                                    6

SEQ ID NO: 61            moltype = AA  length = 11
FEATURE                  Location/Qualifiers
source                   1..11
                          mol_type = protein
                          organism = synthetic construct
SEQUENCE: 61
KASDHILKFL  T                                                            11

SEQ ID NO: 62            moltype = AA  length = 7
FEATURE                  Location/Qualifiers
source                   1..7
                          mol_type = protein
                          organism = synthetic construct
SEQUENCE: 62
GATSLET                                                                   7

SEQ ID NO: 63            moltype = AA  length = 9
FEATURE                  Location/Qualifiers
source                   1..9
                          mol_type = protein
                          organism = synthetic construct
```

```
SEQUENCE: 63
QMYWSTPFT                                                                           9

SEQ ID NO: 64           moltype = AA  length = 115
FEATURE                 Location/Qualifiers
source                  1..115
                        mol_type = protein
                        organism = synthetic construct
SEQUENCE: 64
QVQLVQSGAE VKKPGSSVKV SCKASGYKFT RYVMHWVRQA PGQGLEWMGY INPYNDGTNY  60
NEKFKGRVTI TADKSTSTAY MELSSLRSED TAVYYCARNW DTGLWGQGTT VTVSS        115

SEQ ID NO: 65           moltype = AA  length = 107
FEATURE                 Location/Qualifiers
source                  1..107
                        mol_type = protein
                        organism = synthetic construct
SEQUENCE: 65
DIQMTQSPSS LSASVGDRVT ITCKASDHIL KFLTWYQQKP GKAPKLLIYG ATSLETGVPS  60
RFSGSGSGTD FTLTISSLQP EDFATYYCQM YWSTPFTFGG GTKVEIK               107

SEQ ID NO: 66           moltype = AA  length = 7
FEATURE                 Location/Qualifiers
source                  1..7
                        mol_type = protein
                        organism = synthetic construct
SEQUENCE: 66
ADGYYWS                                                                             7

SEQ ID NO: 67           moltype = AA  length = 16
FEATURE                 Location/Qualifiers
source                  1..16
                        mol_type = protein
                        organism = synthetic construct
SEQUENCE: 67
SLYYSGSTYY NPSLKG                                                                   16

SEQ ID NO: 68           moltype = AA  length = 15
FEATURE                 Location/Qualifiers
source                  1..15
                        mol_type = protein
                        organism = synthetic construct
SEQUENCE: 68
TPAYFGQDRT DFFDV                                                                    15

SEQ ID NO: 69           moltype = AA  length = 11
FEATURE                 Location/Qualifiers
source                  1..11
                        mol_type = protein
                        organism = synthetic construct
SEQUENCE: 69
RASQGISSWL A                                                                        11

SEQ ID NO: 70           moltype = AA  length = 7
FEATURE                 Location/Qualifiers
source                  1..7
                        mol_type = protein
                        organism = synthetic construct
SEQUENCE: 70
KASTLES                                                                             7

SEQ ID NO: 71           moltype = AA  length = 9
FEATURE                 Location/Qualifiers
source                  1..9
                        mol_type = protein
                        organism = synthetic construct
SEQUENCE: 71
QQSHHPPWT                                                                           9

SEQ ID NO: 72           moltype = AA  length = 125
FEATURE                 Location/Qualifiers
source                  1..125
                        mol_type = protein
                        organism = synthetic construct
SEQUENCE: 72
QVQLQESGPG LVKPSETLSL TCTVSGGSIS ADGYYWSWIR QPPGKGLEWI GSLYYSGSTY  60
YNPSLKGRVT ISGDTSKNQF SLKLSSVTAA DTAVYYCART PAYFGQDRTD FFDVWGRGTL  120
VTVSS                                                                               125
```

```
SEQ ID NO: 73              moltype = AA  length = 110
FEATURE                    Location/Qualifiers
source                     1..110
                           mol_type = protein
                           organism = synthetic construct
SEQUENCE: 73
DIQMTQSPST LSASVGDRVT ITCRASQGIS SWLAWYQQKP GKAPKVLIYK ASTLESGVPS   60
RFSGSGSGTE FTLTISSLQP DDFATYYCQQ SHHPPWTFGQ GTKLEIKRTV             110

SEQ ID NO: 74              moltype = AA  length = 189
FEATURE                    Location/Qualifiers
source                     1..189
                           mol_type = protein
                           organism = Homo sapiens
SEQUENCE: 74
MLGSRAVMLL LLLPWTAQGR AVPGGSSPAW TQCQQLSQKL CTLAWSAHPL VGHMDLREEG   60
DEETTNDVPH IQCGDGCDPQ GLRDNSQFCL QRIHQGLIFY EKLLGSDIFT GEPSLLPDSP  120
VGQLHASLLG LSQLLQPEGH HWETQQIPSL SPSQPWQRLL LRFKILRSLQ AFVAVAARVF  180
AHGAATLSP                                                         189

SEQ ID NO: 75              moltype = AA  length = 328
FEATURE                    Location/Qualifiers
source                     1..328
                           mol_type = protein
                           organism = Homo sapiens
SEQUENCE: 75
MCHQQLVISW FSLVFLASPL VAIWELKKDV YVVELDWYPD APGEMVVLTC DTPEEDGITW   60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                                    328

SEQ ID NO: 76              moltype = AA  length = 5
FEATURE                    Location/Qualifiers
source                     1..5
                           mol_type = protein
                           organism = synthetic construct
SEQUENCE: 76
SYAIS                                                               5

SEQ ID NO: 77              moltype = AA  length = 17
FEATURE                    Location/Qualifiers
source                     1..17
                           mol_type = protein
                           organism = synthetic construct
SEQUENCE: 77
NIIPMTGQTY YAQKFQG                                                 17

SEQ ID NO: 78              moltype = AA  length = 10
FEATURE                    Location/Qualifiers
source                     1..10
                           mol_type = protein
                           organism = synthetic construct
SEQUENCE: 78
AAYHPLVFDN                                                         10

SEQ ID NO: 79              moltype = AA  length = 13
FEATURE                    Location/Qualifiers
source                     1..13
                           mol_type = protein
                           organism = synthetic construct
SEQUENCE: 79
SGSSSNIGNH YVN                                                     13

SEQ ID NO: 80              moltype = AA  length = 7
FEATURE                    Location/Qualifiers
source                     1..7
                           mol_type = protein
                           organism = synthetic construct
SEQUENCE: 80
RNNHRPS                                                            7

SEQ ID NO: 81              moltype = AA  length = 11
FEATURE                    Location/Qualifiers
source                     1..11
                           mol_type = protein
                           organism = synthetic construct
SEQUENCE: 81
```

-continued

```
QSWDYSGFST V                                                       11

SEQ ID NO: 82          moltype = AA  length = 119
FEATURE                Location/Qualifiers
source                 1..119
                       mol_type = protein
                       organism = synthetic construct
SEQUENCE: 82
EVQLVQSGAE VKKPGSSVKV SCKASGGTFK SYAISWVRQA PGQGLEWMGN IIPMTGQTYY  60
AQKFQGRVTI TADESTSTAY MELSSLRSED TAVYYCARAA YHPLVFDNWG QGTLVTVSS   119

SEQ ID NO: 83          moltype = AA  length = 110
FEATURE                Location/Qualifiers
source                 1..110
                       mol_type = protein
                       organism = synthetic construct
SEQUENCE: 83
DIVLTQPPSV SGAPGQRVTI SCSGSSSNIG NHYVNWYQQL PGTAPKLLIY RNNHRPSGVP  60
DRFSGSKSGT SASLAITGLQ SEDEADYYCQ SWDYSGFSTV FGGGTKLTVL            110
```